US009066827B2

(12) United States Patent
Schmid et al.

(10) Patent No.: US 9,066,827 B2
(45) Date of Patent: Jun. 30, 2015

(54) EXPANDABLE SLIDE AND LOCK STENT

(71) Applicant: REVA Medical, Inc., San Diego, CA (US)

(72) Inventors: Eric Schmid, San Diego, CA (US); Andrew Morris, San Diego, CA (US); Keith Weier, San Diego, CA (US); Craig Bonsignore, Pleasanton, CA (US); Keith Esser, San Diego, CA (US); Steven C. Howard, San Diego, CA (US); Joseph A. DiPari, La Mesa, CA (US)

(73) Assignee: REVA Medical, Inc., San Diego, CA (US)

( * ) Notice: Subject to any disclaimer, the term of this patent is extended or adjusted under 35 U.S.C. 154(b) by 0 days.

(21) Appl. No.: 14/017,824

(22) Filed: Sep. 4, 2013

(65) Prior Publication Data
US 2014/0094897 A1    Apr. 3, 2014

Related U.S. Application Data

(63) Continuation of application No. 13/113,894, filed on May 23, 2011, now Pat. No. 8,545,547, which is a continuation of application No. 12/577,018, filed on Oct. 9, 2009, now Pat. No. 7,947,071.

(60) Provisional application No. 61/231,972, filed on Aug. 6, 2009, provisional application No. 61/104,683, filed on Oct. 10, 2008.

(51) Int. Cl.
*A61F 2/06*    (2013.01)
*A61F 2/93*    (2013.01)
*A61F 2/92*    (2013.01)

(52) U.S. Cl.
CPC ... *A61F 2/93* (2013.01); *A61F 2/92* (2013.01); *A61F 2220/0016* (2013.01); *A61F 2230/0091* (2013.01)

(58) Field of Classification Search
CPC .......................................................... A61F 2/93
USPC ................................ 623/1.15, 1.17, 1.2, 1.22
See application file for complete search history.

(56) References Cited

U.S. PATENT DOCUMENTS 2,361,506 A    10/1944    Gray et al.
3,620,218 A    11/1971    Schmitt
(Continued)

FOREIGN PATENT DOCUMENTS

CA    2368659    10/2000
CA    2590672    4/2014
(Continued)

OTHER PUBLICATIONS

International Preliminary Report on Patentability in International Application No. PCT/US2009/060256, mailed Apr. 12, 2011, 7 pp.
(Continued)

*Primary Examiner* — Alvin Stewart
(74) *Attorney, Agent, or Firm* — Knobbe, Martens, Olson & Bear, LLP

(57) ABSTRACT

An expandable slide and lock stent is provided that comprises a plurality of radial elements interconnected to form a tubular member. Each radial element can comprise a helical backbone and at least one elongate member extending from the helical backbone in a circumferential direction. Each backbone can have at least one slot that can be configured to receive an elongate member of an adjacent radial element.

18 Claims, 52 Drawing Sheets

(56) References Cited

U.S. PATENT DOCUMENTS

| | | | |
|---|---|---|---|
| 4,261,390 A | 4/1981 | Belofsky | |
| 4,383,555 A | 5/1983 | Finley | |
| 4,553,545 A | 11/1985 | Maass et al. | |
| 4,576,532 A | 3/1986 | Hanson et al. | |
| 4,714,508 A | 12/1987 | Chivens et al. | |
| 4,733,665 A | 3/1988 | Palmaz | |
| 4,739,762 A | 4/1988 | Palmaz | |
| 4,740,207 A | 4/1988 | Kreamer | |
| 4,748,982 A | 6/1988 | Horzewski et al. | |
| 4,762,129 A | 8/1988 | Bonzel | |
| 4,776,337 A | 10/1988 | Palmaz | |
| 4,788,751 A * | 12/1988 | Shely et al. | 24/16 PB |
| 4,817,600 A | 4/1989 | Herms et al. | |
| 4,877,030 A | 10/1989 | Beck et al. | |
| 4,922,905 A | 5/1990 | Strecker | |
| 4,954,126 A | 9/1990 | Wallstén | |
| 4,980,449 A | 12/1990 | Kohn et al. | |
| 5,007,926 A | 4/1991 | Derbyshire | |
| 5,040,548 A | 8/1991 | Yock | |
| 5,059,211 A | 10/1991 | Stack et al. | |
| 5,061,273 A | 10/1991 | Yock | |
| 5,092,877 A | 3/1992 | Pinchuk | |
| 5,099,060 A | 3/1992 | Kohn et al. | |
| 5,108,416 A | 4/1992 | Ryan et al. | |
| 5,108,417 A | 4/1992 | Sawyer | |
| 5,140,094 A | 8/1992 | Kohn et al. | |
| 5,151,100 A | 9/1992 | Abele et al. | |
| 5,158,548 A | 10/1992 | Lau et al. | |
| 5,192,307 A | 3/1993 | Wall | |
| 5,194,570 A | 3/1993 | Kohn et al. | |
| 5,195,984 A | 3/1993 | Schatz | |
| 5,197,978 A | 3/1993 | Hess | |
| 5,198,507 A | 3/1993 | Kohn et al. | |
| 5,216,115 A | 6/1993 | Kohn et al. | |
| 5,230,349 A | 7/1993 | Langberg | |
| 5,232,445 A | 8/1993 | Bonzel | |
| 5,242,399 A | 9/1993 | Lau et al. | |
| 5,242,997 A | 9/1993 | Kohn et al. | |
| 5,264,537 A | 11/1993 | Kohn et al. | |
| 5,266,073 A | 11/1993 | Wall | |
| 5,282,823 A | 2/1994 | Schwartz et al. | |
| 5,300,085 A | 4/1994 | Yock | |
| 5,306,286 A | 4/1994 | Stack et al. | |
| 5,306,294 A | 4/1994 | Winston et al. | |
| 5,314,472 A | 5/1994 | Fontaine | |
| 5,317,077 A | 5/1994 | Kohn et al. | |
| 5,344,426 A | 9/1994 | Lau et al. | |
| 5,350,395 A | 9/1994 | Yock | |
| 5,397,355 A | 3/1995 | Marin et al. | |
| 5,402,554 A | 4/1995 | Oetiker | |
| 5,421,955 A | 6/1995 | Lau et al. | |
| 5,423,321 A | 6/1995 | Fontenot | |
| 5,423,885 A | 6/1995 | Williams | |
| 5,441,515 A | 8/1995 | Khosravi et al. | |
| 5,443,496 A | 8/1995 | Schwartz et al. | |
| 5,443,500 A | 8/1995 | Sigwart | |
| 5,445,646 A | 8/1995 | Euteneur et al. | |
| 5,449,382 A | 9/1995 | Dayton | |
| 5,451,233 A | 9/1995 | Yock | |
| 5,464,450 A | 11/1995 | Buscemi et al. | |
| 5,476,508 A | 12/1995 | Amstrup | |
| 5,484,449 A | 1/1996 | Amundson et al. | |
| 5,490,962 A | 2/1996 | Cima et al. | |
| 5,496,275 A | 3/1996 | Sirhan et al. | |
| 5,496,346 A | 3/1996 | Horzewski et al. | |
| 5,514,154 A | 5/1996 | Lau et al. | |
| 5,527,337 A | 6/1996 | Stack et al. | |
| 5,545,135 A | 8/1996 | Iacob et al. | |
| 5,545,138 A | 8/1996 | Fugoso et al. | |
| 5,549,556 A | 8/1996 | Ndondo-Lay et al. | |
| 5,549,662 A | 8/1996 | Fordenbacher | |
| 5,551,954 A | 9/1996 | Buscemi et al. | |
| 5,554,182 A | 9/1996 | Dinh et al. | |
| 5,556,413 A | 9/1996 | Lam | |
| 5,571,166 A | 11/1996 | Dinh et al. | |
| 5,575,816 A | 11/1996 | Rudnick et al. | |
| 5,578,075 A | 11/1996 | Dayton | |
| 5,587,507 A | 12/1996 | Kohn et al. | |
| 5,591,172 A | 1/1997 | Bachmann et al. | |
| 5,591,223 A | 1/1997 | Lock et al. | |
| 5,591,224 A | 1/1997 | Schwartz et al. | |
| 5,591,227 A | 1/1997 | Dinh et al. | |
| 5,599,352 A | 2/1997 | Dinh et al. | |
| 5,603,722 A | 2/1997 | Phan et al. | |
| 5,607,463 A | 3/1997 | Schwartz et al. | |
| 5,618,299 A | 4/1997 | Khosravi et al. | |
| 5,626,600 A | 5/1997 | Horzewski et al. | |
| 5,628,785 A | 5/1997 | Schwartz et al. | |
| 5,629,077 A | 5/1997 | Turnlund et al. | |
| 5,632,771 A | 5/1997 | Boatman et al. | |
| 5,643,312 A | 7/1997 | Fischell et al. | |
| 5,643,314 A | 7/1997 | Carpenter et al. | |
| 5,643,339 A | 7/1997 | Kavteladze et al. | |
| 5,649,977 A | 7/1997 | Campbell | |
| 5,651,174 A | 7/1997 | Schwartz et al. | |
| 5,658,995 A | 8/1997 | Kohn et al. | |
| 5,670,602 A | 9/1997 | Kohn et al. | |
| 5,681,345 A | 10/1997 | Euteneuer | |
| 5,697,967 A | 12/1997 | Dinh et al. | |
| 5,707,387 A | 1/1998 | Wijay | |
| 5,725,549 A * | 3/1998 | Lam | 623/1.15 |
| 5,733,328 A * | 3/1998 | Fordenbacher | 623/1.16 |
| 5,735,872 A * | 4/1998 | Carpenter et al. | 623/1.16 |
| 5,741,293 A * | 4/1998 | Wijay | 623/1.15 |
| 5,749,888 A | 5/1998 | Yock | |
| 5,755,708 A | 5/1998 | Segal | |
| 5,759,186 A | 6/1998 | Bachmann et al. | |
| 5,766,710 A | 6/1998 | Turnlund et al. | |
| 5,769,868 A | 6/1998 | Yock | |
| 5,797,951 A * | 8/1998 | Mueller | 606/198 |
| 5,799,384 A | 9/1998 | Schwartz et al. | |
| 5,800,393 A | 9/1998 | Sahota | |
| 5,800,456 A | 9/1998 | Maeda et al. | |
| 5,800,507 A | 9/1998 | Schwartz | |
| 5,833,707 A | 11/1998 | McIntyre et al. | |
| 5,836,965 A | 11/1998 | Jendersee et al. | |
| 5,843,175 A | 12/1998 | Frantzen | |
| 5,849,034 A | 12/1998 | Schwartz | |
| 5,851,217 A | 12/1998 | Wolff et al. | |
| 5,851,231 A | 12/1998 | Wolff et al. | |
| 5,855,600 A | 1/1999 | Alt | |
| 5,855,802 A | 1/1999 | Acciai et al. | |
| 5,868,747 A | 2/1999 | Ochoa et al. | |
| 5,876,419 A * | 3/1999 | Carpenter et al. | 623/1.16 |
| 5,893,840 A | 4/1999 | Hull et al. | |
| 5,906,639 A | 5/1999 | Rudnick et al. | |
| 5,910,816 A | 6/1999 | Fontenot et al. | |
| 5,921,952 A | 7/1999 | Desmond, III et al. | |
| 5,944,726 A | 8/1999 | Blaeser et al. | |
| 5,951,586 A | 9/1999 | Berg et al. | |
| 5,954,729 A | 9/1999 | Bachmann et al. | |
| 5,957,971 A | 9/1999 | Schwartz | |
| 5,957,975 A * | 9/1999 | Lafont et al. | 623/1.16 |
| 5,976,181 A | 11/1999 | Whelan et al. | |
| 5,984,963 A * | 11/1999 | Ryan et al. | 623/1.11 |
| 5,989,280 A | 11/1999 | Euteneur et al. | |
| 6,007,545 A | 12/1999 | Venturelli | |
| 6,015,387 A | 1/2000 | Schwartz et al. | |
| 6,019,779 A * | 2/2000 | Thorud et al. | 606/198 |
| 6,019,785 A | 2/2000 | Strecker | |
| 6,033,436 A * | 3/2000 | Steinke et al. | 623/1.15 |
| 6,036,715 A | 3/2000 | Yock | |
| 6,048,521 A | 4/2000 | Kohn et al. | |
| 6,059,825 A | 5/2000 | Hobbs et al. | |
| 6,063,111 A | 5/2000 | Hieshima et al. | |
| 6,066,169 A | 5/2000 | McGuinness | |
| 6,080,190 A | 6/2000 | Schwartz | |
| 6,080,191 A | 6/2000 | Summers | |
| 6,093,157 A | 7/2000 | Chandrasekaran | |
| 6,120,491 A | 9/2000 | Kohn et al. | |
| 6,123,721 A | 9/2000 | Jang | |
| 6,125,523 A | 10/2000 | Brown et al. | |
| 6,132,457 A | 10/2000 | Chobotov | |
| 6,156,062 A | 12/2000 | McGuiness | |

(56) References Cited

U.S. PATENT DOCUMENTS

| | | | |
|---|---|---|---|
| 6,159,239 A | 12/2000 | Greenhalgh | |
| 6,160,084 A | 12/2000 | Langer et al. | |
| 6,171,334 B1 | 1/2001 | Cox | |
| 6,174,328 B1 | 1/2001 | Cragg | |
| 6,179,878 B1 | 1/2001 | Duerig et al. | |
| 6,183,503 B1 | 2/2001 | Hart et al. | |
| 6,190,403 B1 | 2/2001 | Fishchell et al. | |
| 6,197,789 B1 | 3/2001 | Grainger | |
| 6,214,037 B1 | 4/2001 | Mitchell et al. | |
| 6,224,626 B1 * | 5/2001 | Steinke | 623/1.16 |
| 6,238,430 B1 | 5/2001 | Klumb et al. | |
| 6,258,117 B1 | 7/2001 | Camrud et al. | |
| 6,262,079 B1 | 7/2001 | Grainger et al. | |
| 6,264,624 B1 | 7/2001 | Desmond, III et al. | |
| 6,264,672 B1 | 7/2001 | Fisher | |
| 6,280,473 B1 | 8/2001 | Lemperle et al. | |
| 6,283,983 B1 | 9/2001 | Makower et al. | |
| 6,284,862 B1 | 9/2001 | Kohn et al. | |
| 6,287,329 B1 | 9/2001 | Duerig et al. | |
| 6,287,333 B1 | 9/2001 | Appling et al. | |
| 6,302,907 B1 | 10/2001 | Hijlkema | |
| 6,309,350 B1 | 10/2001 | Van Tassel et al. | |
| 6,319,277 B1 | 11/2001 | Rudnick et al. | |
| 6,319,492 B1 | 11/2001 | Kohn et al. | |
| 6,322,586 B1 | 11/2001 | Monroe et al. | |
| 6,350,277 B1 | 2/2002 | Kocur | |
| 6,359,102 B1 | 3/2002 | Kemnitzer et al. | |
| 6,361,558 B1 | 3/2002 | Hieshima et al. | |
| 6,375,677 B1 | 4/2002 | Penn et al. | |
| 6,383,211 B1 | 5/2002 | Staehle | |
| 6,388,043 B1 | 5/2002 | Langer et al. | |
| 6,391,032 B2 | 5/2002 | Blaeser et al. | |
| 6,406,490 B1 | 6/2002 | Roth | |
| 6,409,750 B1 | 6/2002 | Hyodoh et al. | |
| 6,409,751 B1 | 6/2002 | Hall et al. | |
| 6,409,752 B1 | 6/2002 | Boatman et al. | |
| 6,425,915 B1 | 7/2002 | Khosravi et al. | |
| 6,447,508 B1 | 9/2002 | Sharkey et al. | |
| 6,451,034 B1 | 9/2002 | Gifford, III et al. | |
| 6,458,152 B1 | 10/2002 | Khosravi et al. | |
| 6,475,477 B1 | 11/2002 | Kohn et al. | |
| 6,485,510 B1 | 11/2002 | Camrud et al. | |
| 6,488,700 B2 | 12/2002 | Klumb et al. | |
| 6,491,704 B2 | 12/2002 | Gifford, III et al. | |
| 6,491,705 B2 | 12/2002 | Gifford, III et al. | |
| 6,491,938 B2 | 12/2002 | Kunz et al. | |
| 6,497,671 B2 | 12/2002 | Ferrera et al. | |
| 6,527,791 B2 | 3/2003 | Fisher | |
| 6,530,940 B2 | 3/2003 | Fisher | |
| 6,530,958 B1 | 3/2003 | Cima et al. | |
| 6,562,021 B1 | 5/2003 | Derbin et al. | |
| 6,565,582 B2 | 5/2003 | Gifford, III et al. | |
| 6,565,596 B1 | 5/2003 | White et al. | |
| 6,569,191 B1 | 5/2003 | Hogan | |
| 6,569,441 B2 | 5/2003 | Kunz et al. | |
| 6,582,458 B1 | 6/2003 | White et al. | |
| 6,582,472 B2 | 6/2003 | Hart | |
| 6,585,760 B1 | 7/2003 | Fogarty | |
| 6,602,497 B1 | 8/2003 | Kohn et al. | |
| 6,607,551 B1 | 8/2003 | Sullivan et al. | |
| 6,610,086 B1 | 8/2003 | Kock et al. | |
| 6,613,073 B1 | 9/2003 | White et al. | |
| 6,620,356 B1 | 9/2003 | Wong et al. | |
| 6,623,491 B2 | 9/2003 | Thompson | |
| 6,623,518 B2 | 9/2003 | Thompson et al. | |
| 6,623,521 B2 * | 9/2003 | Steinke et al. | 623/1.16 |
| 6,645,143 B2 | 11/2003 | Van Tassel et al. | |
| 6,652,555 B1 | 11/2003 | Van Tassel et al. | |
| 6,659,105 B2 | 12/2003 | Burbank et al. | |
| 6,676,658 B2 | 1/2004 | Burbank et al. | |
| 6,682,541 B1 | 1/2004 | Gifford, III et al. | |
| 6,685,736 B1 | 2/2004 | White et al. | |
| 6,689,153 B1 | 2/2004 | Skiba | |
| 6,689,158 B1 | 2/2004 | White et al. | |
| 6,695,857 B2 | 2/2004 | Gifford, III et al. | |
| 6,699,257 B2 | 3/2004 | Gifford, III et al. | |
| 6,699,280 B2 | 3/2004 | Camrud et al. | |
| 6,702,846 B2 | 3/2004 | Mikus et al. | |
| 6,709,449 B2 | 3/2004 | Camrud et al. | |
| 6,720,402 B2 | 4/2004 | Langer et al. | |
| 6,736,838 B1 | 5/2004 | Richter | |
| 6,736,844 B1 | 5/2004 | Glatt et al. | |
| 6,746,477 B2 | 6/2004 | Moore | |
| 6,749,627 B2 | 6/2004 | Thompson et al. | |
| 6,786,922 B2 | 9/2004 | Schaeffer | |
| 6,790,221 B2 | 9/2004 | Monroe et al. | |
| 6,792,979 B2 | 9/2004 | Konya et al. | |
| 6,802,849 B2 | 10/2004 | Blaeser et al. | |
| 6,821,292 B2 | 11/2004 | Pazienza et al. | |
| 6,852,308 B2 | 2/2005 | Kohn et al. | |
| 6,869,143 B2 | 3/2005 | Secord | |
| 6,878,159 B2 | 4/2005 | Iwasaka et al. | |
| 6,878,162 B2 | 4/2005 | Bales et al. | |
| 6,916,868 B2 | 7/2005 | Kemnitzer et al. | |
| 6,929,709 B2 | 8/2005 | Smith | |
| 6,951,053 B2 * | 10/2005 | Padilla et al. | 29/557 |
| 6,962,604 B2 | 11/2005 | Hijlkema | |
| 6,964,680 B2 | 11/2005 | Shanley | |
| 6,974,472 B2 | 12/2005 | Hong et al. | |
| 6,974,475 B1 | 12/2005 | Wall | |
| 6,991,647 B2 | 1/2006 | Jadhav | |
| 7,041,126 B2 | 5/2006 | Shin et al. | |
| 7,056,493 B2 | 6/2006 | Kohn et al. | |
| 7,077,860 B2 | 7/2006 | Yan et al. | |
| 7,128,756 B2 | 10/2006 | Lowe et al. | |
| 7,141,063 B2 * | 11/2006 | White et al. | 623/1.15 |
| 7,175,653 B2 * | 2/2007 | Gaber | 623/1.15 |
| 7,229,473 B2 | 6/2007 | Falotico et al. | |
| 7,255,710 B2 * | 8/2007 | White et al. | 623/1.15 |
| 7,279,664 B2 | 10/2007 | Weber | |
| 7,329,277 B2 | 2/2008 | Addonizio et al. | |
| 7,476,232 B2 * | 1/2009 | Deal | 606/127 |
| 7,520,893 B2 | 4/2009 | Rivelli | |
| 7,553,377 B1 | 6/2009 | Chen et al. | |
| 7,556,644 B2 | 7/2009 | Burpee et al. | |
| 7,637,939 B2 | 12/2009 | Tischler | |
| 7,704,275 B2 | 4/2010 | Schmid et al. | |
| 7,722,662 B2 * | 5/2010 | Steinke et al. | 623/1.16 |
| 7,763,065 B2 * | 7/2010 | Schmid et al. | 623/1.15 |
| 7,763,067 B2 | 7/2010 | Bales et al. | |
| 7,766,960 B2 | 8/2010 | Alexander et al. | |
| 7,780,721 B2 | 8/2010 | Bales et al. | |
| 7,812,290 B2 | 10/2010 | Weber | |
| 7,846,198 B2 | 12/2010 | Hogendijk | |
| 7,947,071 B2 * | 5/2011 | Schmid et al. | 623/1.22 |
| 7,988,721 B2 * | 8/2011 | Morris et al. | 623/1.16 |
| 8,172,894 B2 | 5/2012 | Schmid et al. | |
| 8,277,500 B2 * | 10/2012 | Schmid et al. | 623/1.15 |
| 8,292,944 B2 * | 10/2012 | Schmid et al. | 623/1.15 |
| 8,460,363 B2 * | 6/2013 | Morris et al. | 623/1.16 |
| 8,512,394 B2 * | 8/2013 | Schmid et al. | 623/1.15 |
| 8,523,936 B2 * | 9/2013 | Schmid et al. | 623/1.22 |
| 8,540,762 B2 | 9/2013 | Schmid et al. | |
| 8,545,547 B2 * | 10/2013 | Schmid et al. | 623/1.22 |
| 8,617,235 B2 * | 12/2013 | Schmid et al. | 623/1.16 |
| 2001/0010015 A1 | 7/2001 | Hijlkema | |
| 2001/0020173 A1 | 9/2001 | Klumb et al. | |
| 2001/0029378 A1 | 10/2001 | Blaeser et al. | |
| 2001/0044651 A1 * | 11/2001 | Steinke et al. | 623/1.16 |
| 2002/0010504 A1 | 1/2002 | Alt et al. | |
| 2002/0040238 A1 | 4/2002 | Rudnick et al. | |
| 2002/0052641 A1 | 5/2002 | Monroe et al. | |
| 2002/0072656 A1 | 6/2002 | Van Tassel et al. | |
| 2002/0077693 A1 | 6/2002 | Barclay et al. | |
| 2002/0082682 A1 | 6/2002 | Barclay et al. | |
| 2002/0095204 A1 | 7/2002 | Thompson et al. | |
| 2002/0099431 A1 | 7/2002 | Armstrong et al. | |
| 2002/0111669 A1 | 8/2002 | Pazienza et al. | |
| 2002/0116044 A1 * | 8/2002 | Cottone et al. | 623/1.2 |
| 2002/0120322 A1 | 8/2002 | Thompson et al. | |
| 2002/0120323 A1 | 8/2002 | Thompson et al. | |
| 2002/0123791 A1 | 9/2002 | Harrison | |
| 2002/0138081 A1 | 9/2002 | Blaeser et al. | |
| 2002/0138126 A1 | 9/2002 | Camrud et al. | |

(56) References Cited

U.S. PATENT DOCUMENTS

| | | |
|---|---|---|
| 2002/0147489 A1 | 10/2002 | Hong et al. |
| 2002/0151967 A1 | 10/2002 | Mikus et al. |
| 2002/0156456 A1 | 10/2002 | Fisher |
| 2002/0156457 A1 | 10/2002 | Fisher |
| 2002/0193870 A1 | 12/2002 | Jang |
| 2003/0045923 A1 | 3/2003 | Bashiri |
| 2003/0069633 A1 | 4/2003 | Richter et al. |
| 2003/0074043 A1 | 4/2003 | Thompson |
| 2003/0078649 A1 | 4/2003 | Camrud et al. |
| 2003/0120334 A1 | 6/2003 | Gerberding |
| 2003/0176914 A1 | 9/2003 | Rabkin et al. |
| 2003/0199969 A1* | 10/2003 | Steinke et al. ........... 623/1.16 |
| 2003/0208262 A1 | 11/2003 | Gaber |
| 2003/0211135 A1 | 11/2003 | Greenhalgh et al. |
| 2003/0212451 A1 | 11/2003 | Cox et al. |
| 2003/0220682 A1 | 11/2003 | Kujawski |
| 2004/0024446 A1 | 2/2004 | Smith |
| 2004/0044401 A1 | 3/2004 | Bales et al. |
| 2004/0054400 A1 | 3/2004 | Granada |
| 2004/0062788 A1 | 4/2004 | Richter |
| 2004/0068316 A1 | 4/2004 | Schaeffer |
| 2004/0086458 A1 | 5/2004 | Kohn et al. |
| 2004/0086462 A1 | 5/2004 | Kohn et al. |
| 2004/0093073 A1 | 5/2004 | Lowe et al. |
| 2004/0093076 A1 | 5/2004 | White et al. |
| 2004/0097959 A1 | 5/2004 | Thompson |
| 2004/0106971 A1 | 6/2004 | Schwartz et al. |
| 2004/0106977 A1 | 6/2004 | Sullivan et al. |
| 2004/0133260 A1 | 7/2004 | Schwartz et al. |
| 2004/0143319 A1 | 7/2004 | Schwartz et al. |
| 2004/0167616 A1 | 8/2004 | Camrud et al. |
| 2004/0186551 A1 | 9/2004 | Kao et al. |
| 2004/0186556 A1 | 9/2004 | Hogendijk et al. |
| 2004/0186557 A1 | 9/2004 | Gambale et al. |
| 2004/0191175 A1 | 9/2004 | Kohn et al. |
| 2004/0193251 A1 | 9/2004 | Rudnick et al. |
| 2004/0224003 A1 | 11/2004 | Schultz |
| 2004/0236401 A1 | 11/2004 | Shin et al. |
| 2004/0243217 A1 | 12/2004 | Andersen et al. |
| 2004/0243218 A1 | 12/2004 | Schaeffer |
| 2005/0038497 A1 | 2/2005 | Neuendorf et al. |
| 2005/0038503 A1 | 2/2005 | Greenhalgh et al. |
| 2005/0106119 A1 | 5/2005 | Brandom et al. |
| 2005/0123481 A1 | 6/2005 | Kohn et al. |
| 2005/0165203 A1 | 7/2005 | Kohn et al. |
| 2005/0203615 A1 | 9/2005 | Forster et al. |
| 2005/0216076 A1 | 9/2005 | Kveen et al. |
| 2005/0246010 A1* | 11/2005 | Alexander et al. ........... 623/1.12 |
| 2006/0020324 A1* | 1/2006 | Schmid et al. ........... 623/1.16 |
| 2006/0024266 A1 | 2/2006 | Brandom et al. |
| 2006/0026815 A1* | 2/2006 | Padilla et al. ........... 29/558 |
| 2006/0030934 A1* | 2/2006 | Hogendijk et al. ........... 623/1.22 |
| 2006/0034769 A1 | 2/2006 | Kohn et al. |
| 2006/0079955 A1* | 4/2006 | Brown ........... 623/1.22 |
| 2006/0115449 A1 | 6/2006 | Pacetti |
| 2006/0136041 A1* | 6/2006 | Schmid et al. ........... 623/1.16 |
| 2006/0182779 A1 | 8/2006 | Brandom et al. |
| 2006/0204440 A1 | 9/2006 | Kohn et al. |
| 2007/0010870 A1 | 1/2007 | Alt et al. |
| 2007/0032854 A1* | 2/2007 | Schmid et al. ........... 623/1.15 |
| 2007/0032857 A1* | 2/2007 | Schmid et al. ........... 623/1.16 |
| 2007/0142901 A1* | 6/2007 | Steinke et al. ........... 623/1.16 |
| 2007/0250148 A1 | 10/2007 | Perry et al. |
| 2007/0270939 A1 | 11/2007 | Hood et al. |
| 2008/0046066 A1 | 2/2008 | Jenson et al. |
| 2008/0051868 A1 | 2/2008 | Cottone et al. |
| 2008/0051873 A1 | 2/2008 | Cottone et al. |
| 2008/0051874 A1 | 2/2008 | Cottone et al. |
| 2008/0051875 A1 | 2/2008 | Cottone et al. |
| 2008/0071355 A1 | 3/2008 | Weber |
| 2008/0103584 A1 | 5/2008 | Su et al. |
| 2008/0114391 A1 | 5/2008 | Dieck et al. |
| 2008/0195190 A1 | 8/2008 | Bland et al. |
| 2008/0221664 A1 | 9/2008 | Bales et al. |
| 2008/0221665 A1 | 9/2008 | Peckham et al. |
| 2008/0262599 A1 | 10/2008 | Caro et al. |
| 2008/0269869 A1* | 10/2008 | Cho ........... 623/1.12 |
| 2008/0288050 A1 | 11/2008 | Addonizio et al. |
| 2009/0030501 A1* | 1/2009 | Morris et al. ........... 623/1.15 |
| 2009/0143853 A1* | 6/2009 | Morris et al. ........... 623/1.16 |
| 2009/0187239 A1 | 7/2009 | Goto |
| 2010/0004725 A1 | 1/2010 | Zipse et al. |
| 2010/0042203 A1 | 2/2010 | Cottone et al. |
| 2010/0114297 A1 | 5/2010 | Calisse |
| 2010/0131048 A1* | 5/2010 | Schmid et al. ........... 623/1.22 |
| 2010/0256735 A1* | 10/2010 | Morales, Jr. ........... 623/1.15 |
| 2010/0280593 A1 | 11/2010 | Richter |
| 2010/0286759 A1 | 11/2010 | Taylor et al. |
| 2010/0292773 A1* | 11/2010 | Schmid et al. ........... 623/1.11 |
| 2010/0324662 A1 | 12/2010 | Addonizio et al. |
| 2011/0172759 A1* | 7/2011 | Schmid et al. ........... 623/1.15 |
| 2011/0245909 A1* | 10/2011 | Schmid et al. ........... 623/1.16 |
| 2011/0251674 A1* | 10/2011 | Schmid et al. ........... 623/1.16 |
| 2011/0282434 A1* | 11/2011 | Morris et al. ........... 623/1.16 |
| 2012/0221097 A1* | 8/2012 | Schmid et al. ........... 623/1.16 |
| 2013/0253631 A1* | 9/2013 | Schmid et al. ........... 623/1.15 |
| 2014/0025159 A1* | 1/2014 | Morris et al. ........... 623/1.16 |
| 2014/0067042 A1* | 3/2014 | Schmid et al. ........... 623/1.16 |
| 2014/0094897 A1* | 4/2014 | Schmid et al. ........... 623/1.15 |
| 2014/0277375 A1 | 9/2014 | Weier et al. |

FOREIGN PATENT DOCUMENTS

| | | |
|---|---|---|
| CA | 2573886 C | 9/2014 |
| CN | 102245127 B | 6/2014 |
| EP | 0712614 | 5/1996 |
| EP | 0756853 | 2/1997 |
| EP | 2315558 | 5/2011 |
| JP | 07-000531 | 1/1995 |
| JP | 08-196641 | 8/1996 |
| JP | 08-336598 | 12/1996 |
| JP | 9-313617 | 12/1997 |
| JP | 2007-185363 | 7/2007 |
| WO | WO 90/14046 A1 | 11/1990 |
| WO | WO 94/21196 A2 | 9/1994 |
| WO | WO 94/21196 A3 | 2/1995 |
| WO | WO 96/14030 A1 | 5/1996 |
| WO | WO 97/07751 A1 | 3/1997 |
| WO | WO 97/42911 A1 | 11/1997 |
| WO | WO 98/22045 | 5/1998 |
| WO | WO 98/22073 A2 | 5/1998 |
| WO | WO 98/41169 A1 | 9/1998 |
| WO | WO 98/22073 A3 | 2/1999 |
| WO | WO 99/08740 A1 | 2/1999 |
| WO | WO 99/15106 A1 | 4/1999 |
| WO | WO 99/40874 A1 | 8/1999 |
| WO | WO 99/65421 A2 | 12/1999 |
| WO | WO 99/65421 A3 | 1/2000 |
| WO | WO 00/09195 A1 | 2/2000 |
| WO | WO 00/10623 | 3/2000 |
| WO | WO 00/30565 A1 | 6/2000 |
| WO | WO 00/59405 A1 | 10/2000 |
| WO | WO 00/62708 A1 | 10/2000 |
| WO | WO 00/62708 C2 | 10/2000 |
| WO | WO 00/71058 A1 | 11/2000 |
| WO | WO 01/24735 A1 | 4/2001 |
| WO | WO 01/35864 A1 | 5/2001 |
| WO | WO 01/51114 A2 | 7/2001 |
| WO | WO 01/70298 A2 | 9/2001 |
| WO | WO 01/87180 A2 | 11/2001 |
| WO | WO 01/87180 A3 | 11/2001 |
| WO | WO 01/51114 A3 | 1/2002 |
| WO | WO 01/70298 A3 | 2/2002 |
| WO | WO 02/047582 A2 | 6/2002 |
| WO | WO 02/053204 A2 | 7/2002 |
| WO | WO 02/053204 A3 | 7/2002 |
| WO | WO 02/054990 A2 | 7/2002 |
| WO | WO 02/047582 A3 | 10/2002 |
| WO | WO 02/054990 A3 | 11/2002 |
| WO | WO 03/022178 A1 | 3/2003 |
| WO | WO 03/047464 A2 | 6/2003 |
| WO | WO 03/057076 A1 | 7/2003 |
| WO | WO 03/047464 A3 | 9/2003 |
| WO | WO 03/047464 C2 | 11/2003 |

(56) References Cited

FOREIGN PATENT DOCUMENTS

| WO | WO 03/094798 A1 | 11/2003 |
|---|---|---|
| WO | WO 03/099161 A2 | 12/2003 |
| WO | WO 03/099161 A3 | 12/2003 |
| WO | WO 2004/019820 A1 | 3/2004 |
| WO | WO 2004/026112 A2 | 4/2004 |
| WO | WO 2004/032803 A1 | 4/2004 |
| WO | WO 2004/026112 C2 | 6/2004 |
| WO | WO 2004/026112 A3 | 10/2004 |
| WO | WO 2004/087015 | 10/2004 |
| WO | WO 2004/096340 A1 | 11/2004 |
| WO | WO 2004/110312 A1 | 12/2004 |
| WO | WO 2006/010636 A1 | 2/2006 |
| WO | WO 2006/014596 A1 | 2/2006 |
| WO | WO 2006/014699 A1 | 2/2006 |
| WO | WO 2006/020616 A1 | 2/2006 |
| WO | WO 2006/107608 A1 | 10/2006 |
| WO | WO 2007/016409 A1 | 2/2007 |
| WO | WO 2007/084444 A2 | 7/2007 |
| WO | WO 2010/022005 A1 | 2/2010 |
| WO | WO 2010/042879 A2 | 4/2010 |
| WO | WO 2011/127452 A1 | 10/2011 |
| WO | WO 2014/159337 A1 | 10/2014 |
| WO | WO 2014/176361 A1 | 10/2014 |

OTHER PUBLICATIONS

International Search Report and Opinion, mailed Apr. 2, 2010 in related International application No. PCT/US2009/060256, 9 pp.
Office Action received in corresponding Australian Application No. 2009303347, dated Jan. 24, 2013, 4 pages.
Office Action received in corresponding Australian Application No. 2013204977, dated May 7, 2013, 2 pages.
Search Report received in corresponding Chinese Application No. 200980149447.2, dated Aug. 14, 2013, 4 pages.
Office Action received in corresponding Chinese Application No. 200980149447.2, mailed Aug. 23, 2013, 7 pages.
Office Action received in corresponding Japanese Application No. 2011-531230, dated Jul. 4, 2013, 9 pages.
Asahara, T. "Local delivery of vascular endothelial growth factor accelerates reendothelialization and attenuates intimal hyperplasia in balloon-insured rate carotid artery," Circulation 91: 2793-2801, 1995.
Autieri, M.V. et al. "Antisense oligonucleotides to the p65 subunit of NF-Kb inhibit human vascualr smooth muscle cell adherence and proliferation and prevent neointima formation in rat carotid arteries," Biochemical and Biophysical Research Communications 213: 827-836, 1995.
Brauner, R. "Controlled periadverntitial administration of verapamil inhibits neointimal smooth muscle cell proliferation and ameliorates vasomotor abnormalities in experimental vein bypass grafts," The Journal of Thoracic and Cardiovascular Surgery 114: 53-63, 1997.
Carmeliet, P. et al. "Inhibitory role of plasminogen activator inhibitor-1 in arterial wound healing and neointima formation," Circulation 96: 3180-3191, 1997.
Epstein, S.E. et al. "Cytotoxic effects of a recombinant chimeric toxin on rapidly proliferating vascular smooth muscle cells," Circulation 84: 778-787, 1991.
Hu, Y. "Inhibition of neointima hyperplasia of mouse vein grafts by locally applied suramin," Circulation 100: 861-868, 1999.
Kurisu, Y. et al. "Protective effect of beraprost sodium, a stable prostacyclin analogue, on cardiac allograft vasculopathy in rats," Hiroshima Journal of Medical Science 56: 11-19, 1997.
Morishita, R. et al. "Novel in vitro gene transfer method for study of local modulators in vascular smooth muscle cells," Hypertension 21: 894-899, 1993.
Nerem, R.M. et al. "Tissue engineering and the vascular system, synthetic biodegradable polymer scaffolds," pp. 164-185, 1997.
Von Der Leyen, H.E. et al. "Gene therapy neointimal vascular lesion: in vivo transfer of endothelial cell nitric oxide synthase gene," PNAS USA 92:1137-1141, 1995.
Yasukawa, H. "Inhibition of intimal hyperplasia after balloon injury by antibodies to intercellular adhesion molecule-1 and lymphocyte function, Associated antigen-1," Circulation 95: 1515-1522, 1997.
Balcon, R. et al., Recommendations on stent manufacture, implantation and utilization, European Heart Journal, Oct. 1997, vol. 18, pp. 1536-1547.
Charles, Roger et al., Ceramide-Coated Balloon Catheters Limit Neointimal Hyperplasia After Stretch Injury in Carotid Arteries, Circulation Research, 2000; 87; pp. 282-288.
Coroneos, Emmanuel et al., Differential Regulation of Sphingomyelinase and Ceramidase Activities by Growth Factors and Cytokines, The Journal of Biological Chemistry, Oct. 6, 1995, vol. 270, No. 40, pp. 23305-23309.
Jacobs, Leila S. et al., Sphingolipids as mediators of effects of platelet-derived growth factor in vascular smooth muscle cells, Am J Physiol (American Physiological Society), 1993, pp. C740-C747.
Tanguay, Jean Francois et al., Current Status of Biodegradable Stents, Cardiology Clinics, Contemporary Interventional Techniques, Nov. 1994, vol. 12, No. 4, pp. 699-713, W.B. Saunders Company.
Nikol, S. et al., Molecular biology and post-angioplasty restenosis, Atherosclerosis, 1996; 123, pp. 17-31.
Phillips, Paul S. MD, et al., The Stenter's Notebook, 1998, (entire book), Physicians' Press, Birmingham, Michigan.
Ratner, Buddy D. et al., Biomaterials Science, An Introduction to Materials in Medicine, 2nd Edition, 2004, (entire book), Elsevier Academic Press.
Serruys, Patrick W. et al., Handbook of Coronary Stents, Fourth Edition, 2002, (entire book), Martin Dunitz Ltd.
Atala, Anthony et al., Synthetic Biodegradable Polymer Scaffolds, 1997, (entire book), Birkhauser Boston.

* cited by examiner

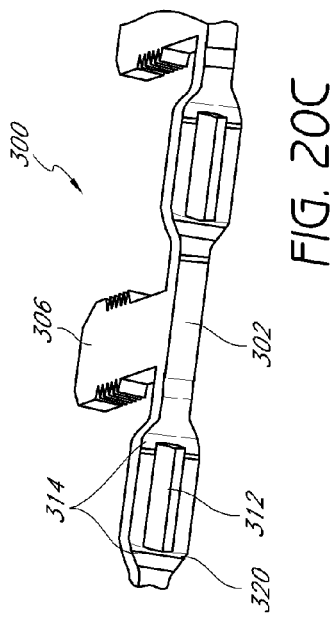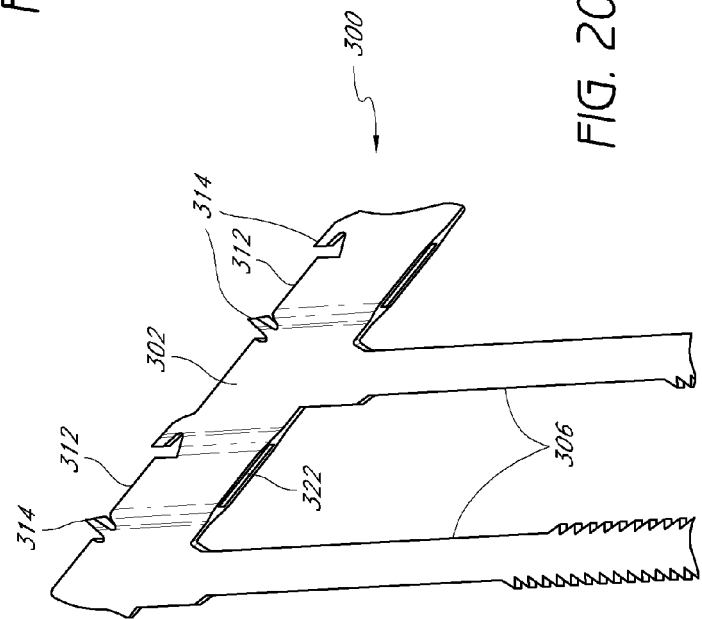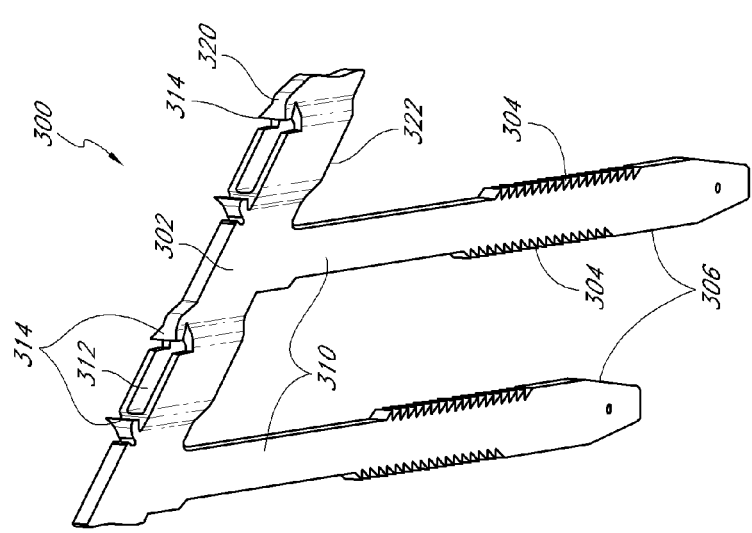

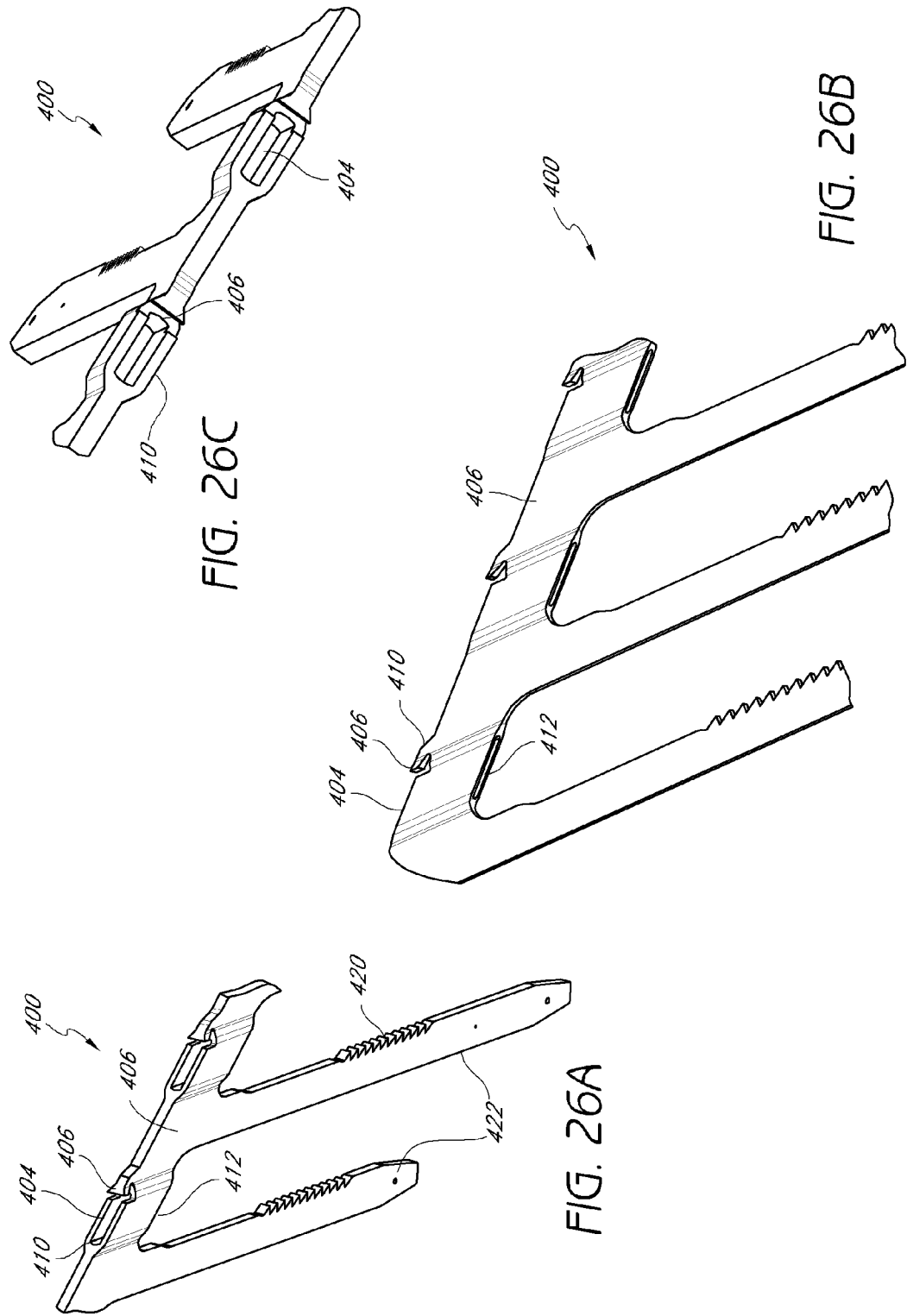

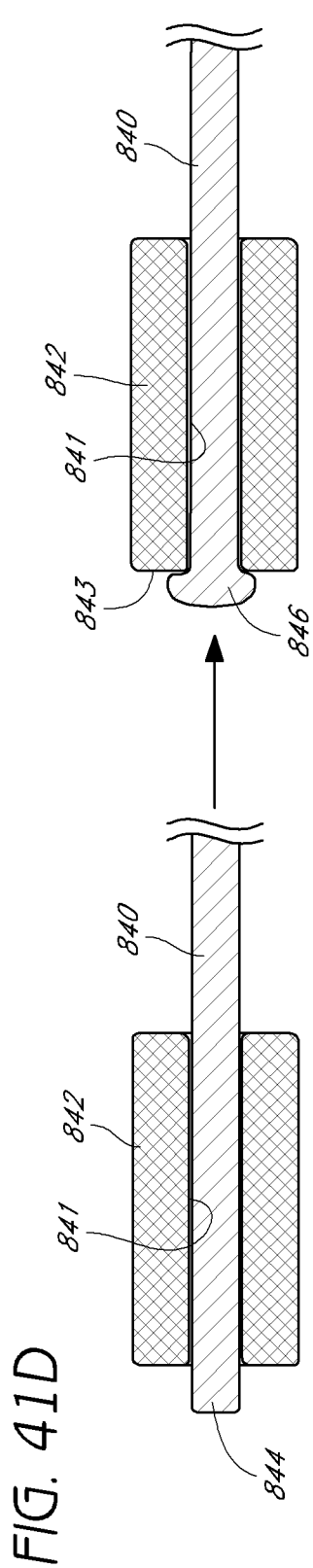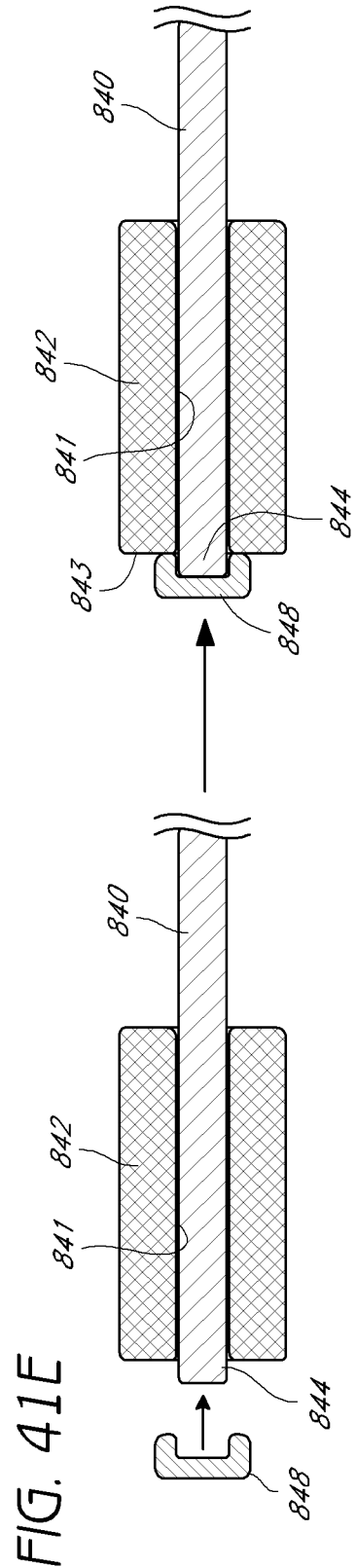

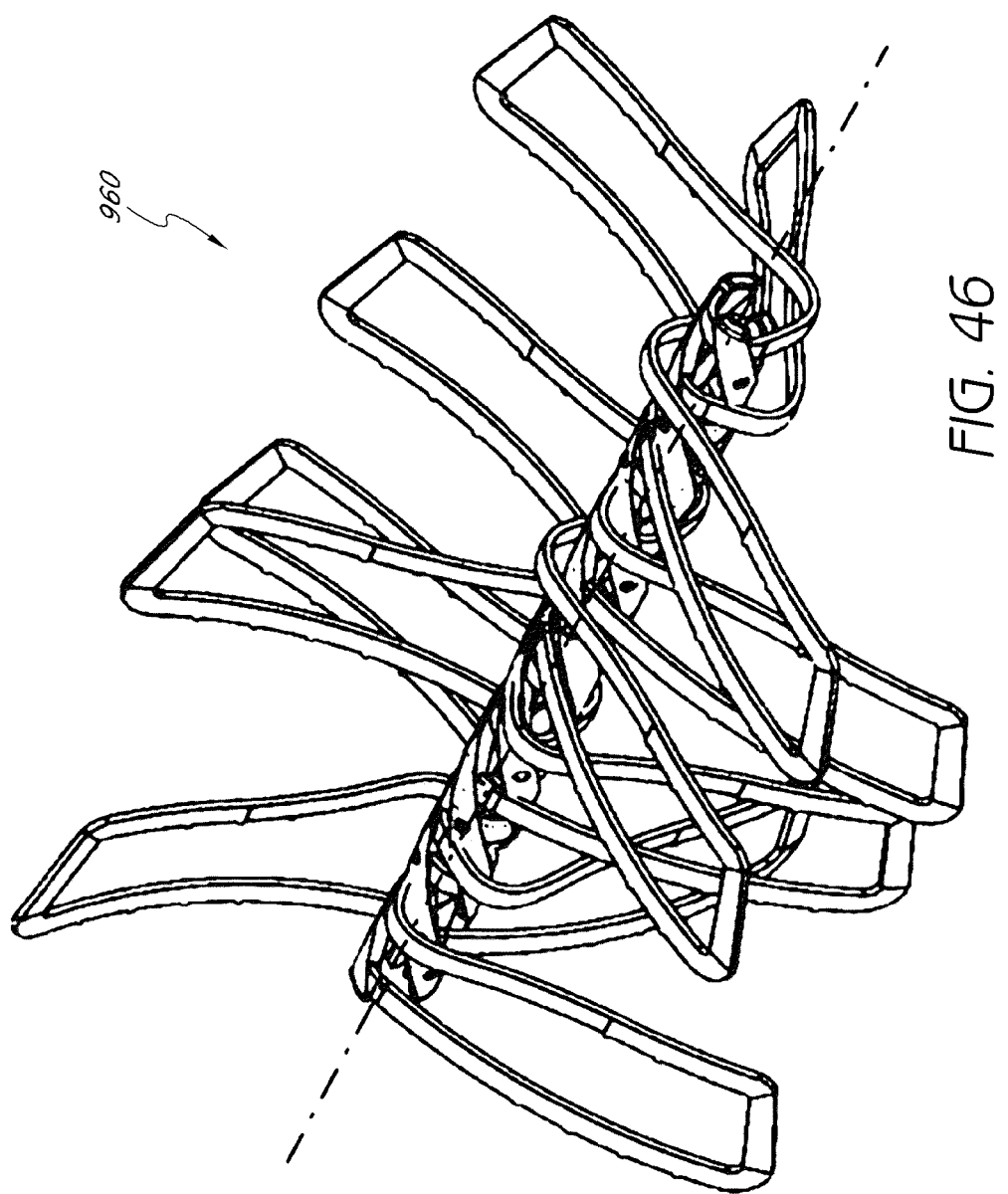

EXPANDABLE SLIDE AND LOCK STENT

CROSS-REFERENCE TO RELATED APPLICATIONS

This application is a continuation of U.S. application Ser. No. 13/113,894, filed on May 23, 2011, which is a continuation of U.S. application Ser. No. 12/577,018, filed on Oct. 9, 2009, which claims the benefit of U.S. Provisional Application Nos. 61/104,683, filed Oct. 10, 2008, and 61/231,972, filed Aug. 6, 2009, the entireties of which are incorporated herein by reference.

BACKGROUND

1. Field of the Inventions

The present inventions relate generally to expandable medical implants for maintaining support of a body lumen, and more specifically, to a uniform stent having improved mechanical and post-deployment dynamic capabilities.

2. Description of the Related Art

Various embodiments of vascular implants; such as stents, thrombus filters, and heart valves, are used in their various embodiments for medical applications. Of these vascular devices, one of the leading candidates as a stent device and structural component is the radially expandable and slidably engaged stent as disclosed in commonly owned U.S. Pat. No. 6,033,436; U.S. Pat. No. 6,224,626; and U.S. Pat. No. 6,623,521; the disclosures of which are hereby incorporated by reference. These radially expandable and slidably engaged stents offer the strength of prior expandable stents with the added improvements of low cross-section deliverability, less bulk material thickness, high resolution fitting, and shape customization such as hourglass-shape configurations.

Other radially expandable and slidably engaged stents; such as those disclosed in U.S. Pat. No. 5,797,951; U.S. Pat. No. 5,549,662; and U.S. Pat. No. 5,733,328; further describe the state of the art and their disclosures are hereby incorporated by reference.

Although promising candidates for use as implantable devices and device components, these known radially expandable and slidably engaged stents have mechanical and vasodynamic limitations of which the inventors of the present application set out to address. These limitations can be characterized as deployment related limitations, and limitations related to vasodynamic capabilities.

Deployment related limitations of prior art stents are herein described. Intravascular space; especially that of a patient in need of a vascular implant, is generally inconsistent and varies upon the individual with respect to curvature, plaque buildup and other luminary obstructions.

Procedures are available to physicians such as balloon angioplasty, which aid in the reduction of plaque prior to stenting. However, even after such procedures, vascular characteristics remain patient delineated and largely inconsistent. Inconsistencies in vascular characteristics; such as the interference due to a luminary occlusion, require flexibility, distribution of material strength, and vascular adaptability of devices to be implanted.

SUMMARY

In accordance with at least one of the embodiments disclosed herein is the realization that a vascular implant may experience a number of mechanical limitations related to delivery. For example, some portions of the vasculature are curved or substantially non-cylindrical. These portions of the vasculature have proven difficult to deploy stent devices. Sometimes, the curvature of the vessel can cause a deployed stent to fold, especially in stents with insufficient flexibility in the design. Curved vessels further increase the potential for hinging and denting as described in further detail below.

A vascular implant may also experience a number of countering forces post-deployment. Some of these countering forces are a result of what is herein referred to as vasodynamics; the resulting movements, constrictions and contortions of the vasculature. Of these countering forces is crush force, caused by post-expansion elastic recoil of the vessel.

Additionally, some stents experience an occlusion-derived impaction force; a point force derived from the impact of a luminary occlusion directly onto the device; such a luminary occlusion can be plaque or a thrombus. Other countering forces such as dilation, and contortion, are to be discussed in further detail below.

The inventors of the present application have recognized a problem with known radially expandable and slidably engaged stents, the problem herein referred to as "hinging." Many slidably-engaged expandable stents possess a common limitation where the engagements are generally longitudinally aligned, thereby inherently creating an alignment of failure points. A failure point is a weakness in a stent design, usually a point where two parts are joined together in a less than permanent fashion such as an engagement between slidably-engaged radial modules. When an amount of radial pressure is exerted on the expanded stent, the stent tends to buckle or fold at the failure point. A series of failure points that are longitudinally aligned can act as a perforation in the material and cause a substantial weakness and propensity for hinging.

Another plaque-related problem is herein referred to as "denting." Denting is caused by an inherent device pattern weakness where a vaso-occlusion can drive a portion of at least one stent module into the luminary space, thereby substantially enhancing the effect of the vaso-occlusion. Such an occlusion or dent can lead to collection of thrombus or flow distortions which are problematic and can increase stenosis.

Vascular plaque is typically non-uniform and often forms in a bulky occlusion, such an occlusion can place added stress on the stent via a point force, and increase the risk of hinging or denting.

The inventors of the present application have recognized that denting can significantly dampen or interfere with vasodynamics, and therefore may cause an increase in realized stenosis. Furthermore, denting may not be immediately apparent to the implanting physician where a polymer stent is adapted for increased ductility over time.

Many devices are fabricated from a biodegradable polymer which may become substantially more ductile and flexible with the progression of time up to a point of water absorption equilibrium. As water is absorbed, the polymer material becomes bendable or ductile. Differing polymer compositions will have a varied rate of moisture absorption. The inventors of the present application recognized the benefits of controlled water absorption into the polymer material such as a reduced propensity for microfissures. Furthermore, the inventors of the present application recognized detriments such as a propensity for denting where the design pattern provides unsupported adjacent components. The likelihood of denting occurrences is increased for stent patterns lacking the support of a structural backbone, especially when there are unsecured corners or other points having a propensity for weakness. Often, the extent to which denting occurs cannot be determined until several hours after the deployment procedure, hence the importance to minimize the potential for denting and improving the design pattern of the target device.

In accordance with at least one of the embodiments disclosed herein, the inventors of the present application have recognized that a mechanically-improved stent design will overcome these limitations set out above, and will further set out to increase adaptability to the dynamics of the vasculature.

Many prior art stent embodiments are designed around crush force and maintaining patency of a luminary space. Although patency of the lumen is of primary concern, there are other factors which must be addressed in an effort to go beyond functionality, but rather to move toward the successful treatment and healing of a vessel.

The vasculature is a dynamic system. Although it is difficult to quantify, the vasculature may experience a number of dynamic movements at any given moment in time. Of these is a wave-like dilation, which presents variability in the interior diameter of the vessel at a given location. Dilation can occur from a change in blood pressure or other change in the circulation. Additionally, portions of the vasculature can experience a contortion or twist like motion in addition to dilation. Where there is plaque or a luminary occlusion, the vasculature can experience a resistance to these natural movements. Such a resistance can cause the adjacent tissue to undergo a cytotic response, such as the division of cells, or intravascular cell growth known as neointimal growth. Neointimal growth is a new or thickened layer of arterial intima formed especially on a prosthesis or in atherosclerosis by migration and proliferation of cells.

Clinical data generally shows that stent implants stimulate neointimal growth in the vessel immediately subsequent to implantation. Neointimal growth is acceptable up to a point where blood pressure is substantially increased or where the lumen is obstructed and blood can no longer efficiently pass.

It is thought that resistance to vasodynamics, among other things, can dramatically increase stenosis surrounding an implanted vascular device. Therefore, it is critical to understand the dynamics of the vasculature and to design a stent capable of maintaining patency of the lumen while promoting the motions associated with vasodynamics such as periodic dilation and contortion. A stent designed to incorporate the dynamics of the vasculature can better serve to treat and ultimately heal the vessel.

Generally, neointimal growth surrounds and encompasses the implanted stent, leaving the stent to reside substantially within the new vessel wall. It is in this state that stent mechanics are critical in minimizing further stenosis.

Although stents can be made of generally any biocompatible material, there is a movement toward the use of stents fabricated from a biodegradable and bioresorbable polymer. Biodegradation is the structural decomposition of a polymer, often occurring as bulk erosion, surface erosion, or a combination thereof. Bioresorption includes the cellular metabolism of the degraded polymer. The inventors of the present application have set out to design a stent capable of utilizing the degradation and resorption properties of the polymer to enhance the healing and treatment of the vessel.

In some embodiments, there is provided a stent having a uniform distribution of failure points. This uniform distribution can minimize, if not eliminate the potential for hinging and denting.

In other embodiments, there is provided a stent having a rotationally flexible backbone capable of adaption to vasodynamic movements, thereby minimizing stenosis of the vasculature.

In yet other embodiments, there is provided a stent design capable of being efficiently encapsulated with neointimal growth, such that initial degradation of the stent material will transform the stent into a rotationally flexible and vaso-adaptive support within the new vessel wall.

In summary, there remains a need for an improved radially expandable and slidably engaged luminary support structure: one that uniformly distributes failure points about the device so as to prevent hinging, one that provides adequate support to components so as to prevent denting, one that embraces the effects of water absorption so as to prevent micro fissures while providing effective stenting to the vasculature, one that is capable of restoring vaso-motion to the treated vessel upon neo-intima containment, and one that embraces known properties of radially expandable and slidably engaged support structures such as low cross-section deliverability, less bulk material thickness, high resolution fitting, and shape customization such as hourglass-shape configurations.

An expandable stent is disclosed in accordance with an embodiment of the present inventions. The stent can provide radial support to maintain patency of a lumen, a flexible vaso-adaptive backbone structure, and a uniform circumferential distribution of slidable engagements.

Aside from radial expansion and an ability to maintain patency of the body lumen, the present disclosure provides solutions to the aforementioned problems of hinging, denting and restriction of vasodynamic movements.

In accordance with at least one of the embodiments disclosed herein is the realization that a propensity for hinging is increased in stent designs having an alignment of engagement means that are substantially parallel with respect to the longitudinal axis of the stent. Further, in accordance with at least one of the embodiments disclosed herein is the realization that a potential for denting can be minimized by incorporating a support backbone to secure the extremities and corners of those members or features associated with maintaining patency of the lumen, herein elongate members.

Additionally, in accordance with at least one of the embodiments disclosed herein is the realization of the importance of providing a stent having flexibility sufficient to promote and adapt to natural vasodynamic movements while maintaining patency of the lumen. Further, stenosis can be minimized by improving the flexibility of the stent so as to provide adaption to vasodynamic movements such as wave-like dilation and contortion movements.

In an embodiment, the stent can comprise a tubular member having a circumference which is expandable between at least a first collapsed diameter and at least a second expanded diameter. The expandable stent can provide minimally invasive delivery capabilities, and can be adapted for delivery and deployment via a catheter, especially a balloon expandable catheter.

The tubular member can be generally configured from at least two slidably engaged radial elements. The slidably engaged radial elements can be configured to collectively define the circumference of the tubular member.

In an embodiment, an expandable slide and lock polymer stent is provided that can comprise first and second helical backbones, first and second sets of elongate members, and first and second crossbars. The first and second helical backbones can each comprise a plurality of slots. In this regard, each slot can have an axis extending in a circumferential direction, and the first and second helical backbones can extend in a helical path along an axis of the stent.

The first set of elongate members can define proximal and distal ends. The proximal ends of the first set of elongate members can be coupled to the first helical backbone with the first set of elongate members extending in a circumferential direction from the first helical backbone through the slots of the second helical backbone. The first set of elongate members can be axially offset from each other. The first crossbar can couple the distal ends of the first set of elongate members.

The second set of elongate members can define proximal and distal ends. The proximal ends of the second set of elongate members can be coupled to the second helical backbone and extending in a circumferential direction from the second helical backbone through the slots of the first helical backbone. The second set of elongate members can be axially offset from each other and from the first set of elongate members. Further, the second crossbar can couple the distal ends of the second set of elongate members.

In some embodiments, the first and second helical backbones and the first and second sets of elongate members and the first and second crossbars can form first and second radial elements that can be interconnected to collectively form a tubular member having a circumference which is expandable between a collapsed diameter and an expanded diameter. The first and second radial elements can be configured to provide one-way expansion from the collapsed diameter to the expanded diameter.

In some optional implementations, the first crossbar can have a recessed portion and the second crossbar can have a recessed portion. The recessed portion of the first crossbar can be configured such that one of the elongate members of the second set can be at least partially disposed in the recessed portion of the first crossbar. The recessed portion of the second crossbar can be configured to at least partially receive one of the elongate members of the first set therein. Further, the recessed portions of the first and second crossbars can be recessed radially inwardly relative to the respective ones of the elongate members of the second and first sets. Additionally, it is contemplated the recessed portions of the first and second crossbars can be configured to be recessed radially outwardly relative to the respective ones of the elongate members of the second and first sets.

In optional embodiments, the stent can be configured such that the first set of elongate members is monolithically formed with the first helical backbone such that the coupling of the first crossbar to the distal ends of the first set of elongate members forms a tail-bond. Further, the second set of elongate members can be monolithically formed with the second helical backbone such that the coupling of the second crossbar to the distal ends of the second set of elongate members forms a tail-bond.

Alternatively, the first set of elongate members can be formed separately from the first helical backbone such that the coupling of the first set of elongate members with the first helical backbone forms one of a core-bond and a mid-rail bond. Further, the second set of elongate members can be formed separately from the second helical backbone such that the coupling of the second set of elongate members with the second helical backbone forms one of a core-bond and a mid-rail bond. Accordingly, in such embodiments, the first crossbar can be monolithically formed with the first set of elongate members. Furthermore, the second crossbar can be monolithically formed with the second set of elongate members.

In addition, in some embodiments, the elongate members can comprise one or more teeth for engaging respective slots to provide one-way expansion of the stent. Further, the stent can be configured such that each slot comprises a central passage and at least one internal recess for engaging the teeth of the elongate member. In this regard, it is contemplated that a method can be provided for forming such an embodiment. The method can comprise forming the central passage as a first through hole in the backbone in a circumferential direction of stent, and forming the at least one internal recess as a second through hole in the backbone in a direction transverse to the circumferential direction of the central passage such that the first and second through holes partially overlap.

In accordance with another embodiment, the stent can optionally be configured such that the stent can provide structural properties comparable to a metal stent while providing bioresorbability. For example, the stent can comprise a plurality of radial elements interconnected to collectively form a tubular member. Each radial element can comprising a continuously-slotted helical backbone and a plurality of elongate rails that is offset from slots of the continuously-slotted helical backbone. The rails can extend from the helical backbone in a circumferential direction at an angle that is greater than or less than 90°. For example, the helix angle can be between about 30° to about 80°. However, the helix angle can be between about 40° to about 60°. Further, a first radial element can be interconnected with a second radial element with the elongate rails of the first radial element being received into the slots of the continuously slotted backbone of the second radial element.

Moreover, embodiments of the stent can be formed using one or more radial elements. In this regard, an embodiment of such a radial element can be formed to comprise a helical backbone and a plurality of rib elements.

In some embodiments, the backbone can be a continuously-slotted helical backbone member having a plurality of engagement slots and a plurality of connection slots. For example, the engagement slots can be spaced between consecutive connection slots along the backbone. Further, each helical backbone member can generally define a longitudinal axis.

The elongate rib elements can be configured to have having proximal and distal portions. The proximal portion can be interconnectable with one or more connections slots of the continuously slotted backbone member. Further, each rib element can be positionable generally circumferentially about the longitudinal axis and have a fixed engagement at a non-perpendicular angle with respect to the helical backbone member.

Accordingly, in such embodiments, the plurality of elongate rib elements can be arranged to interconnect with at least one other helical backbone member of another radial element so as to form an expandable tubular skeleton. The elongate rib elements can provide a one-way slidable engagement with the engagement slots of the helical backbone member of the other radial element. Further, the tubular skeleton can be configured to expand radially between a collapsed diameter and an expanded diameter upon circumferential motion of the slidable engagement of the rib elements to the helical backbone members. Furthermore, the slidable engagement can include a mechanism that is operative to restrain collapse of the tubular skeleton from the expanded diameter towards the collapsed diameter.

In some optional embodiments of the radial element, the helical backbone can comprise portions of reduced thickness for allowing at least partial nesting of an elongate rib element thereagainst. Further, the radial element can be configured such that a pair of elongate rib elements are interconnected at their distal portions by a crossbar. Furthermore, the crossbar can comprise an offset portion configured to at least partially receive an elongate rib of an adjacent radial element for reducing a passing profile of a stent formed using a plurality of radial elements.

According to yet other optional embodiments, the radial element can be configured such that the helical backbone extends helically at a generally fixed radius and helix angle relative to the longitudinal axis. In this regard, the engagement slot can comprises a through slot that defines a central axis extending in a generally circumferential direction and within a plane that is perpendicular to the longitudinal axis of the radial element, and the central axis of the engagement slot can extend at a non-perpendicular angle relative to the helical backbone.

In one further embodiment, an expandable stent is disclosed, comprising a plurality of radial elements interconnected to form a tubular member, each radial element comprising a helical support member comprising a plurality of slots and a plurality of circumferential rails, wherein a first radial element is interconnected with a second radial element, such that the circumferential rails of the first radial element are received into the slots of the helical support member of the second radial element, wherein the expandable stent is made from a bioresorbable polymer and exhibits structural properties comparable to a metal stent.

BRIEF DESCRIPTION OF THE DRAWINGS

The abovementioned and other features of the inventions disclosed herein are described below with reference to the drawings of the embodiments. The illustrated embodiments are intended to illustrate, but not to limit the inventions. The drawings contain the following figures:

FIG. 20A is a magnified perspective of a top portion of the radial element of FIG. 19, illustrating the features of the flexible backbone, captive slots, and elongate members.

FIG. 20B is a magnified perspective of a bottom portion of the radial element of FIG. 19, illustrating the features of the flexible backbone, captive slots, and elongate members.

FIG. 20C is a magnified perspective of a top portion of the radial element of FIG. 19, illustrating the features of the flexible backbone, captive slots, and elongate members.

FIG. 26A is a magnified perspective of a top portion of the radial element of FIG. 25, illustrating features of a flexible backbone, captive slots, and elongate members.

FIG. 26B is a magnified perspective of a bottom portion of the radial element of FIG. 25, illustrating the features of the flexible backbone, captive slots, and elongate members.

FIG. 26C is a magnified perspective of a top portion of the radial element of FIG. 25, illustrating the features of the flexible backbone, captive slots, and elongate members.

FIGS. 41A-E are cross-sectional side views of various embodiments of rail and backbone attachment mechanisms of a stent assembly for fixing a proximal end of a rail to a backbone member.

FIG. 46 is a perspective view of a stent assembly illustrating a backbone assembly in a compacted configuration and showing the manner of wrapping extended elongate members around a backbone helix, according to an embodiment.

DETAILED DESCRIPTION

Figure 1:
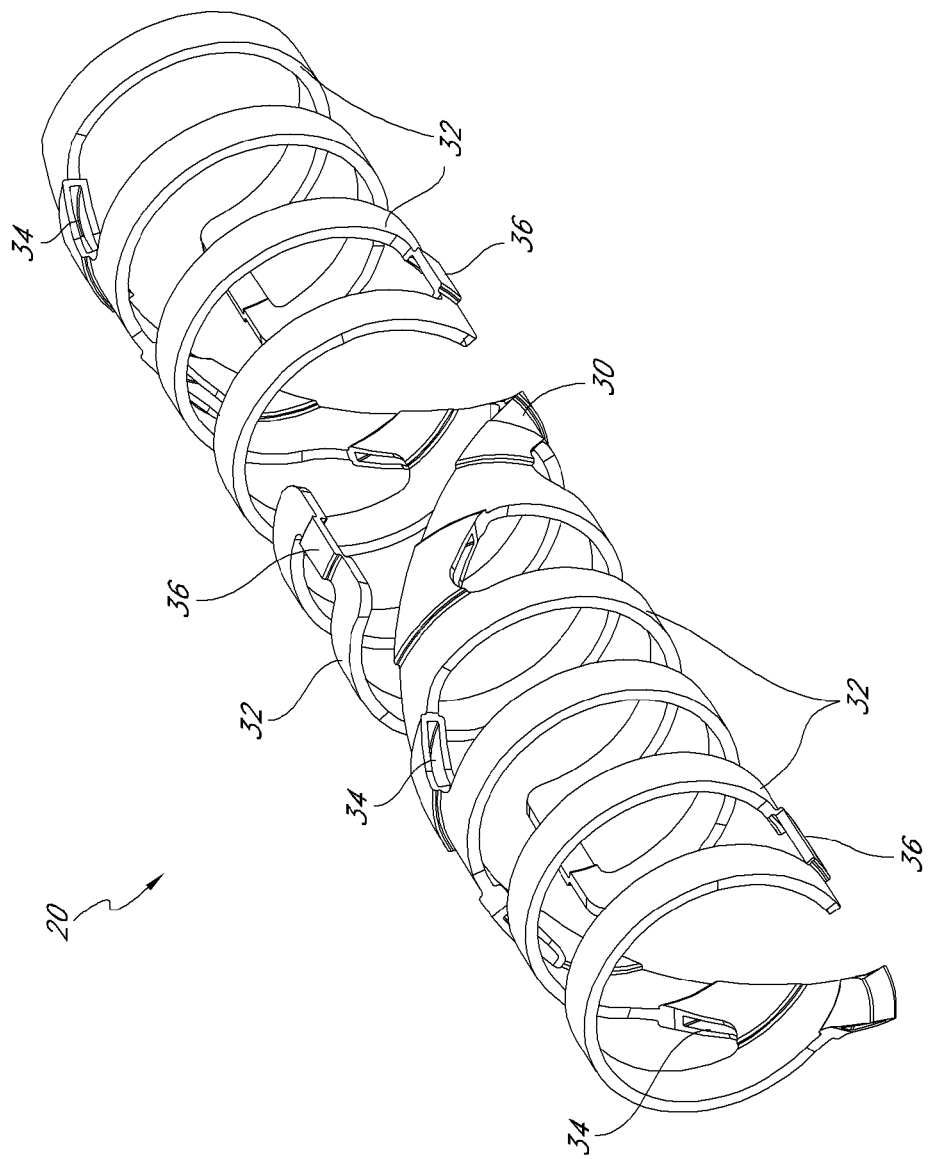
FIG. 1 is a perspective view of a single radial element of a stent in accordance with an embodiment.

As will be discussed herein, embodiments of the stent summarized above and defined by the enumerated claims may be better understood by referring to the following detailed description, which should be read in conjunction with the accompanying drawings. This detailed description of embodiments, set out below to enable one having skill in the art to build and use one particular implementation, is not intended to limit the enumerated claims, but to serve as a particular example thereof.

While the description sets forth various embodiments in specific detail, it will be appreciated that the description is illustrative only and should not be construed in any way as limiting the same. Furthermore, various applications of the embodiments, and modifications thereto, which can occur to those who are skilled in the art, are also encompassed by the general concepts described herein.

The term "stent" is used herein to designate embodiments for placement in (1) vascular body lumens (i.e., arteries and/or veins) such as coronary vessels, neurovascular vessels and peripheral vessels for instance renal, iliac, femoral, popliteal, subclavian and carotid; and in (2) nonvascular body lumens such as those treated currently i.e., digestive lumens (e.g., gastrointestinal, duodenum and esophagus, biliary ducts), respiratory lumens (e.g., tracheal and bronchial), and urinary lumens (e.g., urethra); (3) additionally such embodiments can be useful in lumens of other body systems such as the reproductive, endocrine, hematopoietic and/or the integumentary, musculoskeletal/orthopedic and nervous systems (including auditory and ophthalmic applications); and, (4) finally, stent embodiments can be useful for expanding an obstructed lumen and for inducing an obstruction (e.g., as in the case of aneurysms).

The term "stent" is further used herein to designate embodiments such as; support structures for maintaining patency of a body lumen; support structures for anchoring thrombus filters and heart valves; as well as support structures for the distribution and delivery of therapeutic agents as well as other devices.

In the following description of embodiments, the term "stent" can be used interchangeably with the term "prosthesis" and should be interpreted broadly to include a wide variety of devices configured for supporting a segment of a body passageway. Furthermore, it should be understood that the term "body passageway" encompasses any lumen or duct within a body, such as those described herein.

Still further, it should be understood that the term "shape-memory material" is a broad term that can include a variety of known shape memory alloys, such as nickel-titanium alloys, as well as any other materials that return to a previously defined shape after undergoing substantial plastic deformation.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon can be regulated for expanding the stent to a particular desired diameter. Accordingly, balloon expandable stents can be used in applications wherein precise placement and sizing are important. Balloon expandable stents can be used for direct stenting applications, where there is no pre-dilation of the vessel before stent deployment, or in prosthetic applications, following a pre-dilation procedure (e.g., balloon angioplasty). During direct stenting, the expansion of the inflatable balloon dilates the vessel while also expanding the stent.

The stent can be fabricated from at least one or more materials. These materials include metals, polymers, composites, and shape-memory materials. In another optional embodiment, the stent further can comprise a tubular member formed from a biocompatible and preferably, bioresorbable polymer, such as those disclosed in co-pending U.S. application Ser. No. 10/952,202, the disclosure of which is incorporated herein in its entirety by reference. It is also understood that the various polymer formulae employed can include homopolymers and heteropolymers, which can include stereoisomerism, composites, filled materials, etc. Homopolymer is used herein to designate a polymer comprised of all the same type of monomers. Heteropolymer is used herein to designate a polymer comprised of two or more different types of monomer which is also called a co-polymer. A heteropolymer or co-polymer can be of a kind known as block, random and alternating. Further with respect to the presentation of the various polymer formulae, products according to embodiments can be comprised of a homopolymer, heteropolymer and/or a blend of such polymers.

The term "bioresorbable" is used herein to designate polymers that undergo biodegradation (through the action of water and/or enzymes to be chemically degraded) and at least some of the degradation products can be eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term "inherently radiopaque" is used herein to designate polymer that is intrinsically radiopaque due to the covalent bonding of halogen species to the polymer. Accordingly, the term does encompass a polymer which is simply blended with a halogenated species or other radiopacifying agents such as metals and their complexes.

In another optional variation, the stent further can comprise an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that can be natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, can include virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" can include 1) "biomolecule", as used herein, encompassing a biologically active peptide, protein, carbohydrate, vitamin, lipid, or nucleic acid produced by and purified from naturally occurring or recombinant organisms, tissues or cell lines or synthetic analogs of such molecules, including antibodies, growth factors, interleukins and interferons; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent can also include vitamin or mineral substances or other natural elements.

In some embodiments, the design features of the axially or circumferentially offset elements can be varied to customize the functional features of strength, compliance, radius of curvature at deployment and expansion ratio. In some embodiments, the stent can comprise a resorbable material and vanishes when its job is done. In some embodiments, the stent serves as a therapeutic delivery platform.

Some aspects are also disclosed in co-pending U.S. patent application Ser. Nos. 11/016,269, 60/601,526, 10/655,338, 10/773,756, and 10/897,235, the disclosures of each of which are incorporated herein in their entirety by reference thereto.

Some features and arrangements of embodiments of stents are disclosed in U.S. Pat. Nos. 6,033,436, 6,224,626, and 6,623,521, each issued to Steinke, the disclosures of each of which are hereby incorporated in their entirety by reference thereto.

Advantageously, the stent design elements and interlocks can be varied to customize the functional features of strength, compliance, radius of curvature at deployment and expansion ratio. In some embodiments, the stent can comprise a resorbable material and vanishes when its job is done. In some embodiments, the stent serves as a delivery platform for therapeutic agents such as pharmaceutical compounds or biological materials.

Some embodiments relate to a radially expandable stent used to open, or to expand a targeted area in a body lumen. Some embodiments relate to a radially expandable stent used as a drug delivery platform to treat vascular conditions. In some embodiments, the assembled stent can comprise a tubular member having a length in the longitudinal axis and a diameter in the radial axis, of appropriate size to be inserted into the body lumen. The length and diameter of the tubular member can vary considerably for deployment in different selected target lumens depending on the number and configuration of the structural components, described below.

The tubular member in accordance with some embodiments can have a "clear through-lumen," which can be defined as having no structural elements protruding into the lumen in either the collapsed or expanded diameters. Further, the tubular member can have smooth marginal edges to minimize the trauma of edge effects. The tubular member can be preferably thin-walled and flexible (e.g., less than about 0.01 Newtons force/millimeter deflection) to facilitate delivery to small vessels and through tortuous vasculature.

In optional embodiments, the wall thickness can be about 0.0001 inches to about 0.0250 inches, and more preferably about 0.0010 to about 0.0100 inches. However, the wall thickness depends, at least in part, on the selected material. For example, the thickness can be less than about 0.0080 inches for plastic and degradable materials and can be less than about 0.0020 inches for metal materials. More particularly, for a 3.00 mm stent application, when a plastic material is used, the thickness can be preferably in the range of about 0.0020 inches to about 0.0100 inches. The thin walled design can also minimize blood turbulence and thus risk of thrombosis. The thin profile of the deployed tubular member in accordance with some embodiments also facilitates more rapid endothelialization of the stent. The above thickness ranges have been found to provide superior characteristics through all aspects of the device including assembly and deployment. However, it will be appreciated that the above thickness ranges should not be limiting with respect to the scope of the embodiments and that the present teachings can be applied to devices having dimensions not discussed herein.

In accordance with the principles of the inventions disclosed herein, the geometry of the stent may be generally described as a tubular member. In accordance with these various features, the slidably engaged expandable stent can include at least two slidably engaged radial elements defining a circumference of the tubular member.

In some embodiments, the stent can comprise one or more helical backbone assemblies. The helical backbone assembly of the embodiments described herein provides a high degree of longitudinal structural integrity combined with longitudinal and rotational flexibility, both in the compacted and deployed configurations. The array of elongate members, elongate rails, or rail elements that extend from the backbones can interlock with other backbones to form an interwoven circumferential surface that provides crush strength and radial stiffness without unduly inhibiting longitudinal or rotational flexibility. The generally circumferential alignment of the elongate members allows the elongate members to engage each other and the backbone in a configuration which provides "hoop-strength" without direct coupling, thus providing a substantial increase overall longitudinal "beam" stiffness. In certain embodiments, the stent structure may be described as expandable tubular "skeleton" assembly defined by the systematic movable interconnection of a plurality helical "backbone members" via a plurality of circumferentially arranged rail or "rib" elements.

Further, the backbones of many of the backbone assemblies disclosed herein provide a continuously-slotted backbone. In other words, embodiments of the backbone can be configured to comprise a series of slots formed along the backbone for facilitating interconnection of the backbone assembly with another backbone assembly. The continuous slotting of the backbone can be advantageous by reducing the tendency for hinging, kinking, and buckling of the stent. Further, due to the unique helical backbone structure and slide-and-lock expansion mechanism of embodiments disclosed herein, a continuously-slotted backbone can also contribute to superior flexion and crush strength of the stent.

Accordingly, various embodiments described herein can provide for a polymeric stent that exhibits advantageous structural properties that are comparable to those of a metal stent. For example, research has illustrated that the helical backbone construction, paired with the slide-and-lock interconnection of radial elements, can be used in a polymer stent such that the advantages of bioresorbability and superior structural stiffness and strength (similar to that of a metal stent) can be realized. This significant advance in stent technology allows other preferable materials—not just metals—to be used in a stent to achieve desirable material properties, while ensuring that the necessary structural properties of the stent are also achieved.

The slidably engaged radial elements can be configured for unidirectional slidable movement so as to permit the radial expansion of the tubular member. In an embodiment, the stent can define a first collapsed diameter, and a second expanded diameter. The slidably engaged expandable stent is adapted to be expandable between at least the first collapsed diameter and at least the second expanded diameter.

In some embodiments, the slidably engaged expandable stent is configured with two radial modules, each radial module being slidably engaged and configured for unidirectional expansive movement. Each radial module can include a backbone, a first elongate member and a second elongate member. In some embodiments, the elongate members are annular elongate members; ring-like members elongated from the backbone. The elongate members are slidably engaged with slots and configured for unidirectional slidable movement.

The slidably engaged expandable stent in some embodiments has a plurality of annular elongate members, including a first elongate member and a second elongate member. These annular elongate members are substantially commonly oriented with respect to the backbone. Additionally, the second elongate member is axially or circumferentially offset with respect to the first elongate member.

The axially or circumferential offsetting of elongate members allows a distribution of slidable engagements. Such a distribution of slidable engagements is said to render the stent uniform with respect to mechanical failure points; as the slidable engagements are the weakest mechanical points in the design. Slidable engagements are herein defined as the engagement means between two slidably engaged radial modules. In some embodiments, the slidable engagements are defined by the interlocking of slots and contained rails of the slidably engaged elongate members.

The slots can further comprise a locking member. A locking member can be a tooth, a deflectable tooth, or a stop. In some embodiments, the slots comprise a number of stops inside the surface or cavity of the slot. In another embodiment, the slots comprise at least one tooth adjacent to the entry side of the slot.

Additionally, the elongate members can be configured to comprise at least one conjugate locking member. A conjugate locking member is essentially a component designed to engage with the locking member. In some embodiments, a conjugate locking member is adapted to fit be engaged by the locking member. In one embodiment, the conjugate locking member is one of a tooth, a deflectable tooth, or a stop. A locking member and a conjugate locking member define an engagement means whereby the radial modules are slidably engaged.

A conjugate locking member can be located on any part of the stent; however in some embodiments, the conjugate locking member is located on the rail of an elongate member. Each elongate member has at least one radial surface and at least two axial sides. Axial sides are substantially perpendicular to the longitudinal axis of the elongate member. In some embodiments, a plurality of conjugate locking members can be distributed on both axial sides of the rail. In one embodiment, the conjugate locking members on both axial sides of the elongate member can be substantially aligned in a mirrored distribution. In another embodiment, the conjugate locking members can be substantially mirrored but offset by a vertical distance with respect to the opposite axial side. Axial locking members can be axially nested and substantially prevented from protruding into the vessel wall, thereby preventing undesired agitation which can cause stenosis.

Further, conjugate locking members can be spaced apart by a defined distance. The conjugate locking members on one axial side can be offset with respect to the conjugate locking members of the second axial side. Such an offsetting of conjugate locking members can provide a higher resolution for stent diameter customization.

In another embodiment, the stent comprises a backbone adapted to substantially coil about the tubular member. A substantially coiled backbone; or otherwise herein referred to as a helical backbone or a flexible backbone, gives rotational flexibility to the stent design. Rotational flexibility is an important improvement which will allow the stent to adapt to vasodynamic movements. A substantially coiled backbone can be an elongate backbone configured to coil about the tubular member, or alternatively can be a stair-step pattern, a wave-like pattern, or any other pattern which is substantially configured in a helical orientation about the tubular member.

In an embodiment, a plurality of radial elements each comprising a backbone can be configured into a tubular member having a plurality of substantially coiled backbones. A flexible backbone is herein defined as any backbone of a radial element which is configured to substantially coil about the tubular member.

Additionally, a flexible backbone can comprise a flexible link in the backbone, such as a spring link. Or alternatively, the flexible backbone can be made of an elastomeric polymer material sufficient to promote adaption to vasodynamic movements. Elastomeric polymers are defined in the art, however for illustrative purposes examples can include polycaprolactone, polydioxanone, and polyhexamethylcarbonate.

EXAMPLES

FIGS. 1-8 show conceptual views of embodiments of an expandable vascular device, prosthesis or stent in assembled and exploded orientations. The stent can be operative to move via translation and/or slide and lock movement. FIGS. 1-8 are intended to be conceptual in nature. Thus, the embodiments shown in FIGS. 1-8, as well as other embodiments of the stents disclosed herein, can incorporate structural elements, structural members, slide and lock mechanisms and other features that are discussed in further detail below with reference to further drawings as described in further detail herein.

Referring to FIGS. 1-5, a stent 10 is provided that can have a tubular form. These figures illustrate that the stent 10 can have a wall comprising a plurality of generally helically arranged linked radial elements or modules 20, 22. The stent 10 can have a through lumen which, along with the stent itself, can be expandable from a first diameter ($D_{lumen-collapsed}$ or $D_{inner-collapsed}$) to a second diameter ($D_{lumen-expanded}$ or $D_{inner-expanded}$). The stent 10 and/or the lumen can have a generally longitudinal axis.

FIG. 1 illustrates an embodiment of the radial element 20 in a tubular configured orientation. The radial element 20 comprises a flexible backbone or backbone member 30 configured in a helical alignment with respect to the longitudinal axis. The flexible backbone 30 is described as being configured in a coiled orientation about the longitudinal axis of the stent 10. The radial element 20 can also comprise at least one elongate member, elongate rail, or rail element 32 extending from the backbone 30. In many embodiments, such as that illustrated in FIG. 1, a plurality of elongate members can be provided along the backbone in an radially offset configuration. However, the elongate members can also be circumferentially offset from each other. Additionally, it is contemplated that the backbone 30 can comprise a plurality of slots 34. For example, the slots 34 can be configured as "fully captive" or "semi-captive" slots, as described further below.

As will be described herein, various embodiments of the stent component or radial element can comprise a slot. The slot can be configured as a completely or fully captive slot or as a substantially or semi-captive slot. It is contemplated that when referring to a completely or fully captive slot, the completely or fully captive slot can be an opening, cut, slit, incision, etc. in a material such that an element disposed through the slot is captured on the lateral, upper, and lower sides thereof, thus only allowing one degree of motion, such as movement or translation in a posterior-anterior direction through the slot. In other words, a completely or fully captive slot can restrict motion of the element in all directions except for anterior (forward) and posterior (rearward) sliding or translating motion (permitting only one degree of motion) into and out of the slot.

A substantially or semi-captive slot can be configured to allow two or more degrees of motion. When compared to a completely or fully captive slot, a semi-captive slot can provide at least one additional degree of freedom of movement of the element disposed therethrough. For example, as noted above, a fully captive slot can capture an element on the lateral, upper, and lower sides thereof, thus only allowing the element to move or slide in a posterior-anterior direction through the slot. In contrast, a semi-captive slot may provide movement in a posterior-anterior direction, as well as a rotational motion or translational movement in a lateral or upper or lower direction (in other words, two or more degrees of movement). For example, a semi-captive slot can surround an element on three sides and allow the element to be move in a posterior-anterior direction and to be slide or translate in a lateral or upper or lower direction relative to the slot.

It is also noted that the embodiments shown in FIGS. 1-29B and 38-58 illustrate that the backbones can be formed as a "continuously-slotted" backbone. In other words, embodiments of the backbone can be configured to comprise a series of slots formed along the backbone for facilitating interconnection of the backbone assembly with another backbone assembly. The slots can be for interconnection with elongate members of adjacent radial elements or for connecting proximal ends of elongate members to the backbone (such as in a core-bonded stent). The continuous slotting of the backbone can be advantageous in that it can reduce the tendency for hinging, kinking, and buckling of the stent. Further, due to the unique helical backbone structure and slide-and-lock expansion mechanism of embodiments disclosed herein, a continuously-slotted backbone can also contribute to superior flexion and crush strength of the stent.

In accordance with some embodiments, the stent 10 can be formed from a sheet of material that is formed to create one or more stent components, such as the radial elements 20, 22, that can be wound or curled upon itself to create a cylindrical or tubular member. While a single radial element may be used to form the stent in some embodiments, greater radial expansion is possible using two or more radial elements.

As illustrated in the FIGS. 2-5, the radial elements 20, 22 of the stent 10 can comprise a generally helical backbone 30, 40 and a plurality of elongate members 32, 42 extending therefrom. Additionally, it is contemplated that the helical backbone 30, 40 can comprise a plurality of fully captive slots 34, 44. In some embodiments, the fully captive slots 34, 44 can be configured to capture a respective elongate member 32, 42 and capture the elongate member 32, 42 on all sides within a plane that is perpendicular to a plane of the sheet of material. In other words, the fully captive slot 34, 44 can be formed to receive an elongate member extending in a generally circumferential direction about a perimeter of the stent or tubular member.

Additionally, it is contemplated that at least a portion of a stent component can comprise one or more thicknesses and/or comprise one or more radially offset portions. In this regard, the radial elements can comprise one or more sections that overlap or nest with each other. Such a configuration can provide for a more compact stent with a reduced profile in either or both of an expanded and/or collapsed diameter.

For example, at least one of the radial elements 20, 22 can comprise one or more thicknesses and/or comprise one or more crossbars, bridge portions, or radially offset portions 36, 46. The crossbars, bridge portions, or offset portions 36, 46 can be formed between distal ends of the elongate members 32, 42 and thereby interconnect distal ends of a pair of elongate members 32, 42. Further, the crossbars 36, 46 can define a thickness that is different from the thickness of the elongate members 32, 42. For example, an outer surface of the elongate members 32, 42 can be in a common plane with an outer surface of the crossbars 36, 46 with an inner surface of the elongate members 32, 42 being in a plane that is offset from a plane of an inner surface of the crossbars 36, 46. However, the crossbars 36, 46 can also define inner and outer surfaces that are both generally radially offset from inner and outer surfaces of the elongate members 32, 42.

Figure 5:
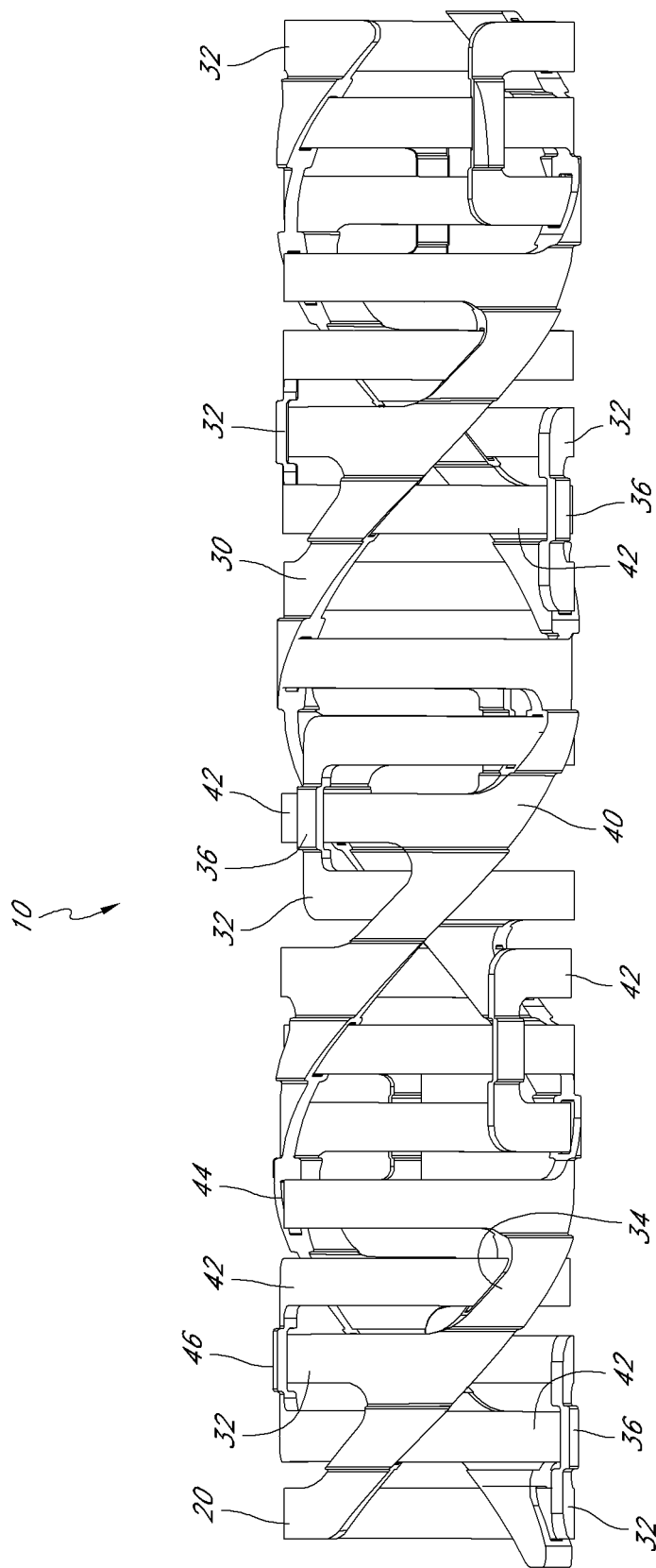
FIG. 5 is a side view of the stent of FIG. 2 in the assembled, expanded state.

As shown in FIG. 5, when the stent 10 is curled into a tubular member, the thickness of a given portion can be reduced or offset. In this regard, the crossbar or overlapping element 36 of the radial element 20 can be configured such that a portion of a stent component, such as the elongate member 42 of the radial element 22 is generally nested against the crossbar 36. Thus, the overlapping of the radial elements 20, 22 does not substantially protrude in a radial direction. In other embodiments, either or both of the radial elements or stent components can comprise portions having reduced thicknesses such that overlap of the radial elements or stent components does not substantially increase the cross-sectional or passing profile of the stent in a radial direction.

In some embodiments having a plurality of radially overlapping stent components or radial elements, the stent components or radial elements can comprise reduced thicknesses or offset portions that are configured to at least partially receive a plurality of stent components or radial elements. For example, a backbone of a first radial element can be configured with a slot for accommodating at least a portion of a second radial element and a reduced thickness or offset portion for accommodating at least a portion of a third radial element.

In such embodiments, the passing or outer profile of the stent can be minimized in order to facilitate placement and deployment of the stent, as well as to maximize the interior cross-sectional area of the stent relative to the passing or outer profile.

FIGS. 1-5 illustrate optional embodiments of a stent that uses offset overlapping elements. However, in other embodiments, a radial element or stent component can comprise a variable thickness along the backbone thereof. Thus, elongate members may fit within sections of the backbone that have a reduced thickness in order to provide a smoother outer surface of the stent and reduce the passing profile thereof.

As noted, it is contemplated that other overlapping sections of the stent can have one or more offset portions. The offset portions can be offset in a radial direction such that when overlapping with another stent component, the passing profile of the stent is generally reduced. An example of a crossbar 36 is illustrated in FIG. 1. As shown therein, a distal end of a U-shaped elongate member (which is formed from two elongate members 32 that are joined in a distal end) can have a crossbar 36 that is radially offset relative to the elongate members 32 of the U-shaped elongate member. Accordingly, when the offset crossbar 36 abuts a given surface or portion of a corresponding stent component, the elongate members of the U-shaped elongate member can tend to be radially nested with portions of the corresponding stent component.

In this regard, in accordance with some embodiments, an offset portion or bridge portion formed intermediate one or more elongate members can be referred to as a "semi-captive" slot.

Further, it is contemplated that in some embodiments, the offset portion of a stent component can comprise an engagement means. The engagement means can be configured to contact and to interact with a portion of a corresponding stent component. Thus, when a corresponding stent component is received against the offset portion, the offset portion can function to restrict the articulation or movement of the portion of the corresponding stent component relative to the offset portion. Thus, in some embodiments, a stent component or radial element can comprise a semi-captive slot having an engagement means that interconnects the semi-captive slot (and therefore indirectly interconnects the distal ends of the elongate members) with the overlapped portion of the stent component or radial element. However, the semi-captive slot need not comprise an engagement means, but can comprise three or more surfaces or boundaries that restrict movement of the portion of the corresponding stent component in three or more respective directions. In some embodiments, a direction in which the movement is restricted can be in a circumferential direction which allows the offset portion to participate in restricting expansion or contraction of the stent.

It is also noted that in FIGS. 1-5, the crossbars 36, 46 are disposed on a radially exterior portion of the stent components or radial elements 20, 22. In other words, when overlapping a corresponding elongate member 42, the crossbar 36 will be exposed along the exterior surface of the stent 10, as shown in FIG. 5.

Referring again to FIG. 1, the flexible backbone 30 of the radial element 20 comprises a number of elongate members 32 extending in a direction substantially perpendicular to the longitudinal axis of the tubular member. In the embodiment of FIG. 1, the elongate members 32 can be described as having a substantially annular or ring-like geometry. These elongate members 32 can be referred to as annular elongate members, comprising two rails and an end linkage or bridge portion that interconnects the distal ends of the annular elongate members 32. Of these annular elongate members 32 is a first annular elongate member and a second annular elongate member, the second elongate member being substantially axially or circumferentially offset with respect to the first elongate member. Additionally, a majority of the elongate members are at least partially axially or circumferentially offset with respect to each other.

FIG. 1 further illustrates a plurality of fully captive slots 34 distributed along the flexible backbone 30. Additionally, each annular elongate member 32 comprises a semi-captive slot, which can be formed at least partially by the crossbar 36 at the distal end with respect to the flexible backbone 30. The semi-captive slot formed by the crossbar 36 on the distal end of the elongate member can be somewhat different than the slots 34 on the backbone 30; however, both semi- or fully captive slots can define an inner surface that is configured to substantially confine a slidably engaged rail to a unidirectional travel path. Further, as discussed herein, a semi-captive slot can allow at least two degrees of movement while a captive slot can allow a single degree of movement.

With respect to FIG. 1, it is contemplated that the flexible backbone 30 can also be configured with variable thickness to provide the desired flexibility for an intended use.

Figure 2:
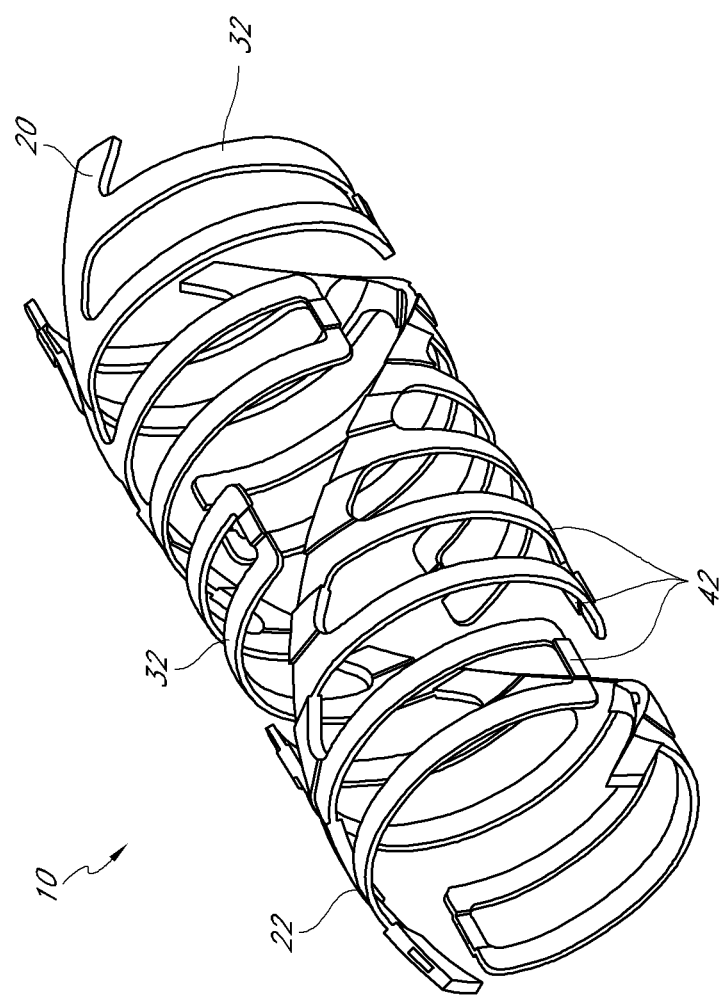
FIG. 2 is a perspective view of a pair of radial elements forming a stent in an exploded state in accordance with another embodiment.
Figure 3:
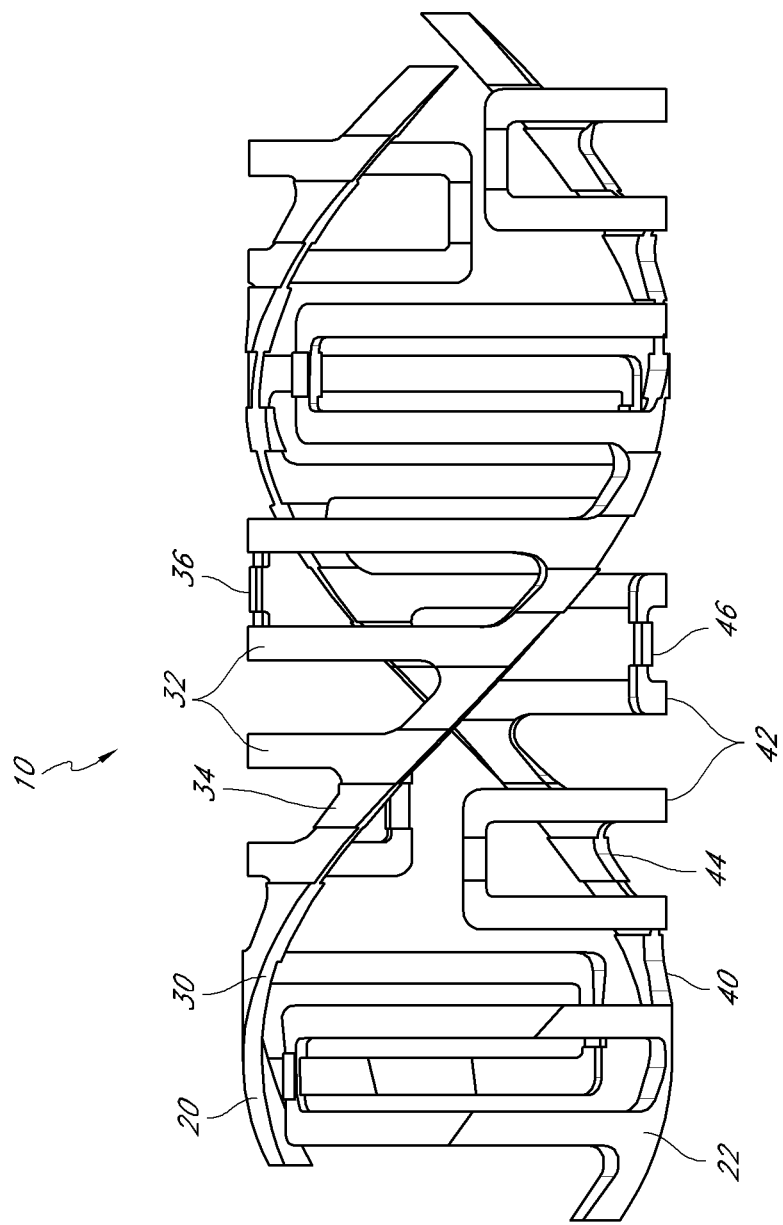
FIG. 3 is a side view of the stent shown in FIG. 2, in its exploded orientation.

FIGS. 2 and 3 illustrate an embodiment of the stent 10 in an exploded orientation. Referring to these figures, one having skill in the art can understand how each radial module fits together to embody the tubular member of the stent. In these figures, one will recognize that each annular elongate member 32 of the first radial element 20 comprises a semi-captive slot formed by the crossbar 36 which is generally aligned and adapted to be engaged with a rail or elongate member 42 located on the opposing radial element 22.

Additionally, one having skill will recognize that the slots 34, 44 located along the backbones 30, 40 can have an increased thickness with respect to the flexible backbone. Further, the slots 34, 44 along the elongate members 32, 42 can variable thickness or be formed from an offset portion with respect to the elongate members 32, 42, as discussed above. It may be advantageous to minimize the thickness of the flexible backbones 30, 40 in order to increase flexibility of the stent 10; however thickness around the captive slots 34, 44 can serve an alternate function, to provide strength and support to the engaged rails. Thus, in this embodiment, the thickness of the flexible backbone linking two captive slots can be minimized to allow for greater flexibility as seen in FIGS. 1-5.

Figure 4:
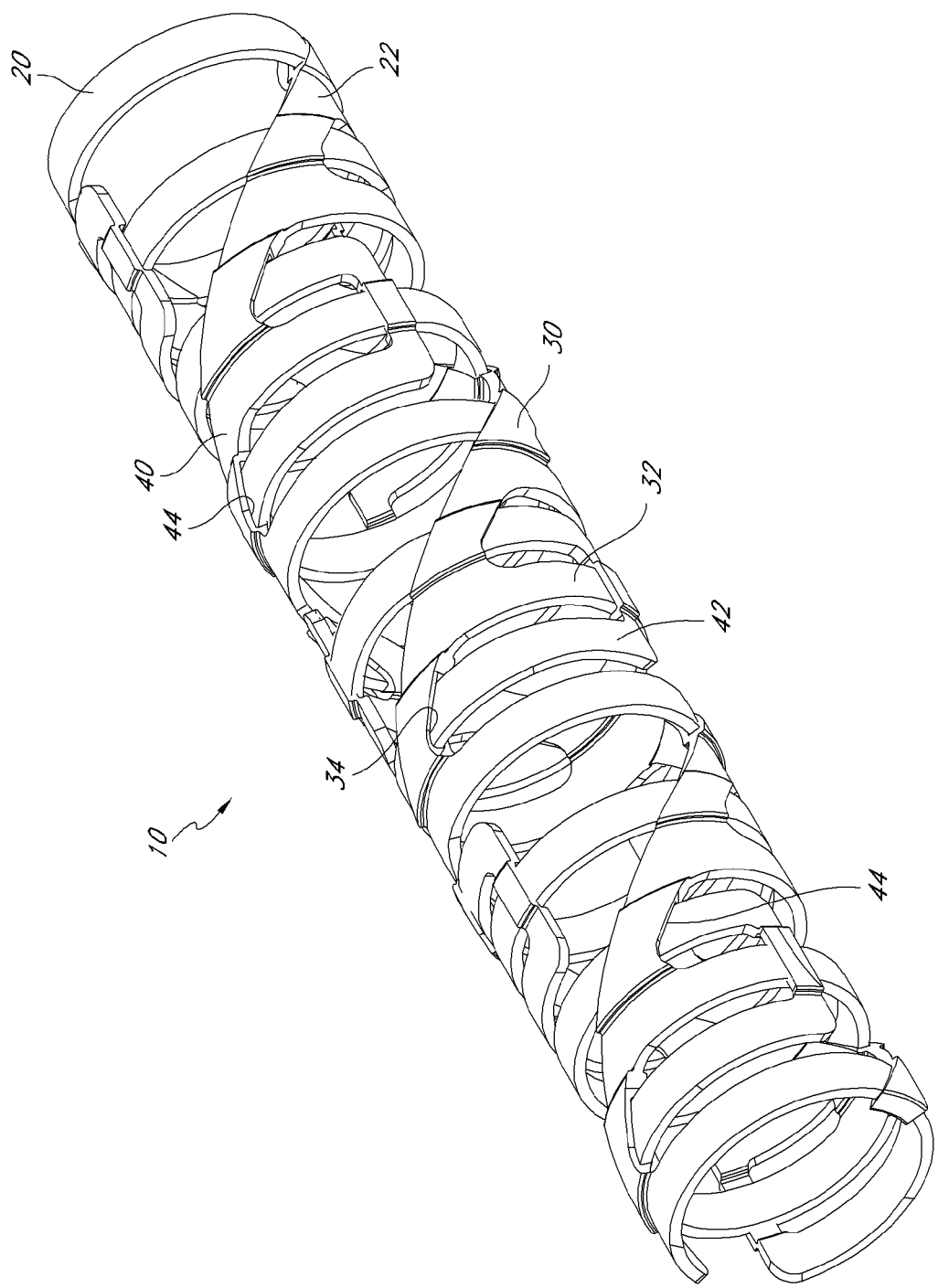
FIG. 4 is a perspective view of the stent of FIG. 2 in an assembled, expanded state.

FIGS. 4-5 show the stent in a configured and substantially expanded orientation of the embodiment. One having skill in the art will recognize the joinder of rails and captive slots. Although in this particular embodiment each rail is slidably engaged with a captive slot, it would be recognized by one having skill in the art that not all rails require an engagement with a captive slot. Further, FIGS. 4 and 5 illustrate the stent having a circumferential distribution of engagements. According to one of the advantageous aspects of various embodiments disclosed herein, the circumferential distribution of engagements between the elongate members or rails with the slots can serve to prevent the stent from hinging. Thus, several disadvantages of straight-backbone stents are overcome in using the unique combination of features disclosed herein.

Figure 6:
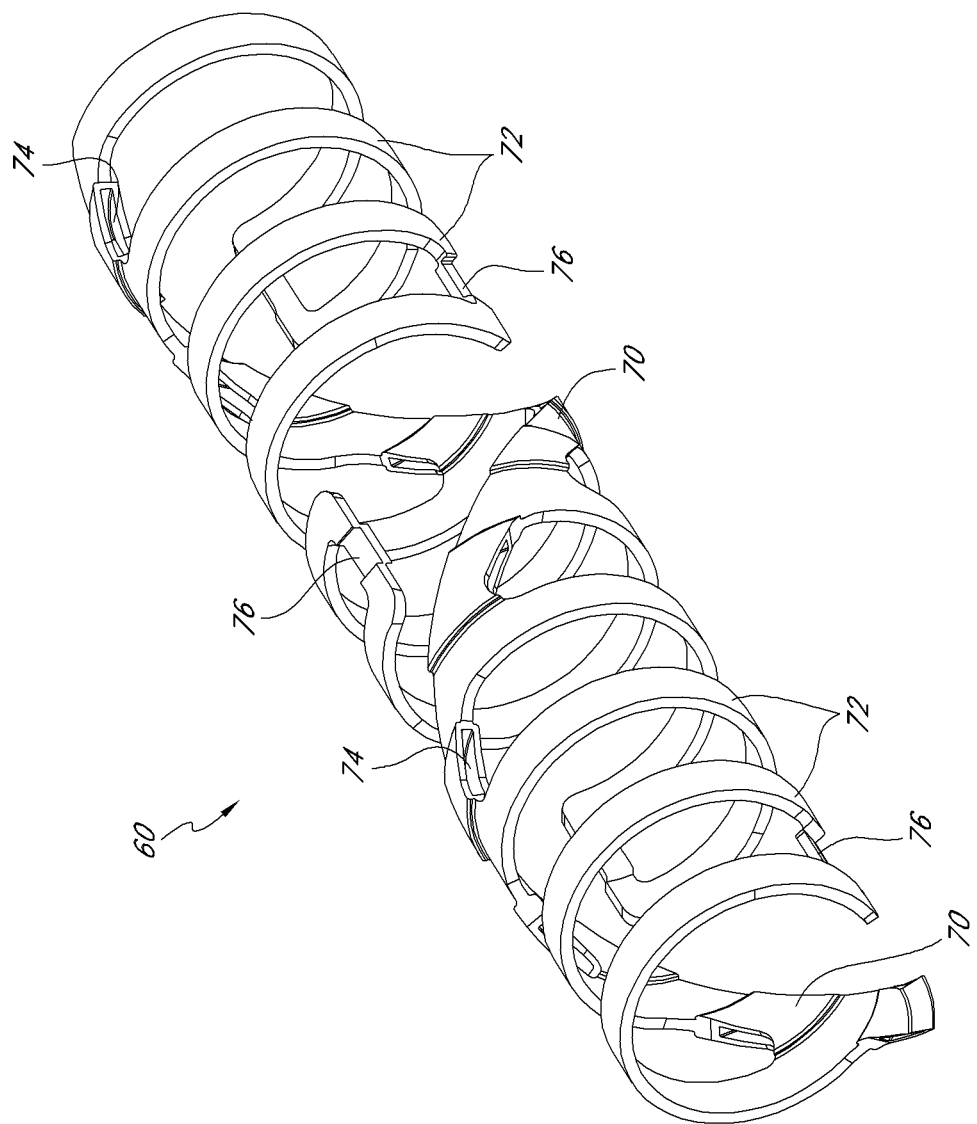
FIG. 6 is a perspective view of a single radial element of a stent in accordance with another embodiment.
Figure 7:
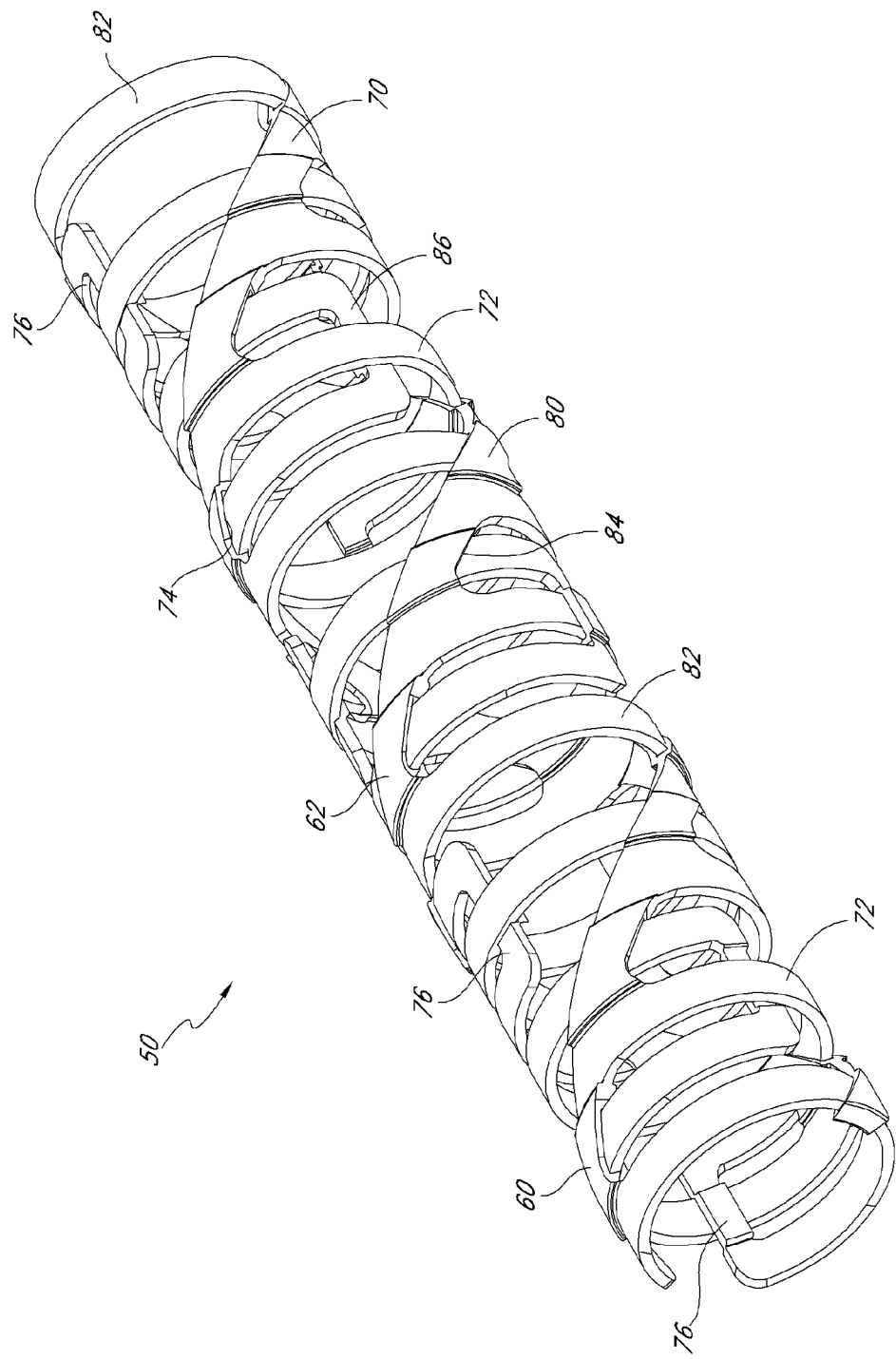
FIG. 7 is a perspective view of a stent formed from the radial element of FIG. 6, in an assembled, expanded state.
Figure 8:
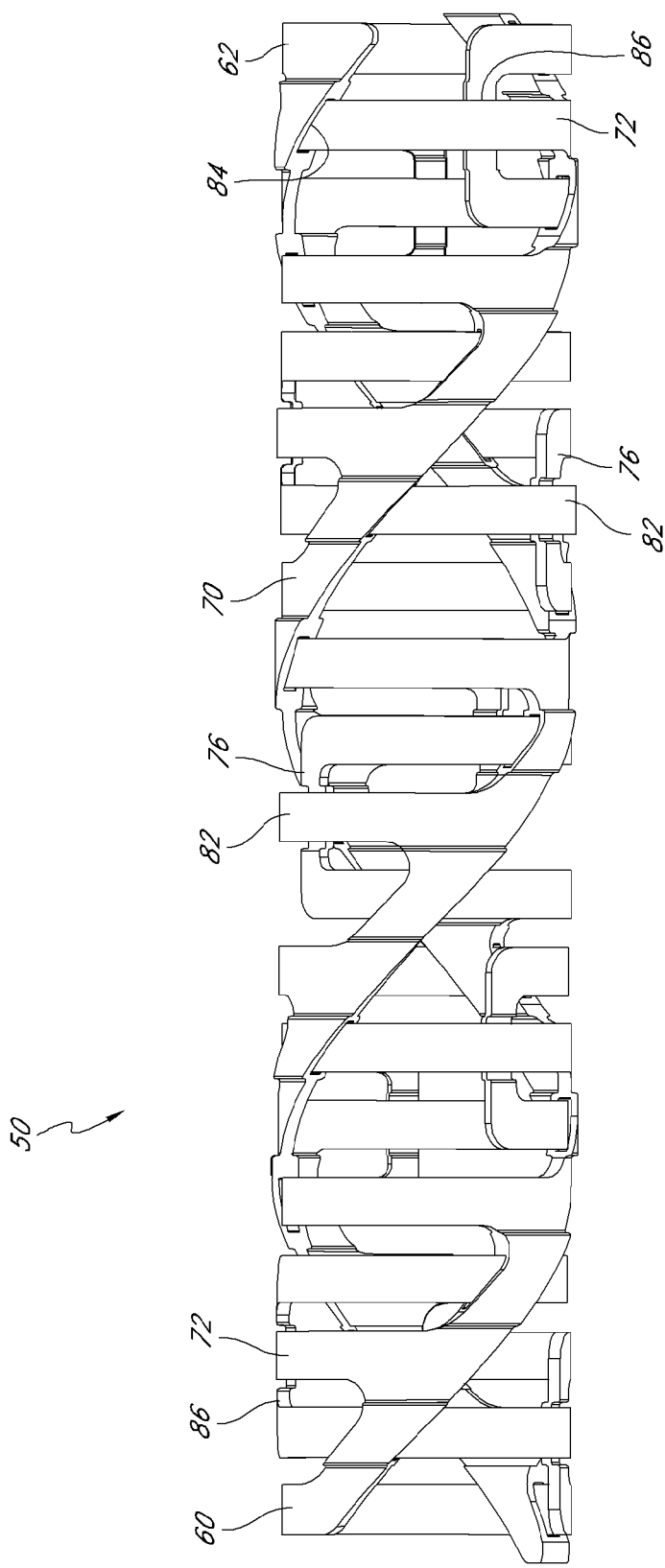
FIG. 8 is a side view of a stent formed from the radial element of FIG. 6, in the assembled, expanded state.

Additionally, as illustrated in the embodiment of FIGS. 6-8, a stent 50 is provided that can comprise a stent component or radial element 60 that includes a backbone 70, at least one elongate member 72, and a slot 74. Further, the stent 50 can also comprise a stent component or radial element 62 that includes a backbone 80, at least one elongate member 82, and a slot 84.

The radial element 60 shown in FIG. 6 is similar to the radial element 20 shown at FIG. 1. However, the embodiment of FIG. 6 comprises U-shaped members or elongate members 72 of the radial element 60 that are configured such that ends thereof can be radially nested with corresponding elongate members of an adjacent radial element. In some embodiments, a connecting portion or U-shaped portion of the elongate members 72 can be radially bounded by or interlocked with the elongate members of the adjacent radial element. Accordingly, in such embodiments, the connecting portion of the elongate members or U-shaped members can comprise a trough or depression configured to receive at least a portion of an elongate member of an adjacent radial element.

For example, in some embodiments, the radial elements 60, 62 can each comprise offset portions 76, 86. The offset portions 76, 86 can be configured such that they are disposed on a radially interior portion of the stent component or radial elements 60, 62. In such embodiments, as shown in FIGS. 7-8, the offset portions 76, 86 can be exposed along the interior surface of the stent 50.

Thus, the elongate members 72, 82 of the radial elements 60, 62 can be radially nested while preventing protrusion of the elongate members 72, 82 of the radial elements 60, 62 toward the lumen or vessel of the patient. In other words, if the offset portions 76, 86 are configured to underlay a portion of the corresponding stent components or radial elements 60, 62, any resilience of the stent component itself (which may cause the stent component to straighten and protrude outwardly toward the vessel wall) can be counteracted due to the interweaving and underlayment of the offset portion with a section or portion of the corresponding stent component. Additionally, in some embodiments, the flexible backbones 70, 80 can be configured with variable thickness to provide the desired flexibility for an intended use.

FIGS. 7 and 8 illustrate the embodiment of a stent 50 formed using the radial element 60 shown at FIG. 6, in an assembled orientation. Referring to these figures, one having skill in the art can understand how each radial module 60, 62 fits together to form the tubular member of the stent. For example, the embodiment of FIGS. 6-8 can be visualized as being interconnected as shown with reference to the exploded views of FIGS. 2-3 above. Accordingly, one will recognize that each annular elongate member of the first radial element comprises a captive slot which is generally aligned and adapted to be engaged with a rail located on the opposing radial element.

Additionally, one having skill will recognize that the captive slots located along the backbone and on the annular elongate members have an increased thickness with respect to the flexible backbone. It is important to minimize the thickness of the flexible backbone in order to increase flexibility; however thickness around the captive slots serves an alternate function, to provide strength and support to the engaged rails. Thus, in this embodiment, the thickness of the flexible backbone linking two captive slots can be minimized to allow for greater flexibility as seen in FIGS. 6-8.

As noted, FIGS. 7 and 8 show a stent formed by the radial elements of FIG. 6 in an assembled and substantially expanded configuration, according to an embodiment. One having skill in the art will recognize the joinder of rails and captive slots. Although in this particular embodiment each rail is slidably engaged with a captive slot, it would be recognized by one having skill in the art that not all rails require an engagement with a captive slot. Further, FIGS. 7 and 8 illustrate the stent having a circumferential distribution of engagements. The circumferential distribution of engagements prevents the stent from hinging.

The embodiments illustrated in FIGS. 1-8 can be modified in various ways and generally relate to stents having one or more expandable radial elements. Each radial element individually comprises a flexible backbone, a plurality of annular elongate members, and a plurality of slots distributed along the flexible backbone and on the distal end of the annular elongate members. The slots can be fully captive or semcaptive. The radial elements can be slidably engaged and adapted for unidirectional slidable movement from a first collapsed diameter to a second expanded diameter. Additionally, the either the rails of the elongate members and/or the slots can comprise an engagement means, such as teeth, adapted to engage with respective slots and/or elongate members such as to prevent recoil. The flexible backbone can be configured to coil about the tubular member, providing rotational flexibility as well as flexibility sufficient to allow stenting of a curved vessel.

Additionally, the disclosures of Applicant's patents and copending patent applications are hereby incorporated by reference in their entireties and include U.S. patent application Ser. Nos. 11/016,269, 11/455,986, 11/196,800, 12/193, 673, 11/399,136, 11/627,898, 11/897,235, 11/950,351, 11/580,645, 11/680,532, and U.S. Pat. No. 6,951,053.

FIGS. 9-29B illustrate a variety of radial elements that can be fabricated into a stent having the features of the disclosed embodiments. Variations from these figures can be easily generated without undue experimentation that can provide the features set forth above and claimed below.

Figure 9:
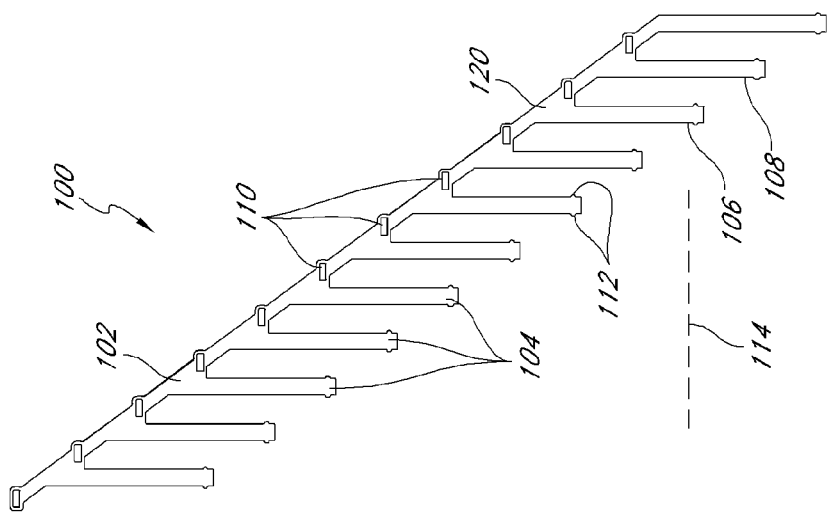
FIG. 9 is a planar view of a radial element of another embodiment, in a preconfigured orientation.

FIG. 9 illustrates an embodiment where a slidably engaged radial element 100 comprises a flexible backbone 102, a plurality of elongate members 104 including a first elongate member 106 and a second elongate member 108, and a plurality of slots 110 distributed along the flexible backbone.

In the embodiment illustrated in FIG. 9, the elongate members 104 comprise at least one tooth 112 located on two axial sides of the elongate member 104. The slots 110 shown in FIG. 9 are generally parallel with respect to a longitudinal axis 114 of the radial element 100 and aligned with the elongate members 104. In this regard, the radial element 100 can be interconnected with a second radial element with the slots and elongate members of the second radial element being axially offset from the those of the radial element 100. In this manner, the slots of the second radial element can be aligned to engage with the elongate members 104 of the radial element 100 and rolled to form a tubular member.

In the embodiment shown in FIG. 9, backbone material 120 is increased between the elongate members 104 and the slots 110 relative to the remainder of the backbone 102 so as to provide additional support. In particular, the elongate members 104 can be radially spaced at approximately between the one to two times the width of the slot 110.

Figure 10:
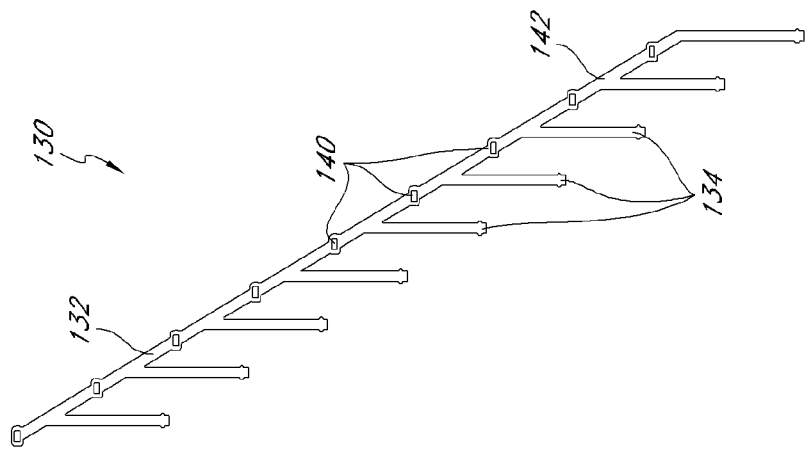
FIG. 10 is a planar view of a radial element of another embodiment, in a preconfigured orientation.

FIG. 10 illustrates another embodiment wherein a radial element 130 comprises a flexible backbone 132, a plurality of elongate members 134 including a first elongate member and a second elongate member, and a plurality of slots 140 distributed along the flexible backbone 132. Further, as with the embodiment shown in FIG. 9, the slots 140 of the radial element 130 can be generally parallel with respect to a longitudinal axis (not shown) of the radial element 130. In this embodiment, there is also a minimum amount of backbone material 142 between the flexible backbone 132 and the elongate members 134. This particular embodiment allows for greater flexibility with less bulk material. Additionally, the elongate members 132 comprise an increased spacing to allow for additional improved flexibility. In particular, the elongate members 134 can be radially spaced at approximately between the three to four times the width of the slot 140.

FIG. 10 further illustrates a radial element 130 having a thinned backbone 132, where the material between the flexible backbone is relatively thin compared to the material of the slots 140, which provides further flexibility.

Figure 11:
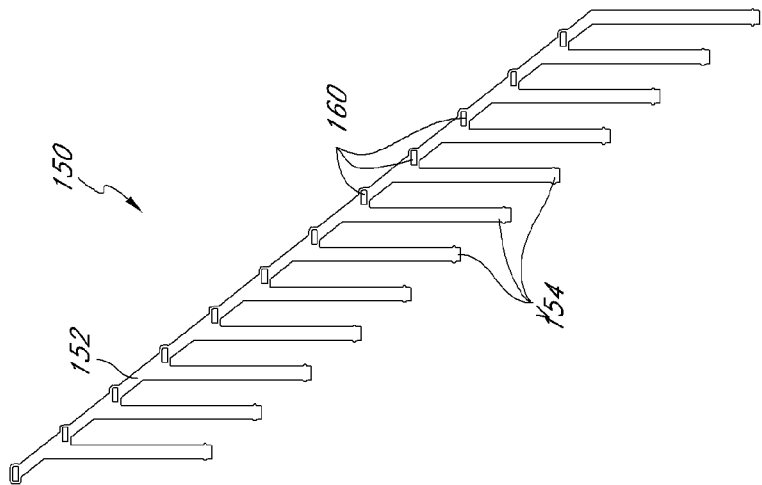
FIG. 11 is a planar view of a radial element of another embodiment, in a preconfigured orientation.

FIG. 11 illustrates a general compromise between the embodiments of FIGS. 9 and 10. The compromise allows for some improvements in flexibility while having structural improvements such as added bulk material between elongate members. Accordingly, a radial element 150 is shown in FIG. 11 which comprises a flexible backbone 152, a plurality of elongate members 154 including a first elongate member and a second elongate member, and a plurality of slots 160. In this embodiment, the elongate members 154 are relatively thin with respect to their width. Additionally, there is slight bulk material between elongate members 154 and slots 160. Furthermore, the elongate members 154 are spaced relatively close to each other with respect to the design in FIG. 10. In particular, the elongate members 154 can be radially spaced at approximately between the two to three times the width of the slot 160.

Figure 12:
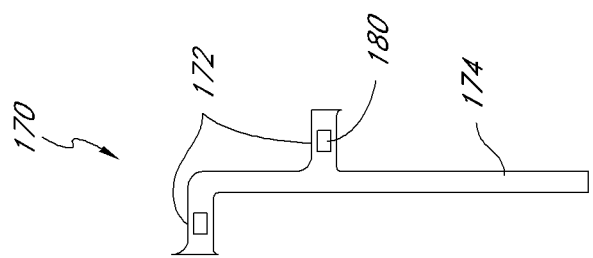
FIG. 12 is a planar view of a modular radial element, according to an embodiment.

An embodiment shown in FIG. 12 illustrates a flexible linkage element 170 having a flexible backbone 172 with a stair-step offsetting. Further, the element 170 can comprise one or more elongate members 174 and one or more slots 180. It is also realized that the embodiment illustrated in FIG. 12 can be used to fabricate a stent via modular fitting.

Additionally, it is contemplated that the embodiment of FIG. 12 can provide a flexible linkage between elongate members 174 and slots 180 which can provide added flexibility. One having skill in the art will recognize that the stair-step of FIG. 12 is one of many ways to embody a flexible linkage. It will be understood that a flexible backbone 172 can include a stair-step or wave-like pattern which substantially coils about the stent. The flexible backbone can comprise any design pattern which is generally configured to coil about the stent.

Figure 14:
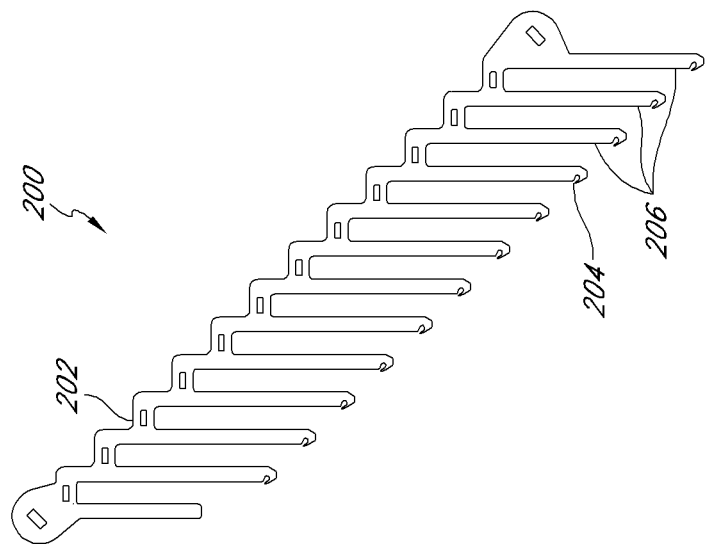
FIG. 14 is a planar view of a radial element of another embodiment, in a preconfigured orientation.
Figure 13:
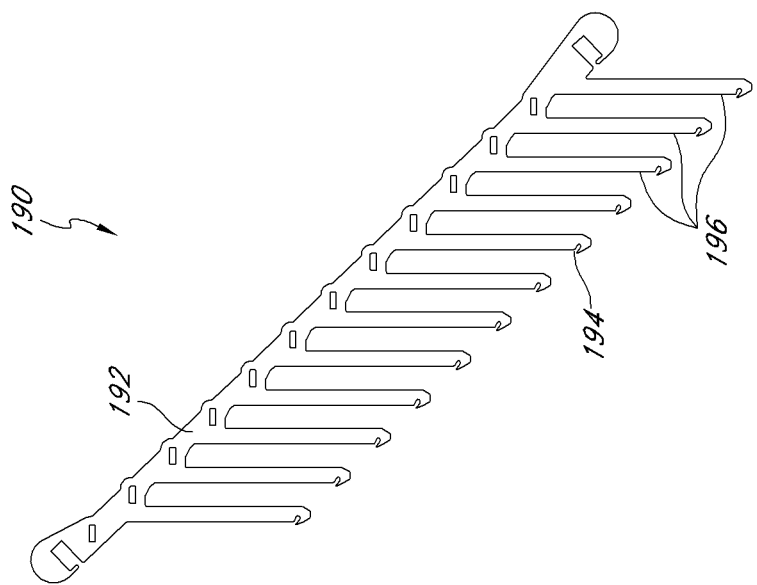
FIG. 13 is a planar view of a radial element of another embodiment, in a preconfigured orientation.

The embodiments of FIGS. 13-14 illustrate two variations of a radial element 190, 200 having a flexible backbone 192, 202. The backbone 202 of the radial element 200 provides more of a stair-step than the backbone 192 of the radial element 190. Similar to the embodiments of FIGS. 9-12, slots disposed on the backbones 192, 202 can be oriented generally parallel to a longitudinal axis of the radial elements 190, 200.

Additionally, the embodiments in these figures introduce a deflectable tooth 194, 204 at the distal end of elongate members 196, 206 of the radial elements 190, 200, respectively. It would be understood by one having skill in the art that a plurality of deflectable teeth can be added to provide for customization of the diameter of the stent. Further, the flexible teeth 194, 204 can be configured on either axial side in a mirrored alignment, or a mirrored and offset alignment as described above. Furthermore, the elongate members 196, 206 can be radially spaced at approximately between one to two times the width of a slot.

Figure 15:
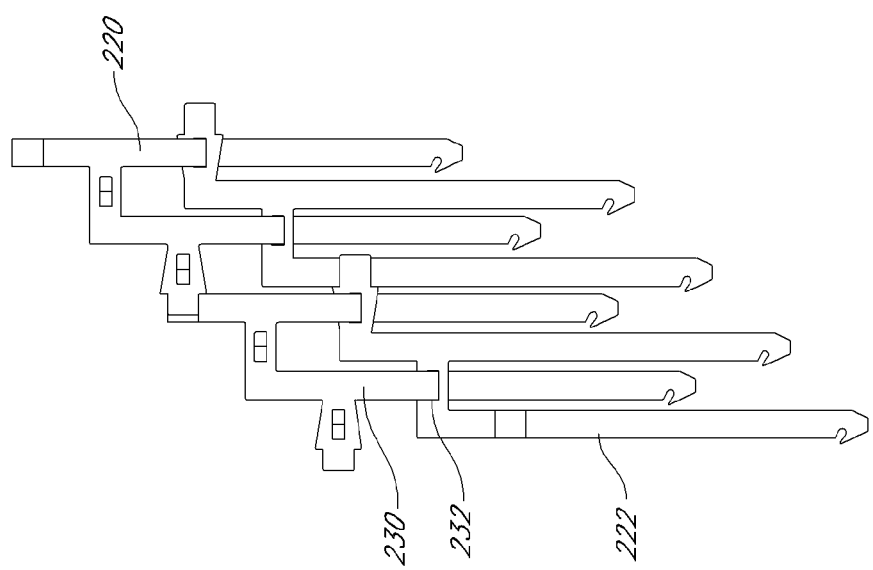
FIG. 15 is a planar view of two modular radial elements illustrating engagement between elongate members and slots, according to an embodiment.

The slidable engagement between radial elements allows for a reduced cross sectional area which greatly improves deliverability by allowing a minimally invasive delivery of the stent. FIG. 15 illustrates the engagement between two radial elements 220, 222. In this embodiment, the elongate members 230 of a first radial element 220 are slidably engaged with the slots 232 of a second radial element 222. FIG. 15 illustrates a stair-step flexible backbone and elongate members having deflectable teeth at the distal end with respect to the flexible backbone.

Figure 16:
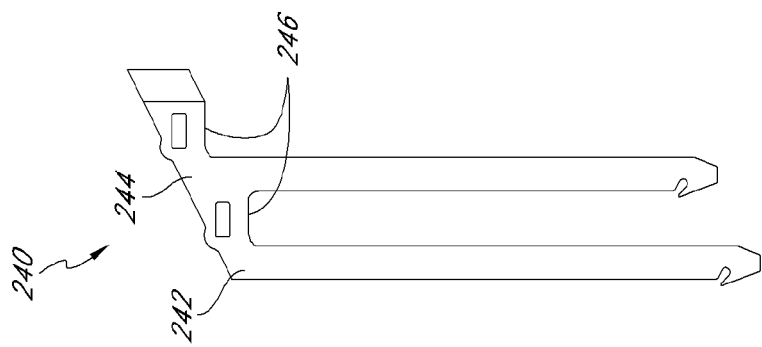
FIG. 16 is a planar view of a modular radial element having a combination flexible backbone, according to an embodiment.

The embodiment of FIG. 16 illustrates another variation in the flexible backbone. In this embodiment, a flexible linkage element 240 is illustrated as having a backbone 242 that is essentially a combination stair-step and standard elongate backbone. In this regard, an upper portion 244 of the backbone 242 can be configured to resemble a standard backbone, such as that shown in FIGS. 9-12. Further, a lower portion 246 of the backbone 242 can be configured to resemble a stair-step backbone, such as that shown in FIGS. 12, 14, and 15. One having skill in the art will recognize that the upper portion 244 of the flexible backbone 242 shown in FIG. 16 is relatively smooth and that the lower portion 246 of the flexible backbone 242 is in a stair-step configuration. This embodiment illustrates one of the many variations of the radial elements disclosed herein that one having skill in the art can derive without undue experimentation.

Figure 17:
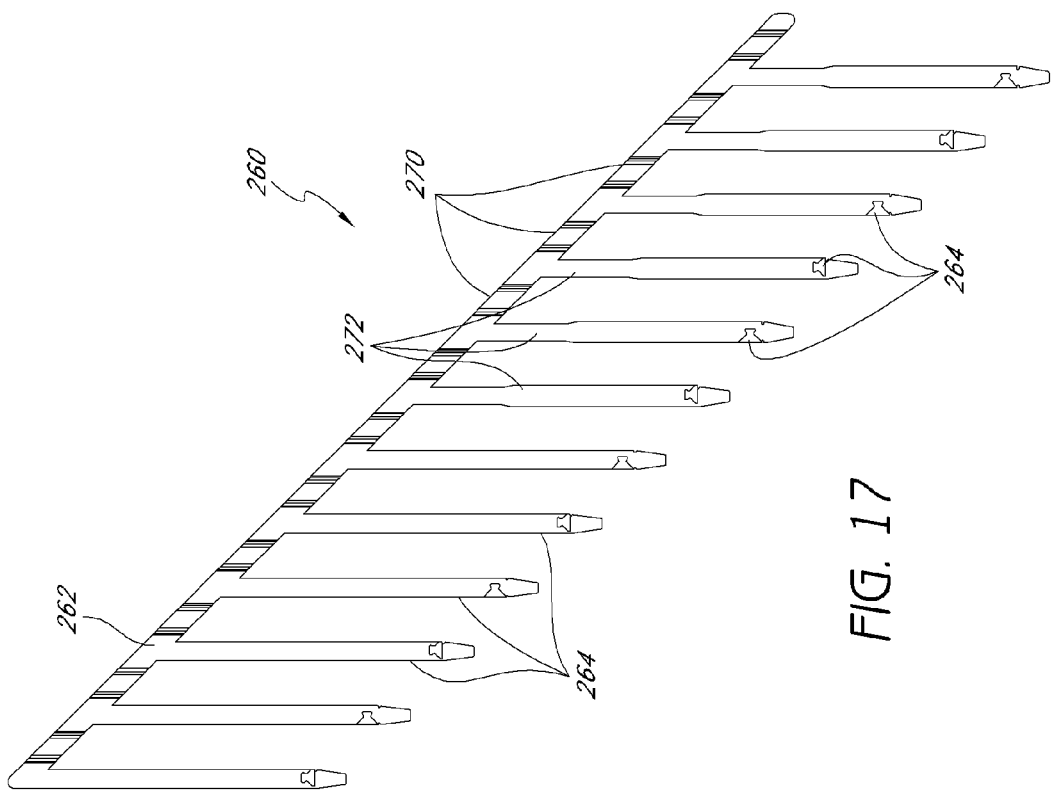
FIG. 17 is a planar view of a radial element comprising a plurality of substantially captive slots and depicting a variable arrangement of conjugate locking members, according to an embodiment.

The embodiment of FIG. 17 illustrates a radial element 260 comprising a flexible backbone 262, a plurality of elongate members 264 including a first elongate member and a second elongate member, and a plurality of fully or semi-captive slots 270. A substantially captive slot is a slot which is configured to engage a rail with at least three sides or a majority of the rail's outer surface. Additionally, this embodiment illustrates variable elongate members. Here, some elongate members 264 have a portion 272 which comprises a decreased width at the proximal end with respect to the flexible backbone to allow increased flexibility. Additionally, the drawing illustrates a variable direction of conjugate locking members 274. The conjugate locking members 274 can comprise a tooth, a deflectable tooth, or a stop, to name a few.

Figure 18:
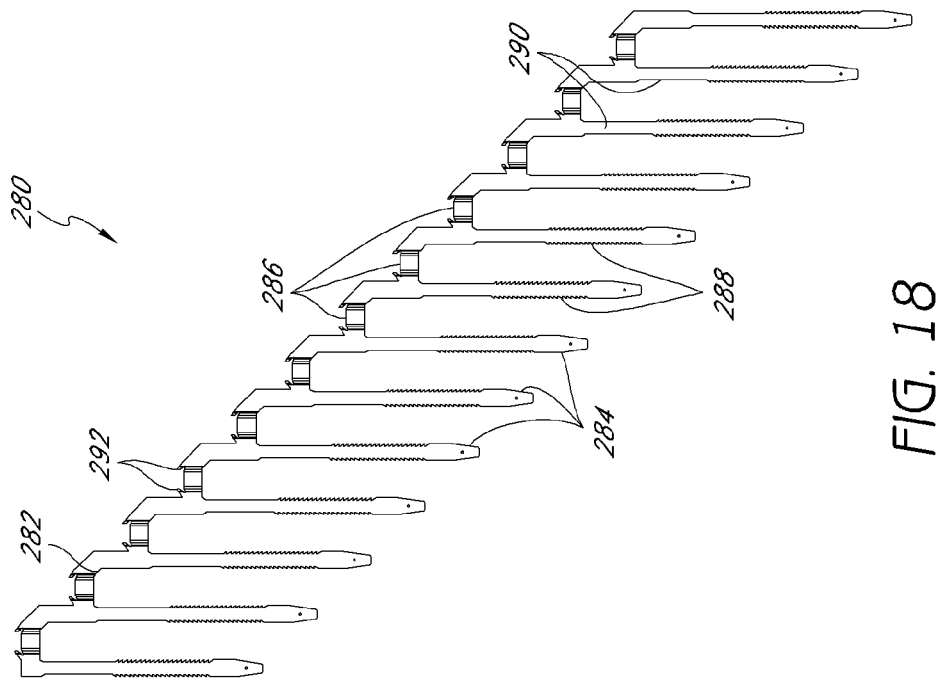
FIG. 18 is a planar view of a radial element of another embodiment, in a preconfigured orientation.

Another embodiment illustrated in FIG. 18 shows a radial element 280 comprising a flexible stair-step backbone 282, a plurality of elongate members 284 including a first elongate member and a second elongate member, and a plurality of substantially captive slots 286. The radial element 280 can also comprise one or more conjugate locking members 288 on the rail or elongate members 284, as well as a portion 290 of decreased width. This particular embodiment illustrates a fully captive slot 286 having two deflectable teeth 292 outside the inner surface of the slot 286. In this embodiment, the deflectable teeth 292 extend from the captive slot 286 and are adapted to engage conjugate locking members of an elongate member or rail of an adjacent radial element. Additionally, this embodiment shows a mirrored alignment of conjugate locking members, here embodied as teeth, along both axial sides of the elongate member.

Figure 19:
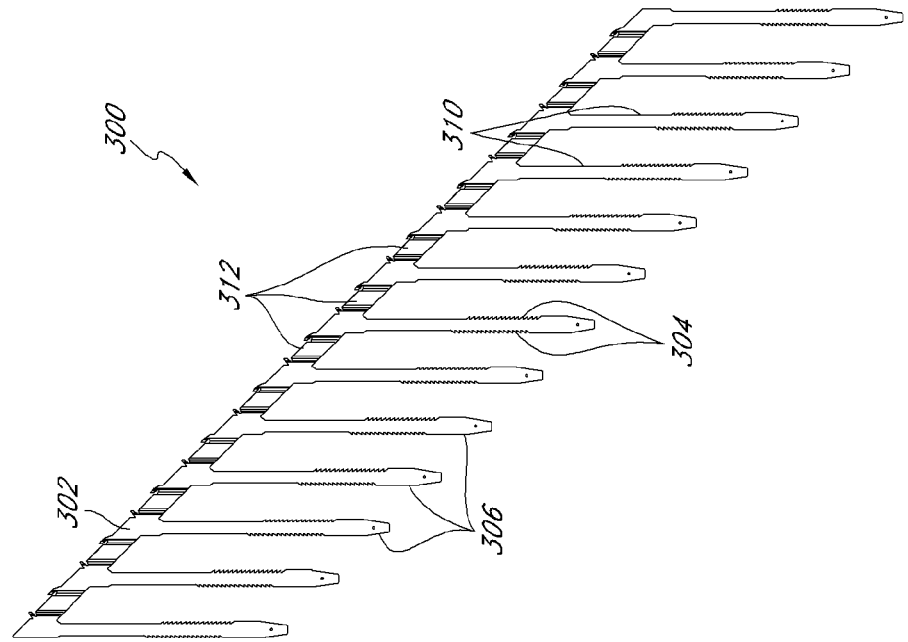
FIG. 19 is a planar view of a radial element of another embodiment, in a preconfigured orientation.

FIG. 19 shows a variation of the embodiment disclosed in FIG. 18, wherein a radial element 300 has a straight flexible backbone 302. In this embodiment, conjugate locking members 304 are configured along both axial sides of an elongate member 306 in a mirrored and offset pattern. The radial element 300 of FIG. 19 also illustrates that the elongate members 306 can comprise narrowed portions 310. Further, in accordance with a unique aspect of the illustrated embodiment, as shown in FIGS. 19-20C, the radial element 300 can comprise one or more slots 312 having at least one locking mechanism 314. The illustrated slot 312 is an embodiment of a completely or fully captive slot.

FIGS. 20A-C also illustrate perspective views of the fully captive slots 312 of the embodiment of the stent shown in FIG. 19. In this embodiment, the substantially captive slot 312 has a top portion or rim 320, a bottom portion 322 and an inner surface. Adjacent to the top portion 320 of the substantially captive slot extends a deflectable tooth 314. The deflectable tooth 314 is adapted to engage with a conjugate locking member from a slidably engaged rail, and permit unidirectional slidable movement of the rail or elongate member 306 through the slot 312. FIG. 20B shows that the tooth 314 can comprise a gap between the tooth 314 and the top portion or rim 320 in order to provide the ability of the deflectable tooth 314 to articulate from an extended configuration to a compressed articulation. FIGS. 20A-C also demonstrate a plurality of deflectable teeth 314 extending adjacent to the top side 320 of the slot 312.

In order to assemble the stent assembly, with reference to FIGS. 20A-C, when an elongate member such as element 306 is inserted into the slot 312, it is possible to defeat the locking mechanism 314 in order to allow the conjugate locking members or teeth 304 of the radial element to pass through the slot towards a collapsed position. The locking mechanism 314, which is shown as one or more teeth that extend into the passage formed by the slot 312, can be defeated by pushing the teeth 314 into a deflected, non-engaging position during assembly. The teeth may then be released to return to the extended configuration so as to re-enable the locking mechanism in the assembled stent. A number of alternative methods of defeating or dis-enabling the locking mechanism may be used to facilitate assembly of the stent. For example, process steps may be included such as modifying the shape of tooth 314 with heat and pressure into a deflected, non-engaging positions so as to defeated the locking mechanism to permit assembly. Following assembly, a similar process step may be used to return tooth 314 to an extended engaging position so as to re-enable the locking mechanism. Similarly, shape memory properties of the material may be used in such process steps, whereby following assembly, tooth 314 extends to the engaging position by internal phase changes upon application of heat. Alternatively, the tooth 314 may be initially formed in the deflected, non-engaging position, and the tooth 314 then repositioned following assembly to an extended, engaging configuration so as to enable the locking mechanism.

In yet another alternative, the conjugate locking members or ratcheting teeth 304 on the rail or radial element 310 may be configured to permit them to be deflected into a non-engaging position by means of one or more shims or enclosing covers (not shown) during assembly, permitting the element 310 to be moved through captive slot 312 (of a companion, adjacent radial element 300) toward an assembled collapsed stent configuration. Removal of the shims or enclosing covers then permits the members 304 to return to an engaging or locking configuration following assembly.

Note that there does not necessarily need to be a conjugate paring of locking mechanisms on the radial or rail elements 310 and on the backbone 302. For example, as shown the embodiments of FIGS. 38 through 43, the locking mechanism or teeth of the radial or rail element may engage directly with the structure of the backbone, without any specific engaging locking element on the backbone. This is particularly convenient where the rail mounting locking mechanism is defeated during assembly (e.g., for tail bonded examples), or where the rail mounting locking mechanism does not need to pass through an adjacent backbone slot during assembly (e.g., for core bonded examples).

Subsequently, during expansion, the teeth 314 can engage the conjugate locking members 304 to provide a ratcheting-type movement of the elongate member 306 relative to the slot 312. As the rail 306 moves through the slot 312 from the bottom portion to the top portion, the deflectable tooth is deflected out. However, a rail 306 attempting to move in a direction from the top portion 320 to the bottom portion 322 of the slot 312 will engage the deflectable tooth 314 and deflect that tooth 314 in order to prevent further movement in the undesired direction. As illustrated, because in this embodiment, the teeth 314 extend from an outer rim 320 of the slot 312, movement of the stent from an expanded to a collapsed state creates compressive stress against the teeth 314. As such, the locking mechanism 314 resists collapse of the stent and can exhibit superior strength and structural properties in maintaining the stent in an expanded configuration.

Figure 21:
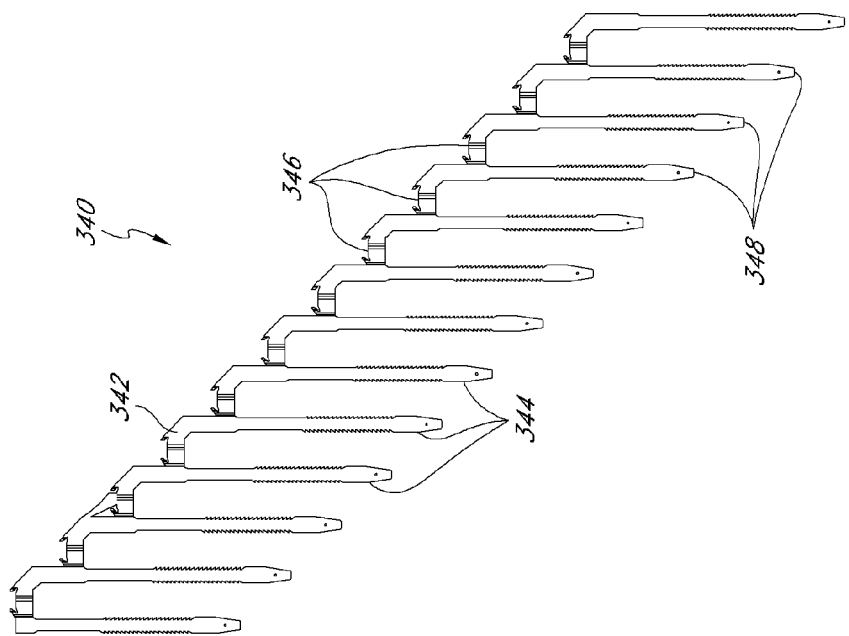
FIG. 21 is a planar view of a radial element of another embodiment, in a preconfigured orientation.

One having skill in the art can recognize that the features of the previous embodiments can be incorporated to adjust flexibility, strength, and size as illustrated in FIG. 21. FIG. 21 illustrates an embodiment of a radial element 340 having a flexible backbone 342, a plurality of elongate members 344, and a plurality of slots 346. The radial element 340 is configured with distal ends 348 of the elongate members 344 being oriented to lie along a helical or angled line which can improve the resistance for hinging.

Figure 22:
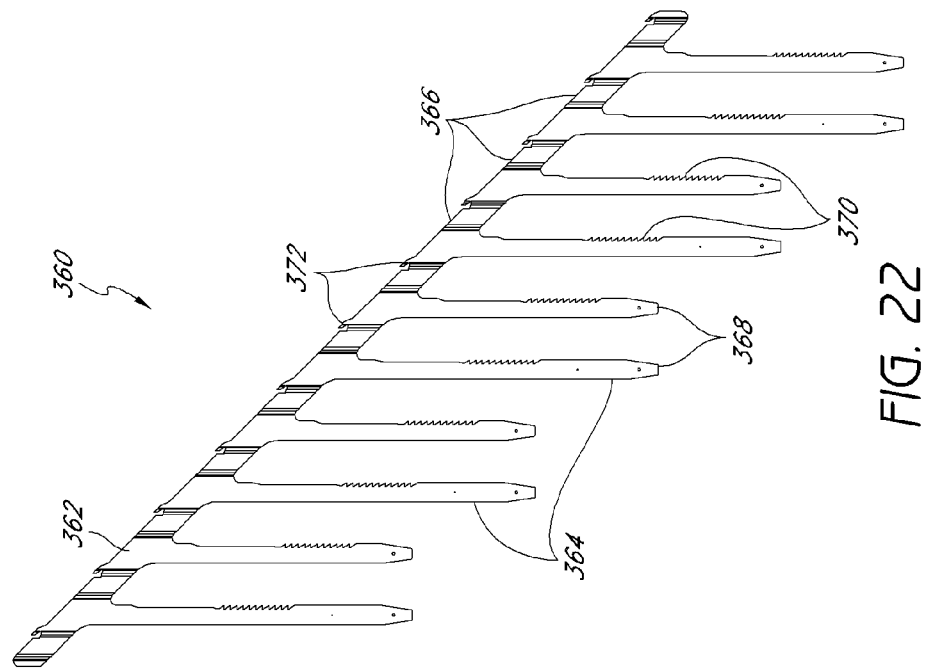
FIG. 22 is a planar view of a radial element of another embodiment, in a preconfigured orientation.

Added radial support can be provided by the embodiment illustrated in FIG. 22. The embodiment of FIG. 22 illustrates a radial element 360 that comprises a flexible backbone 362, a plurality of elongate members 364 including a first elongate member and a second elongate member, and a plurality of fully captive slots 366. In this particular embodiment, the elongate members 364 can be paired elongate members, which are labeled as element 368. In this regard, "paired elongate members" can be defined as those that extend from the flexible backbone to a common distal point. The paired elongate members 368 can be advantageous in that they provide added radial strength combined with incremental longitudinal support. The paired members 368 of this embodiment have conjugate locking members 370, such as teeth, on an axial side and mirrored and offset such to enable a distribution of engagements.

Figure 24:
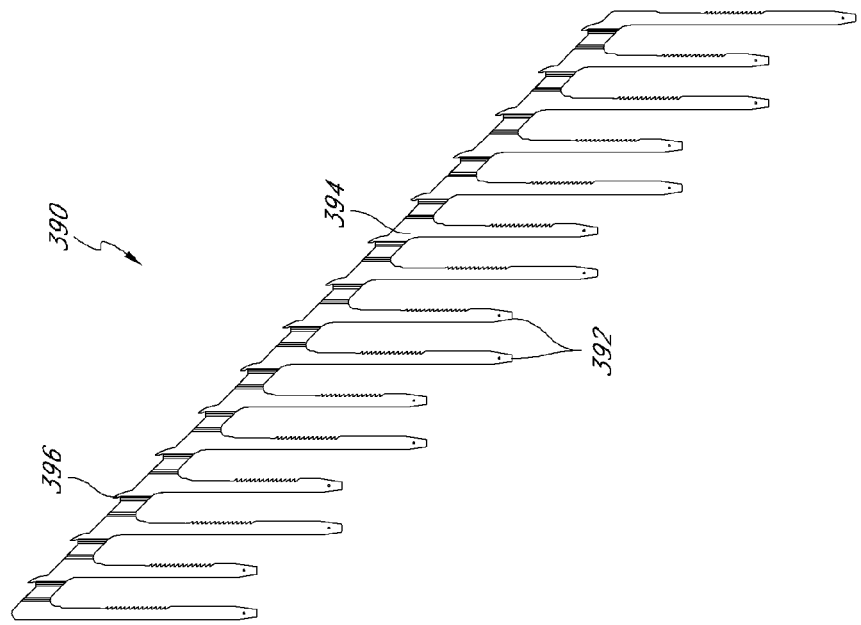
FIG. 24 is a planar view of a radial element of another embodiment, in a preconfigured orientation.
Figure 23:
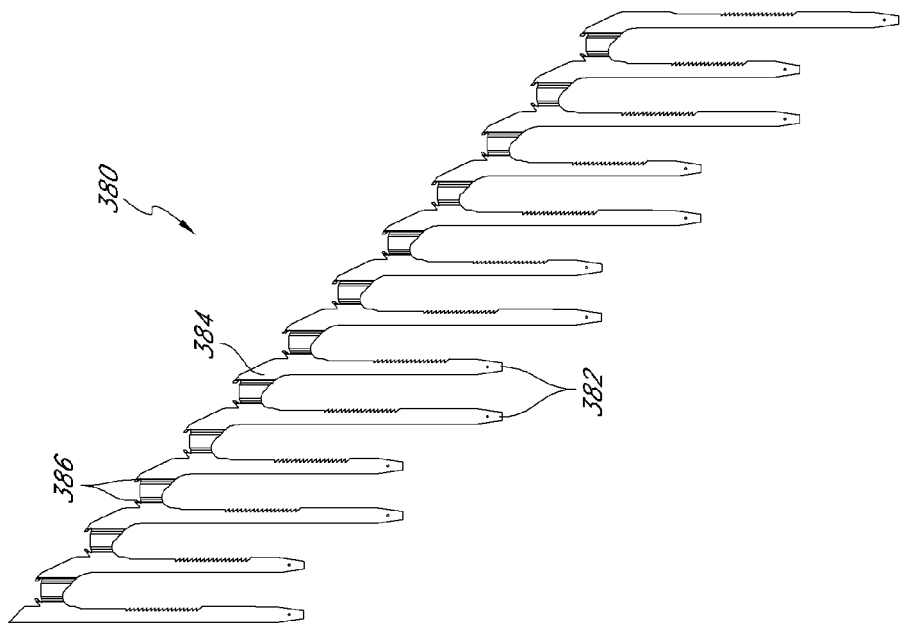
FIG. 23 is a planar view of a radial element of another embodiment, in a preconfigured orientation.
Figure 25:
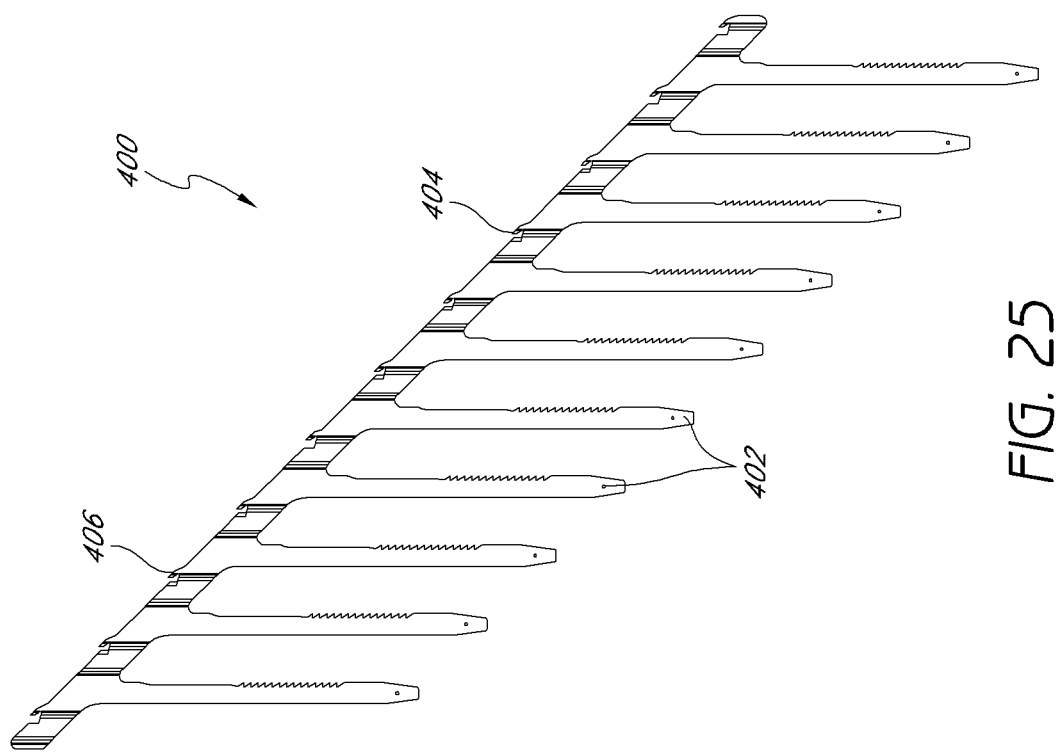
FIG. 25 is a planar view of a radial element of another embodiment, in a preconfigured orientation.

The fully captive slots 366 shown in FIG. 22 illustrate a single protruding deflectable tooth 372 adjacent to the top portion of the fully captive slot 366. It can be recognized by one having skill in the art, that certain features disclosed above can be interchanged to adapt the pattern to a particular use. Other variations of the above disclosed features are combined to illustrate the embodiments illustrated in FIGS. 23-25. FIG. 23 illustrates a radial element 380 having a paired elongate members 382, a stair-step backbone structure 384, and a dual tooth design 386 incorporated into the slot/locking mechanism. FIG. 24 illustrates a radial element 390 having a paired elongate members 392, a coiled backbone structure 394, and a single tooth 396 incorporated into the slot/locking mechanism. FIG. 25 illustrates a radial element 400 having elongate members 402 whose distal ends extend to along a helical or angled line to reduce hinging, a coiled backbone structure 394, and a single tooth 406 incorporated into the slot/locking mechanism. With these embodiments, one begins to recognize the potential for variations with respect to radial elements and ultimately to the stent.

The fully captive slots described above are further illustrated in FIGS. 26A-C. FIGS. 26A-C show perspective views of the radial element 400 shown in FIG. 25, including the fully captive slots 404 thereof. In this embodiment, the fully captive slot has a top portion 410, a bottom portion 412 and an inner surface. Adjacent to the top portion 410 of the fully captive slot 404 extends a deflectable tooth 406. The deflectable tooth 406 is adapted to engage with a conjugate locking member 420 from a slidably engaged elongate member or rail 422, and permit unidirectional slidable movement of the rail 422 through the substantially captive slot 404. FIG. 26B shows the ability of the deflectable tooth 406 to articulate from an extended configuration to a compressed articulation. As the rail 422 moves through the captive slot from the bottom portion to the top portion, the deflectable tooth 406 is deflected out. However, a rail attempting to move in a direction from the top portion 410 to the bottom portion 412 of the captive slot 404 will engage the deflectable tooth 406 and deflect that tooth 406 in to prevent further movement in the undesired direction. As such, the functionality between the embodiments of FIGS. 20A-C and 26A-C can be very similar, except that FIGS. 20A-C illustrates a dual tooth design while FIGS. 26A-C illustrate a single tooth design.

Figure 27C:
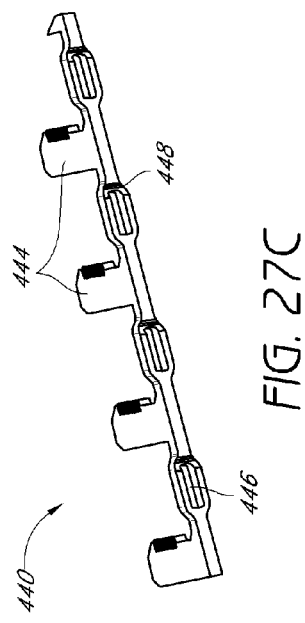
FIG. 27C is a magnified perspective of a top portion of the radial element of FIG. 27A, illustrating the features of the flexible backbone, captive slots, and elongate members.
Figure 27B:
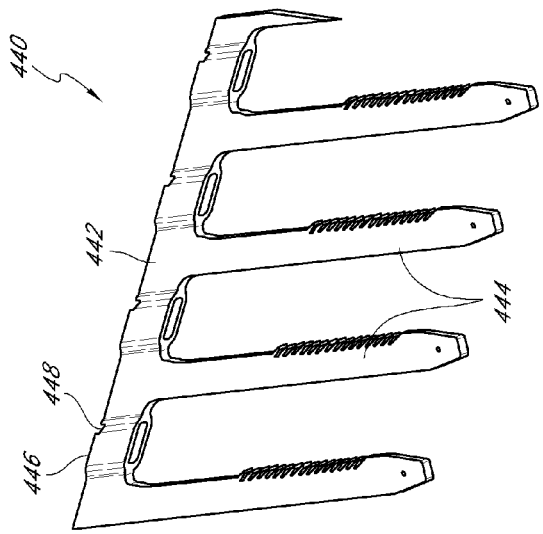
FIG. 27B is a magnified perspective of a bottom portion of the radial element of FIG. 27A, illustrating the features of the flexible backbone, captive slots, and elongate members.
Figure 27A:
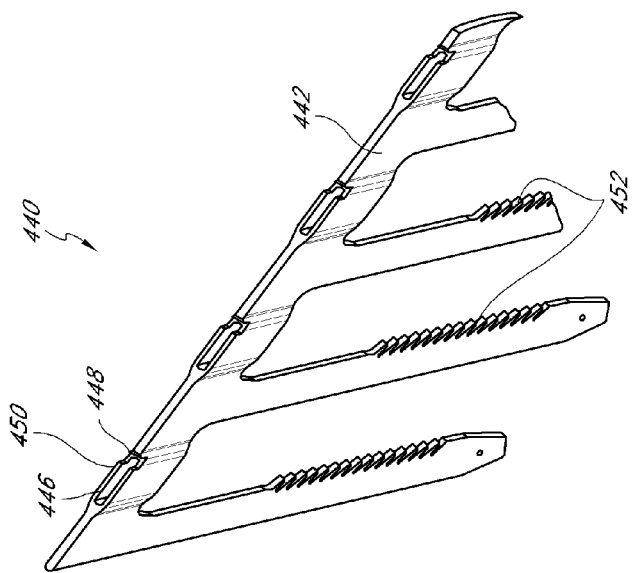
FIG. 27A is a magnified perspective of a top portion of another embodiment of a radial element illustrating features of a flexible backbone, captive slots, and elongate members.

FIGS. 27A-C illustrate yet another embodiment of a stent radial element 440 which comprises a flexible backbone 442, a plurality of elongate members 444, and a plurality of captive slots 446. The captive slots 446 of this embodiment comprise a stop 448 on a top portion 450 of the captive slot 446. The stop 448 in this embodiment can engage a tooth 452, especially a deflectable tooth to enforce unidirectional slidable motion from the bottom surface to the top surface.

Figure 28:
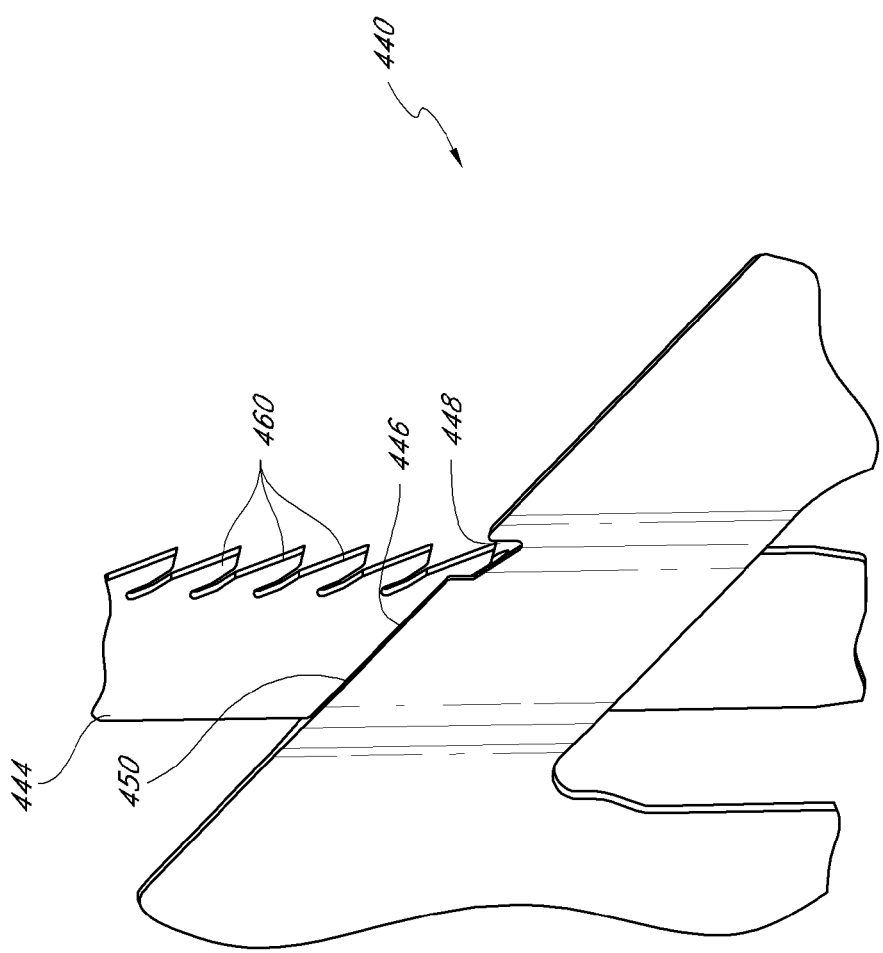
FIG. 28 is a perspective view of a captive slot slidably engaged with a rail, according to the embodiment shown in FIG. 27A-C.

FIG. 28 is a detailed view of the engagement of the rail 444 and the stop 448 of the radial element 440 shown in FIGS. 27A-C. In this embodiment, the rail 444 is shown having a plurality of deflectable teeth 460, and is slidably engaged with a substantially captive slot 446. One deflectable tooth 460 can be deflected on entry into the slot 446, i.e. from the bottom portion of the slot 446 as the tooth 460 enters the slot 446. Upon a tooth 460 leaving the top portion 450 of a slot 446, the deflectable tooth 460 is then configured to engage with the stop 448 located on the top portion 450 of the slot 446. This engagement provides improved unidirectional slidable movement of the rail 444 through the slot 446.

Figure 29A:
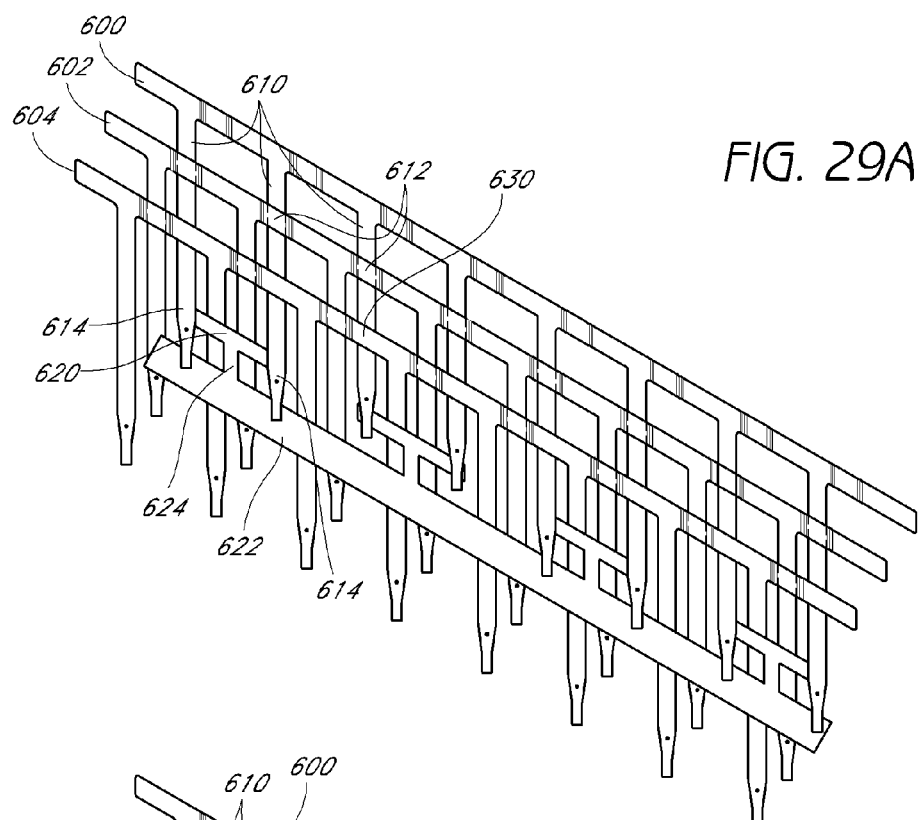
FIGS. 29A-B are planar views of a plurality of interconnected radial elements in during assembly steps in which ends of rails are being attached, according to an embodiment.
Figure 29B:
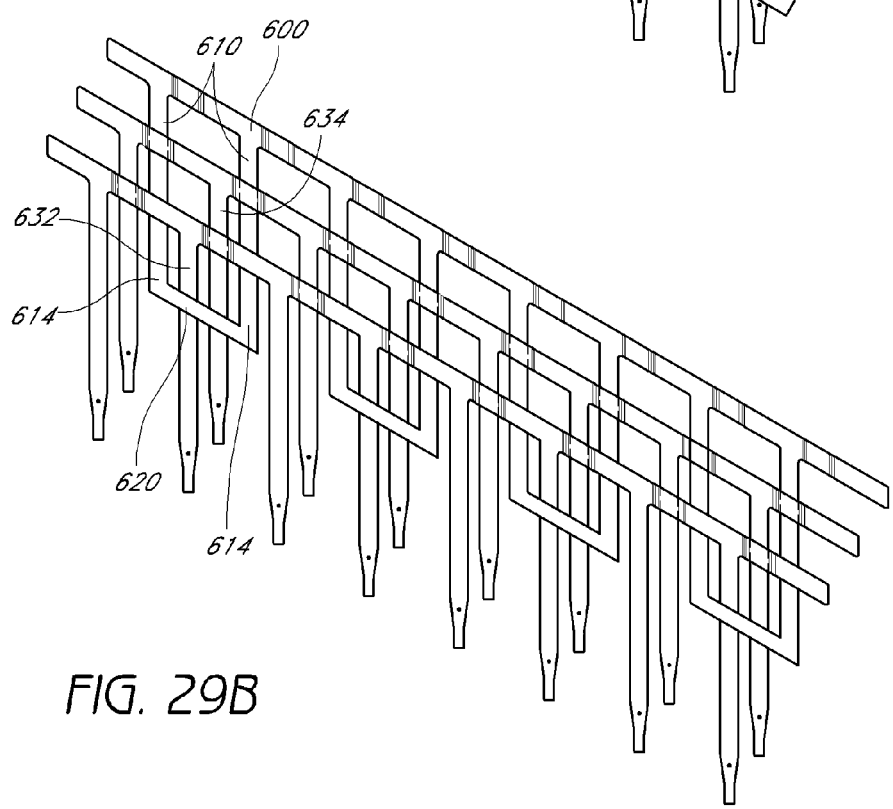

Referring now to FIGS. 29A-B, a method will now be described for manufacturing any of the tail-bonded stent embodiments disclosed herein. As shown in FIG. 29A, and as discussed herein, a plurality of radial elements 600, 602, 604 can be interconnected with elongate members 610 of a first radial element 600 being passed through slots 612 of a second radial element 602.

Subsequently, distal ends 614 of the elongate members 610 of the first radial element 600 can be interconnected. For example, in some embodiments, as shown in FIG. 29A, a crossbar 620 can be overlaid onto the distal ends 614 of a pair of adjacent elongate members 610. The crossbar 620 can be bonded to the distal ends 614, by mechanical bonding, adhesive bonding, or otherwise. For example, a solvent or adhesive bond, laser bonding, spot welding, ultrasonic bonding, and various other types of bonds can be formed to couple the crossbar 620 to the distal ends 614.

As also shown in FIG. 29A, the crossbar 620 can be placed using a carrier device 622. As illustrated, the carrier device 622 can comprise an elongate base to which a plurality of crossbars 620 are attached. In such embodiments, after the crossbar 620 has been bonded to the distal ends 614 of the elongate members 610, the carrier device 622 can be removed, such that the intermediate stent appears as shown in FIG. 29B. For example, it is contemplated that the carrier device 622 can be removed by using a blade, a laser, heat, or otherwise. In some embodiments a neck 624 connecting the crossbar 620 to the carrier device 622 can have a frangible or weakened zone that facilitates decoupling of the carrier device 622 by simple mechanical force or application of pressure at the neck 624. Thus, the distal ends 614 of the elongate members 610 can be interconnected by the crossbar 620.

Subsequently, the method can comprise interconnecting crossbars with distal ends of elongate members of other radial elements in a manner as described above. Depending on the size and configuration of the stent, various radial elements can be used. As shown in FIGS. 29A-B, for example, the elongate members of the second radial element 602 can be passed through the slots of the third radial element 604 and interconnected using crossbars, as described above with respect to the first radial element 600.

Further, in embodiments using three or more radial elements, it is contemplated that the elongate members 610 and the crossbar 620 can also be disposed or layered above a backbone 630 and elongate members 632 of a third radial element 604 and the elongate members 634 of the second radial element 602. Alternatively, the elongate members 610 and the crossbar 620 can also be disposed or layered beneath the backbone 630 of the third radial element 604 and the elongate members of the second radial element 602. In this manner, expansion of the stent can be unhindered as the elongate members 610 and crossbar 620 pass over or under the backbone 630 and the elongate members 632, 634.

Another feature of at least one embodiment disclosed herein is a slot having improved locking resolution, as disclosed in FIGS. 33-37. Further, a method for creating such a unique slot is also provided. The features and advantages of the slot can be incorporated into any of the stent embodiments disclosed herein, whether a "tail-bonded" stent as illustrated in FIGS. 1-29B or a "core-bonded" stent as illustrated in FIGS. 38-58.

Figure 30:
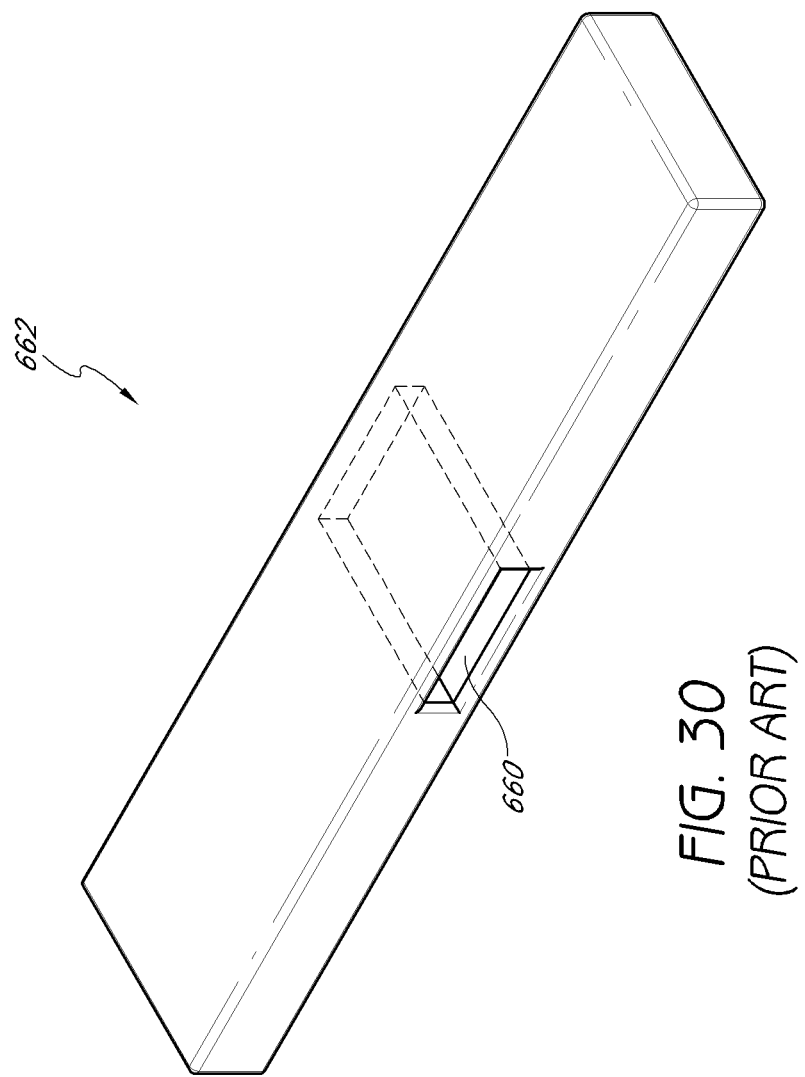
FIG. 30 is a perspective view of a prior art slot.
Figure 31:
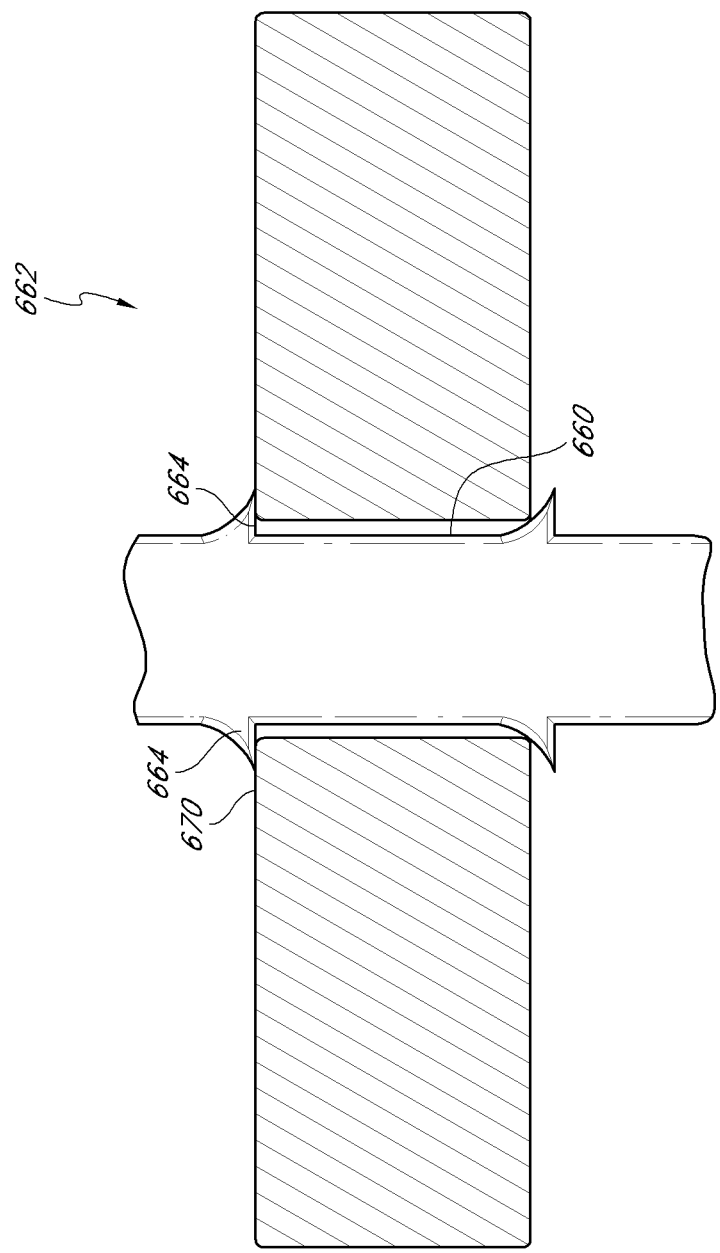
FIG. 31 is a cross-sectional top view of the slot of FIG. 30, illustrating locking resolution of the slot.
Figure 32:
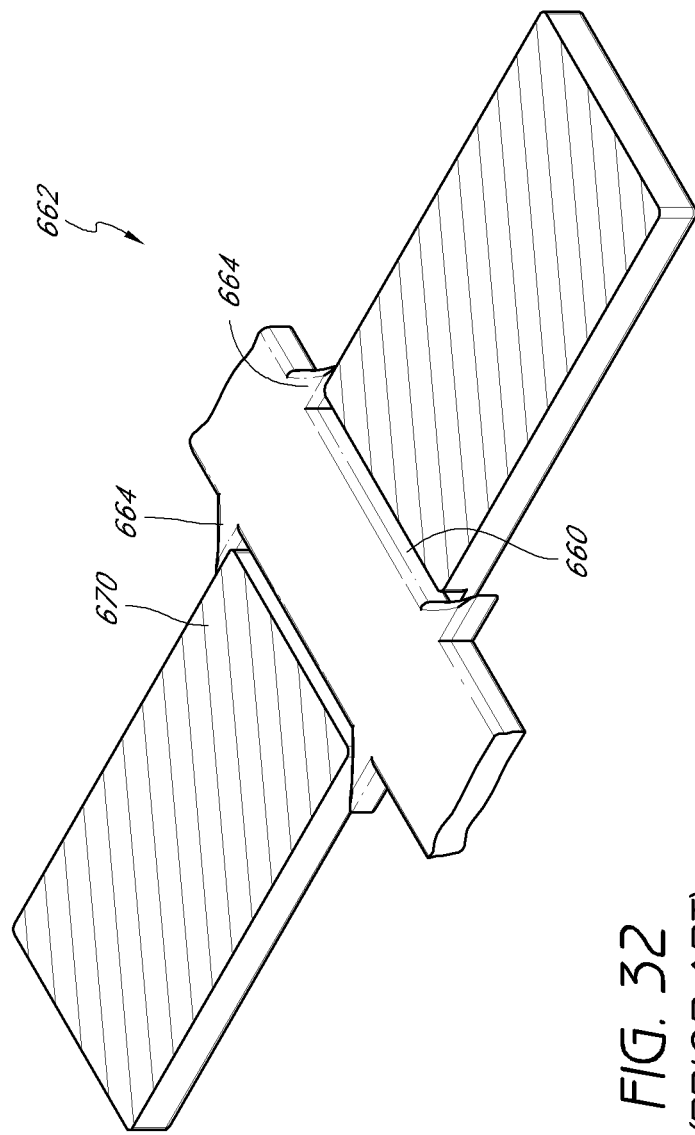
FIG. 32 is a cross-sectional perspective view of the slot of FIG. 30, illustrating locking resolution of the slot.
Figure 33:
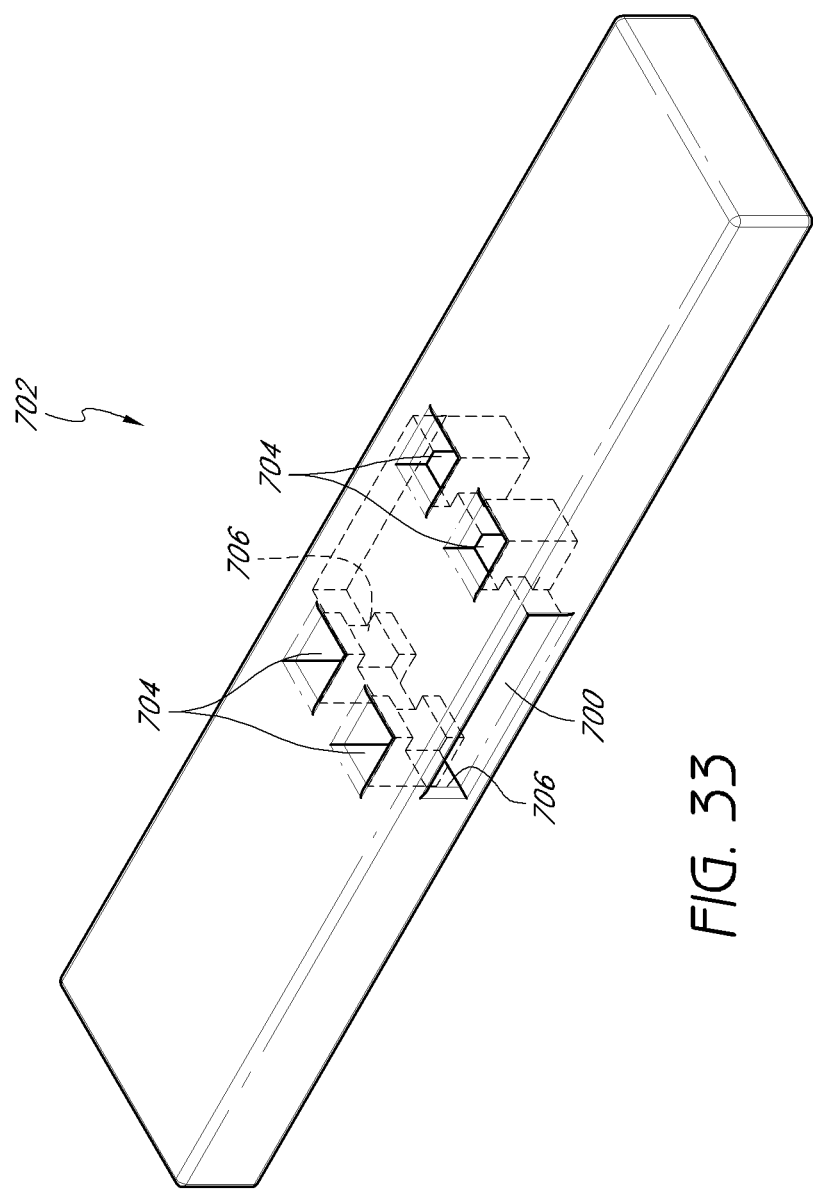
FIG. 33 is a perspective view of a captive slot having stops configured on the inner surface of the slot, according to an embodiment.
Figure 34:
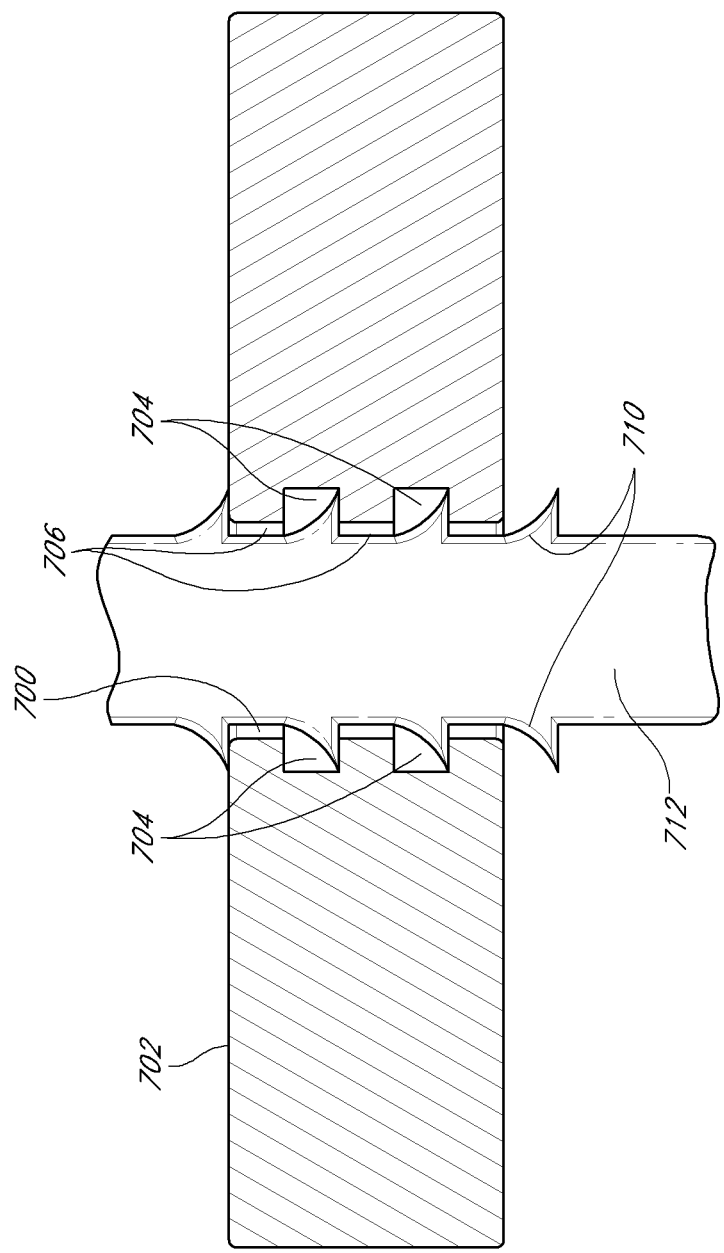
FIG. 34 is a cross-sectional top view of the slot of FIG. 33, illustrating locking resolution of the slot.

FIGS. 30-32 show a prior art locking mechanism or slot 660 formed in a rail member 662. The slot 660 has a resolution which is limited to the engagement created by a tooth 664 against a top surface 670 of the captive slot 660. Accordingly, the stress of the engagement is concentrated against the teeth 664. According to at least one of the embodiments disclosed herein is the realization that the use of a single pair of teeth 664 with the illustrated resolution (a single degree of resolution) can be problematic because a single tooth design 664 concentrates mechanical stresses and does not adequately protect against degradation of a polymer.

Therefore, in some embodiments, a slot configuration is provided that can enhance the resolution of the slot. Resolution can refer to the number of teeth or engagement members that participate in the engagement. In other words, resolution can define the manner and distribution of the stresses of the engagement. In this regard, it is contemplated that improvements in locking resolution can also permit improved customization of the diameter and configuration of the stent. Further, by improving the resolution of the slot, in some embodiments, a captive slot can be fabricated from a biodegradable polymer while maintaining the same advantageous structural properties as a slot formed in a metal stent. For example, a polymeric slot can be formed to comprise teeth and stops inside the captive slot that can experience slow degradation of the material with respect to the polymer surface which is exposed to the tissue and surrounding water.

One of the advantages of embodiments disclosed herein is that relatively slow degradation allows for long lasting mechanical lockouts relative to the life of the stent and prevents premature lockout failures. This is because most biodegradable polymers degrade by a process known as hydrolysis, the breakdown of ester bonds in the polymer. Based on the material properties of the biodegradable polymer, the polymer may absorb an amount of water. The degree to which water is absorbed, among other properties, will determine how the polymer degrades over time. A relatively higher rate of water absorption will likely result in bulk erosion of the polymer material, the polymer more or less degrades from the inside out. Alternatively a polymer designed to have a relatively lower water absorption rate will tend to degrade by surface erosion, or from the outside surface.

Therefore, in accordance with an embodiment, FIGS. 33-37 illustrate a slot 700 formed in a radial element 702. The slot 700 can have one or more stops 704 formed on the interior surface 706 of the slot 700. In this regard, the stops 704 can thereby provide improved resolution of engagements as well as minimized surface exposure and longer lasting mechanical engagements. These figures illustrate a number of stops 704 etched by laser or other mechanical means. These stops 704 provide a means for engaging teeth 710 inside the captive slot 700. In the embodiment illustrated by FIGS. 33-35, the stops 704 are distributed in a mirrored alignment, such that the stops 704 on both axial sides are arranged having equivalent distance from the top portion of the slot 700.

Figure 35:
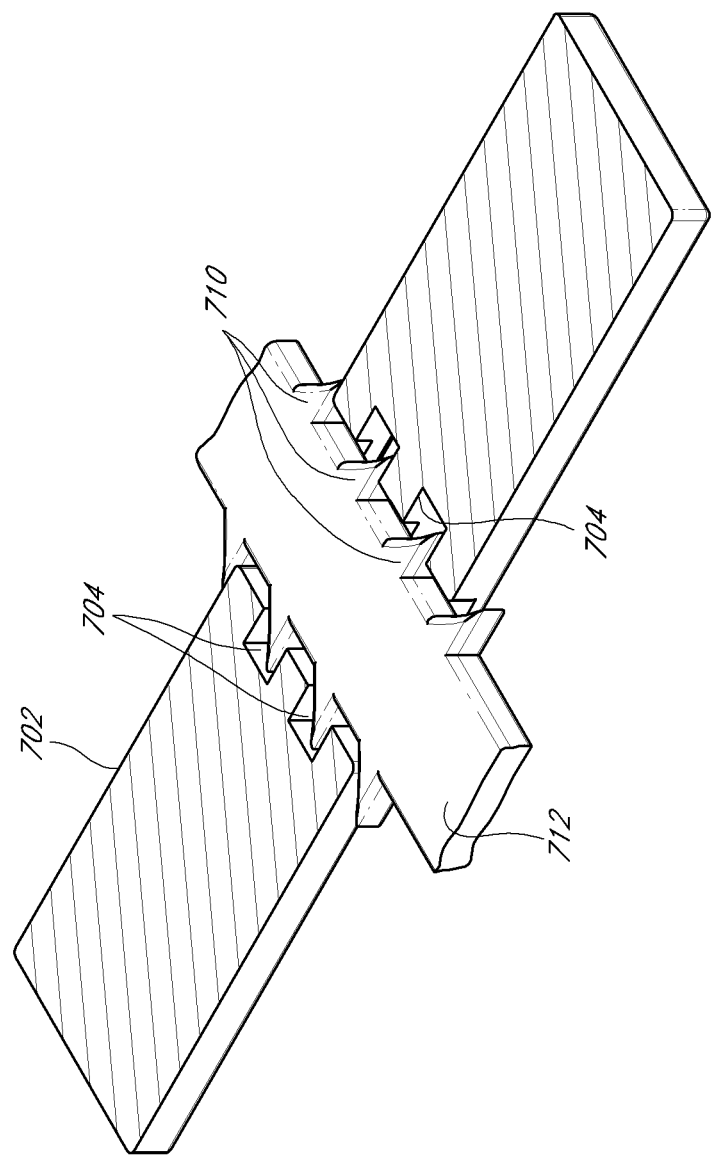
FIG. 35 is a cross-sectional perspective view of the slot of FIG. 33, illustrating locking resolution of the slot.

Thus, as shown in FIG. 35, the teeth 710 of a corresponding stent component 712 can be engaged by the stops 704. In contrast to the prior art slots which have low or only one degree of resolution, embodiments provided herein can provide high resolution, or several points of engagement along the length of the slot between the slot and the corresponding stent element. For example, a prior art stent shown in FIGS. 30-32 provide a single pair of teeth 664 that engage the slot 660. In contrast, the embodiments illustrated in FIG. 33-37 provide a plurality of pairs of teeth 710, 730 that can engage with a plurality of stops 704, 724.

Accordingly, in some embodiments, a method is provided for making a slot with improved resolution. One method of making stops is to etch, drill, or otherwise cut into the radial element so as to pass at least partially through the slot, creating a through space or aperture and one or more stops within the interior of the slot. For example, the through space or aperture can pass through the entire width of the radial element. In such an embodiment, the etching, drilling, or cutting is done in a direction that is transverse to the direction of the slot. In some embodiments, the direction of the etching, drilling, or cutting can be perpendicular to the direction of the slot. Another method is to bond a stack of sheets wherein the contained sheets are pre-etched. An advantageous method of etching is laser etching. In this manner, a series of interior stops can be formed within the slot for engaging a plurality of engagement members, such as teeth, of a corresponding stent component.

Figure 36:
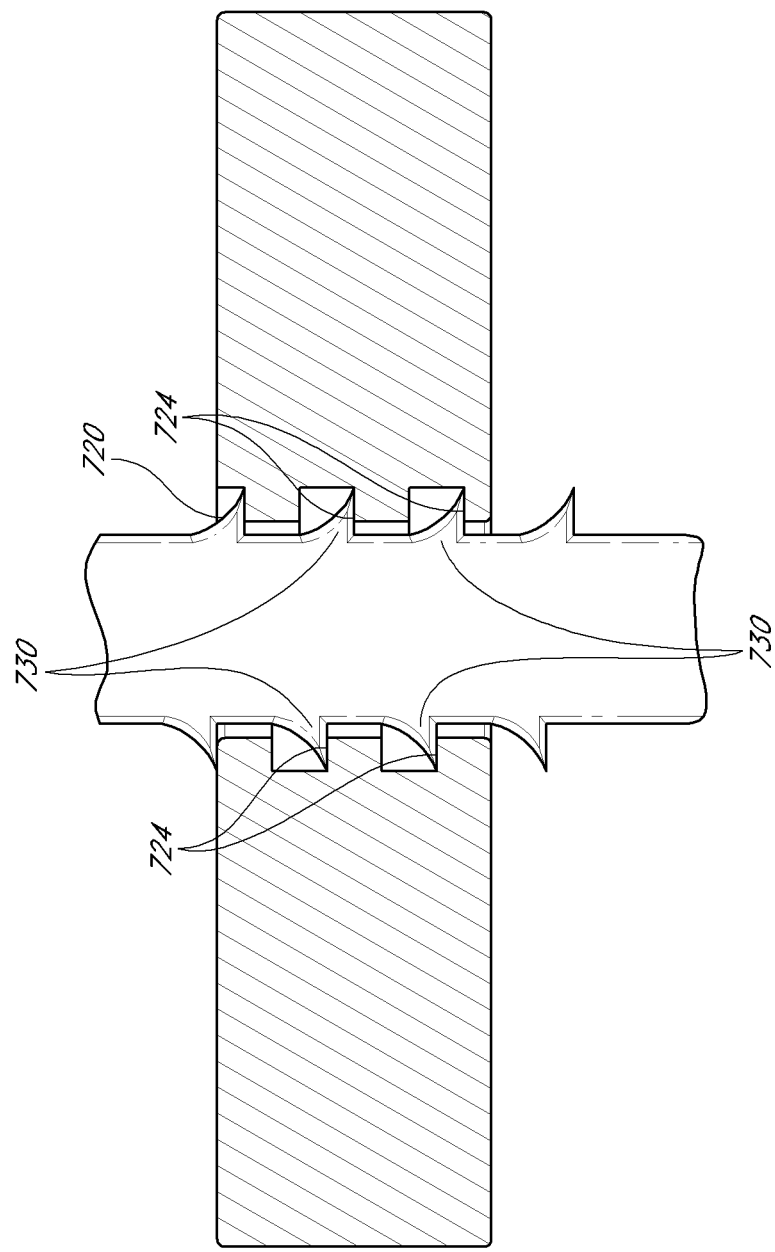
FIG. 36 is a cross-sectional top view of another embodiment of a slot, illustrating locking resolution of the slot.
Figure 37:
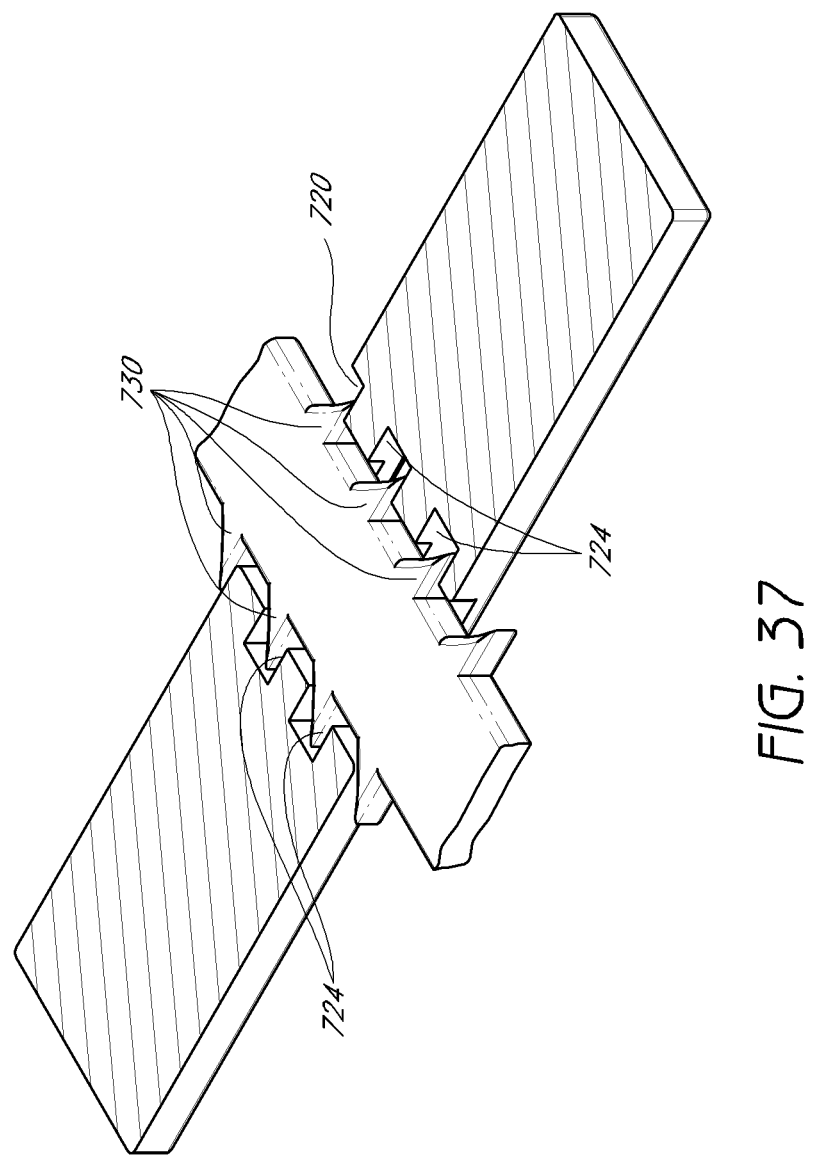
FIG. 37 is a cross-sectional perspective view of the slot of FIG. 36, illustrating locking resolution of the slot.

The embodiment disclosed in FIGS. 36-37 illustrate a slot 720 having stops 724 configured on the interior surface of the slot 724, the stops 724 are distributed on two axial sides, the stops 724 along a first axial side are offset with respect to the stops 724 on a second axial side. This offsetting of interior stops 724 provides further enhancement of resolution along with the aforementioned benefits of interior slots 724 such as longer lasting engagements with respect to a biodegradable material.

FIGS. 38-55B illustrate various aspects, structure and properties of a number of additional exemplary stent assembly embodiments, which are also useful for deployment in a body lumen. The body lumen may include any of the lumens of a vertebrate body within which a lesion, plaque, defect, constriction or anatomic structure is treatable with an expandable stent, as further described above.

FIGS. 38-58 relate to various embodiments of what can be referred to as "core-bonded" stents. In contrast to the embodiments described in FIGS. 1-29B, which relate to "tail-bonded" stents that are formed by bonding at the distal ends or tails of the rails of the radial elements, the "core-bonded"

embodiments of FIGS. 38-58 can be formed such that the rails of the stent are bonded at the backbone of the radial element.

As noted above, the various embodiments described herein can comprise a helical backbone assembly that provides a high degree of longitudinal structural integrity combined with longitudinal and rotational flexibility, both in the compacted and deployed configurations. The array of elongate members of the described embodiments engage to form an interwoven circumferential surface that provides crush strength and radial stiffness without unduly inhibiting longitudinal or rotational flexibility. The generally circumferential alignment of the rails allow the elongate members to engage each other and the backbone in a configuration which provides "hoop-strength" without coupling, thus providing a substantial increase overall longitudinal "beam" stiffness. In certain embodiments, the stent structure may be described as expandable flexible tubular multiple-spine "skeleton" assembly defined by the systematic movable interconnection of a plurality helical "backbone members" via a plurality of circumferentially arranged rail or "rib" elements.

With reference to FIGS. 38-58, such embodiments can include a helical array of longitudinal members or "backbone members" extending longitudinally, and a circumferential array of elongate or "rail" elements which are attached to and which engage the backbone members to form a highly expandable integrated stent assembly. As with the embodiments shown in FIGS. 1-29B, these additional embodiments of FIGS. 39A-55B have "slide and lock" functionality which permits a large range of expansion—from a compacted configuration suitable for advancement through the lumen, to an expanded configuration suited to the anatomy of a treatment site. The "slide and lock" or ratcheting functionality of the embodiments herein permits a large range of radial/circumferential expansion to be achieved without the need for plastic deformation of primary stent structural elements. The embodiments advantageously avoid the structural weakening and/or material damage demonstrated in many non-metallic or polymeric expandable stent designs of the prior art caused by the need to plastically deform or permanently bend structural elements to provide for the needed range of radial expansion.

Figure 43A:
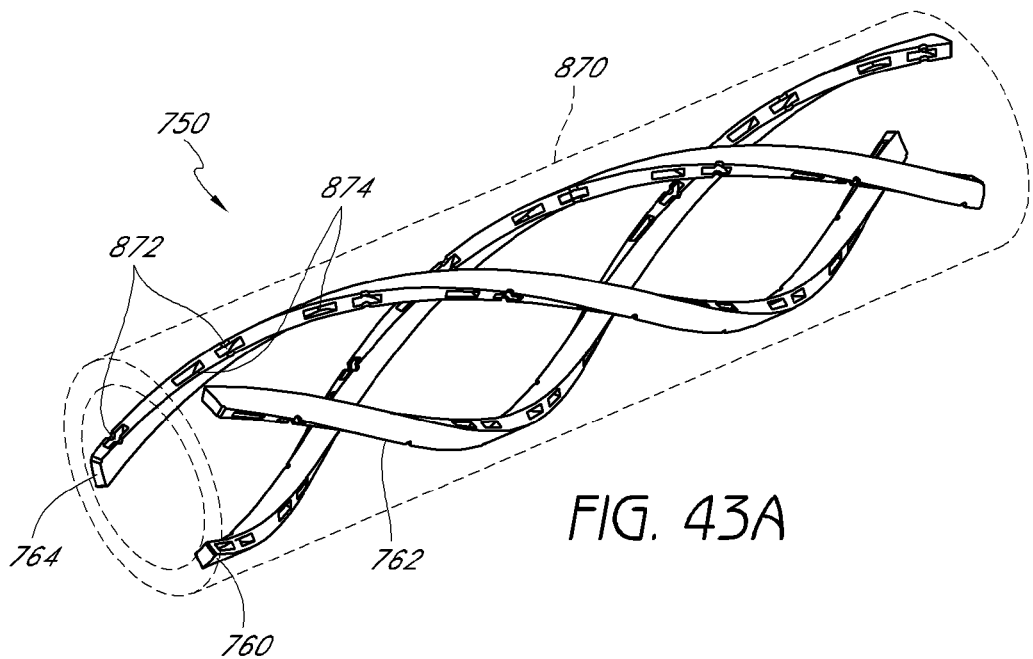
FIG. 43A is a perspective view of a backbone structure of a stent assembly disposed within a phantom body lumen, according to an embodiment.
Figure 43B:
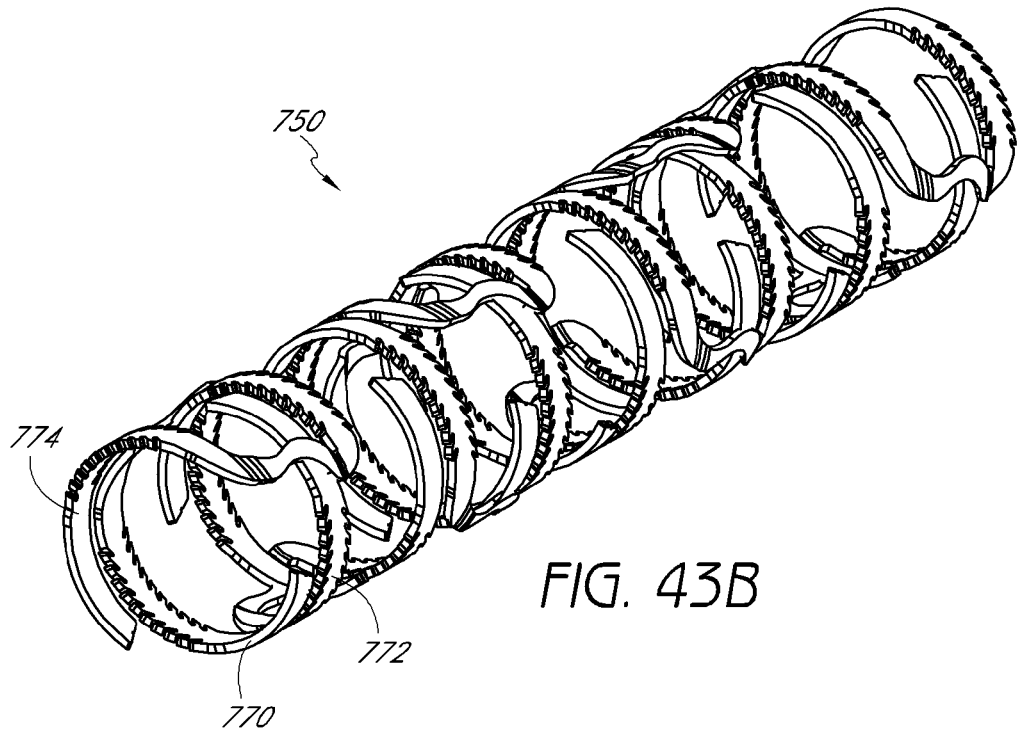
FIG. 43B is a perspective view of elongate members that can be used in combination with the backbone structure illustrated in FIG. 43A, according to an embodiment.
Figure 43C:
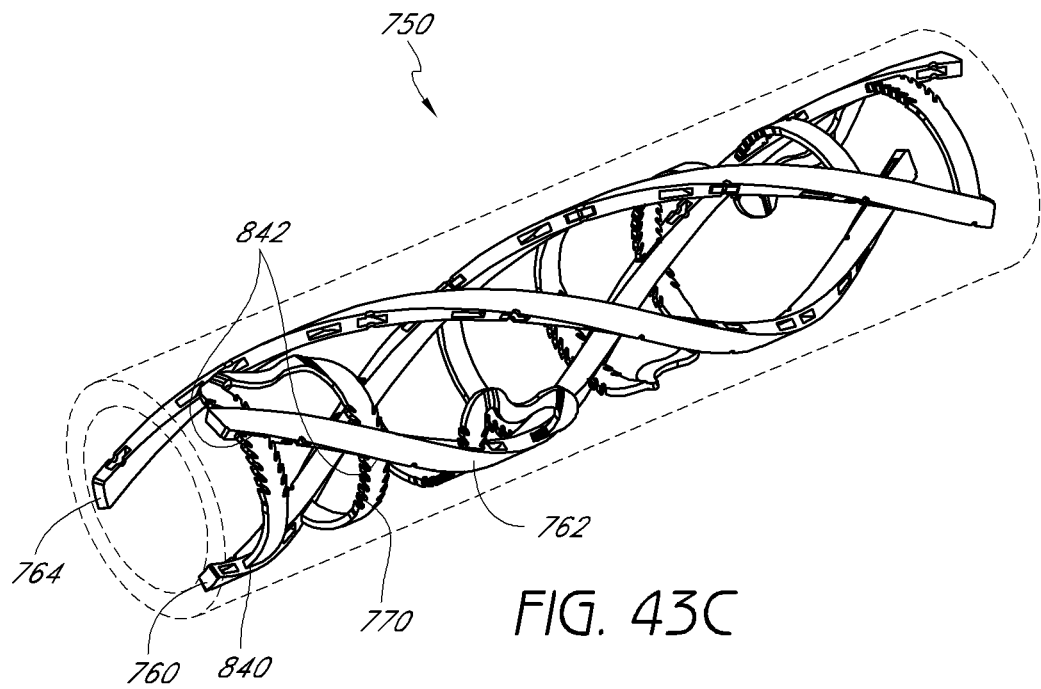
FIG. 43C is a perspective view of an elongate member of FIG. 43B in combination with the backbone structure of the stent assembly illustrated in FIG. 43A, according to an embodiment.

Advantageous structural properties of the embodiments disclosed herein—including the avoidance of plastic deformation, radial stiffness/strength without recoil, compact wall configuration, and longitudinal/rotational flexibility can allow the structural members comprising bioresorbable materials (such as polymers) to be sized so as to provide a selectably high ratio of wall opening area to overall stent circumferential surface (e.g., see FIG. 43C). These and other properties permit an optimized stent assembly providing for drug elution area, exposed lumen surface, bioresorbable structure and/or communication with lumen side branches, without sacrificing strength and deployment flexibility.

The stent structure may advantageously comprise a fracture-toughened polymer composition. For many treatment applications, it is desirable to have a bioresorbable stent structure, and it is also often desirable to have a radio-opaque structure facilitating medical imagery. For such applications, the backbone members and/or other elements of the stent may comprise a polymeric composition with is both bioresorbable and radio-opaque. See further description of such polymers above, and also U.S. Pat. Nos. 5,099,060; 6,120,491; and 6,475,477; and Patent Application Nos. 2005-0106,119 and 2006-0034,769, each of which is incorporated by reference. In various alternative embodiments, radio-opaque markers may be included which are distinct from the primary stent structural elements; certain structural elements may be radio-opaque; or a non-uniform material may be used have radio-opaque regions and radio-transmissive regions. Not all stent structural elements need comprise of the same material composition. Likewise, materials used may be isotropic or anisotropic, uniform or non-uniform, layered, and/or composite. Further, as discussed further below, various elements can comprise composite materials.

The described embodiments are readily manufacturable, as further described above. For example, members and elements of the stent structure may be cut from a sheet comprising one or more suitable biocompatible polymeric materials. The shaping of the structural members, and various slots and other details may be performed by known methods such as numerically-controlled laser cutting, or the like. The structural elements may comprise pharmaceutical agents or constituents which elute, upon stent deployment, into adjacent body fluids or tissues. Alternatively such pharmaceutical agents and compositions may be coated onto all or a portion of the stent assembly. In yet other alternatives, the stent assembly may include reservoir or storage elements containing pharmaceutical agents.

Figure 38:
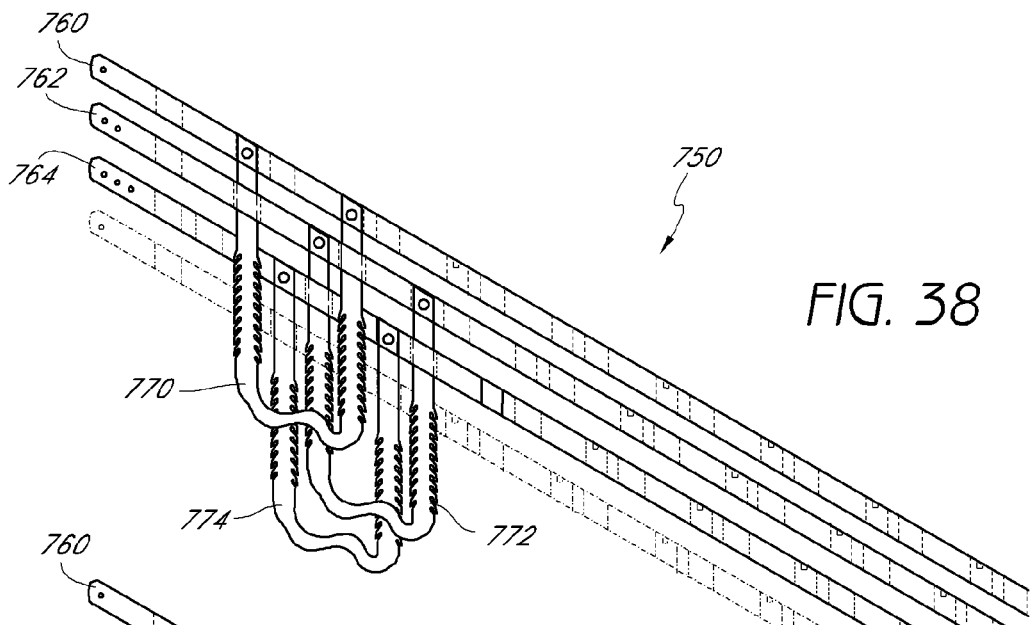
FIGS. 38, 39 and 40 are top views of an exemplary stent assembly illustrated in a planar configuration and in different degrees of expansion, according to an embodiment.
Figure 39:
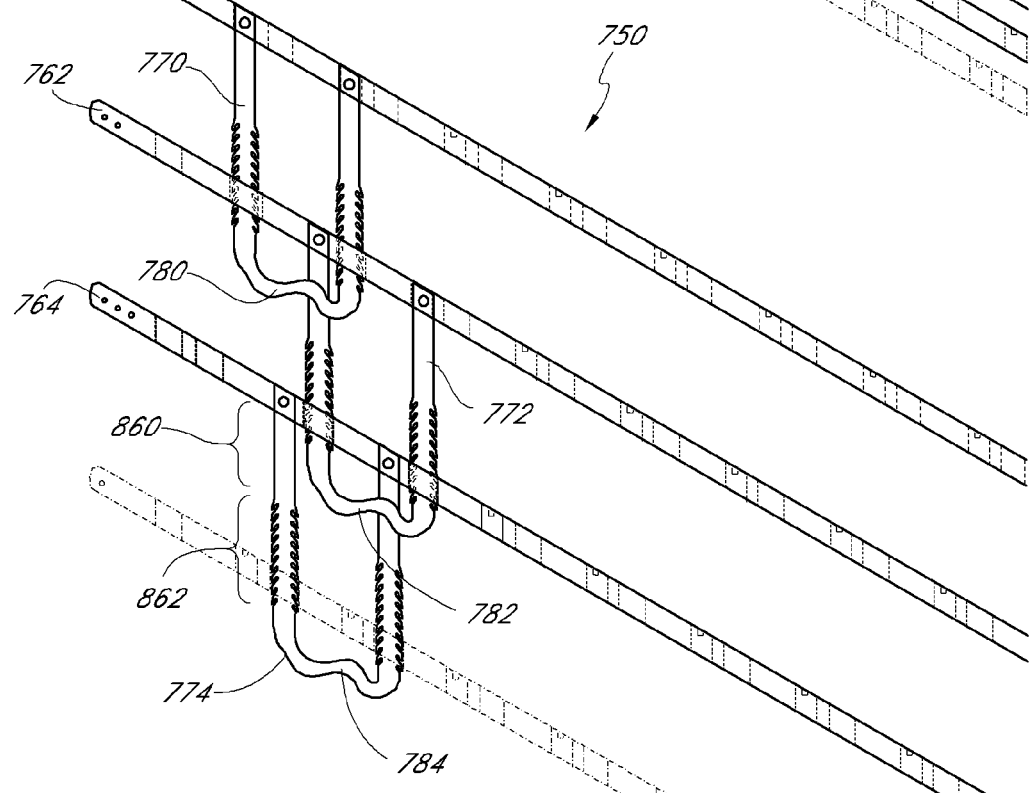
Figure 40:
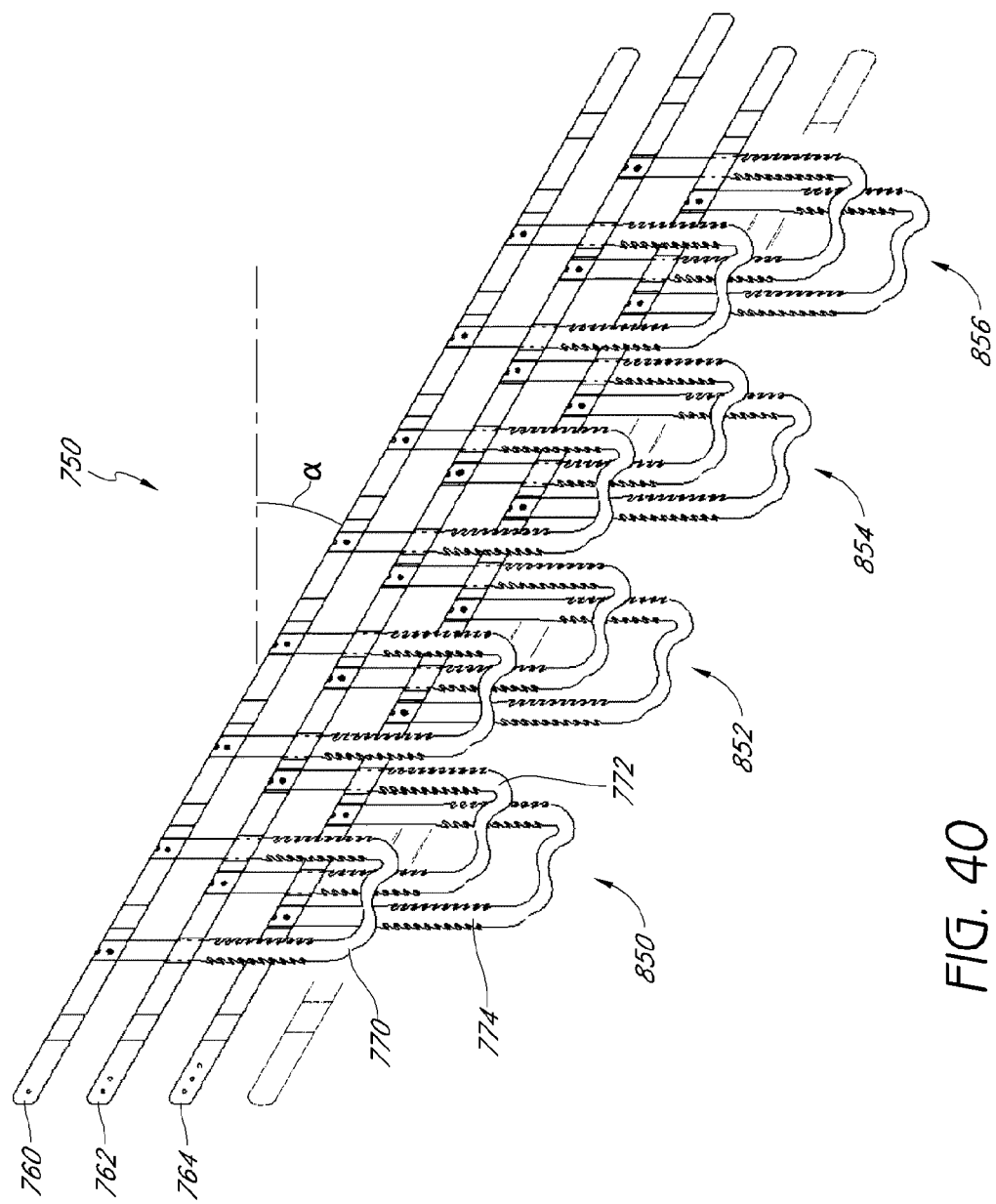

FIGS. 38, 39, and 40 show planar representations of a generally tubular circumferential surface of an embodiment of a stent or stent assembly 750. The stent assembly 750 is shown in various degrees of assembly and in an expanded or collapsed diameter in FIGS. 41A-43D. In each figure, a series of "backbone" members 760, 762, 764 are arrayed in a generally parallel manner so as to extend longitudinally within the circumferential surface.

The example shown includes three such backbone members 760, 762, 764, although the stent or stent assembly 750 may include fewer or more than three backbone members. The array of backbone members 760, 762, 764 are interconnected by a plurality of elongate members 770, 772, 774 which extend generally circumferentially so as to integrate the stent assembly 750, as is described further below.

Figure 42A:
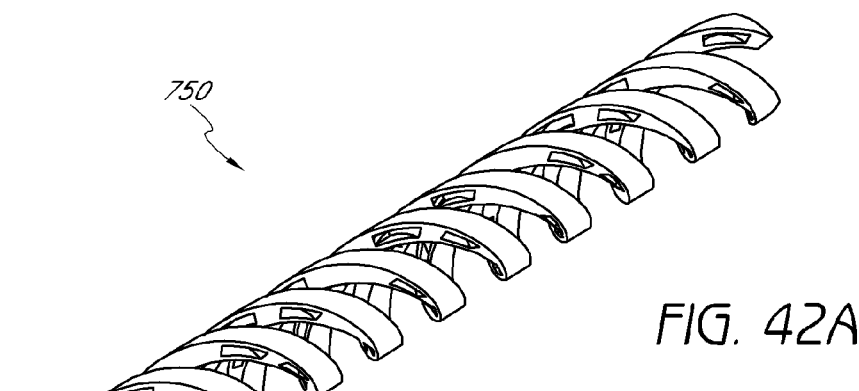
FIG. 42A is a perspective view of a backbone structure of a stent assembly in a collapsed configuration, according to an embodiment.

Although the backbone members 760, 762, 764 may be substantially parallel to the stent longitudinal axis, advantageously each backbone 760, 762, 764 may be disposed at an angle α to the longitudinal axis of the stent, so that when the backbones 760, 762, 764 are formed into a tubular member, the backbones 760, 762, 764 form a helical arrangement (see also FIGS. 42A and 43A). In each figure, the series of three backbone members 760, 762, 764 are shown together with a repeated image of backbone #1 in phantom lines to indicate extent of the corresponding circumferential tubular surface.

Figure 42B:
FIG. 42B is a perspective view of an elongate member in combination with a backbone of the stent assembly illustrated in FIG. 42A.
Figure 42C:
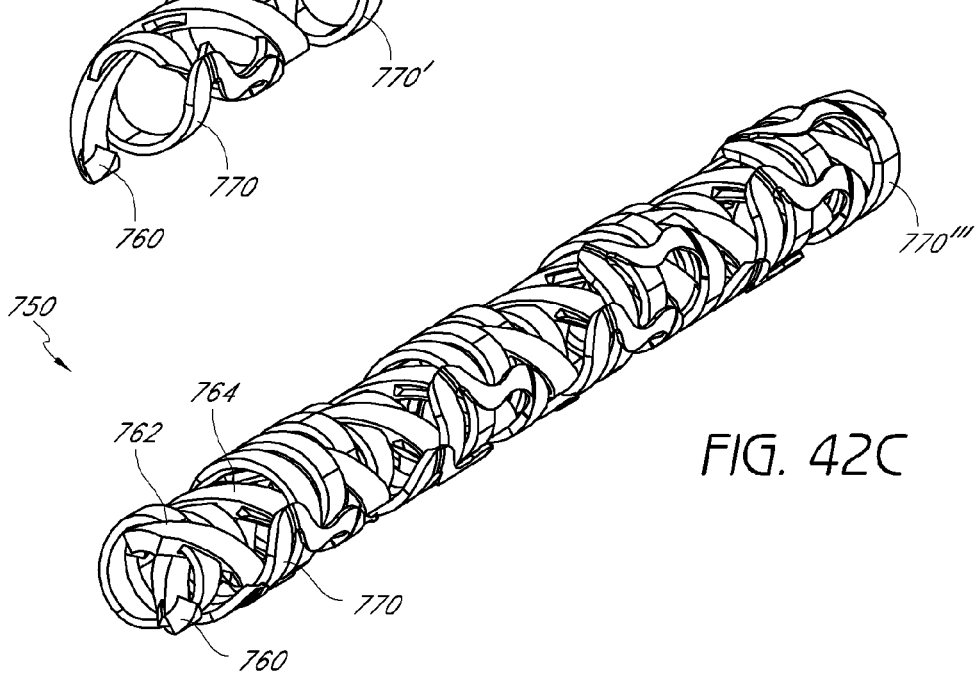
FIG. 42C is a perspective view of additional elongate members and stent structural members in combination with the stent assembly illustrated in FIG. 42B, in an assembled and collapsed state.

In FIG. 38, the series of three backbone members 760, 762, 764 are shown in a compacted arrangement in which the backbone members 760, 762, 764 are spaced apart from one another by a relatively small pitch, corresponding to a compacted circumference, which corresponds generally to FIGS. 42A-C. In FIG. 39, the series of three backbone members 760, 762, 764 are shown in an expanded arrangement in which the members are spaced apart from one another by a relatively large pitch, corresponding to an expanded circumference as shown generally in FIGS. 43A-D.

Note, when describing stent lumen expansion, the terms "radial expansion" and "circumferential expansion" are generally used interchangeably herein, as would be true for expansion having a consistently circular cross-sectional shape, or another constant cross-sectional shape. Where a stent is expanded with a change of general cross-sectional shape (e.g., from a circular compacted shape to an expanded irregular or flattened lumen profile; or other non-regular expansion) there may not be a linear relation between mean stent radius to stent circumference during expansion. Likewise, when a stent is deployed to conform to a flared, hour-glass, tapered or bulged lumen, the expanded cross-sectional shape may vary considerably along the longitudinal axis. Although not illustrated in the figures, the inventive principles of the embodiments may be applied to bifurcated stents or other complex configurations.

In FIGS. 38 and 39, a minimal set of overlapping elongate members 770, 772, 774 is depicted for simplicity and clarity of presentation (see also FIG. 40) to show an exemplary manner of interconnection between adjacent backbone members 760, 762, 764. In the exemplary embodiment shown, each elongate member 770, 772, 774 includes a generally parallel spaced-apart pair of elongate rails, connected at a distal end (with respect to corresponding backbone) by a crossbar 780, 782, 784 (see FIG. 39). In such an embodiment, the crossbars 780, 782, 784 are coupled to the elongate rails of the elongate members 770, 772, 774. Indeed, the crossbars 780, 782, 784 can be monolithically formed with the elongate rails of the elongate members 770, 772, 774 in such embodiments, which can be representative of and incorporated into the core-bonded and mid-rail bonded stent embodiments disclosed herein. However, as also disclosed herein, the crossbar can be formed separately from the elongate rails of the elongate members such that the crossbar is later attached to the elongate rails, which can be representative of and incorporated into the tail-bonded stent embodiments disclosed herein.

The crossbar can have any variety of configurations and cross-sections. For example, the crossbar can be shaped as a generally cylindrical member, a flat plate, or a combination of one or more shapes extending between the distal ends of the elongate members or rails. Further, the rails of the elongate members 770, 772, 774 can be configured to comprise a narrowed proximal portion that can attach to connection slots of a respective backbone for fixing the elongate member to the respective backbone. Furthermore, the rails of the elongate members 770, 772, 774 can also each comprise a distal or engagement section having one or more engagement members, such as teeth.

In use, the proximal narrow portion of the rail of each elongate member can be passed through a pass-through or engagement slot of a first backbone and then connected with connection slots of a second backbone. Thus, relative to the elongate member, the first backbone is slidably received onto the proximal portion of the rails of the elongate member. However, as the first backbone advances toward the distal or engagement portion of the rails of the elongate member, it is contemplated that the engagement members of the rail can engage with the pass-through or engagement slot of the first backbone.

Accordingly, the slot of the first backbone can be termed a pass-through slot insofar as it serves to permit passage of the rail of the elongate member therethrough; however, the slot of the first backbone can also be termed an engagement slot insofar as it engages with the engagement members of the rail of the elongate member. Further, the elongate members 770, 772, 774 may include a single rail, or more than two rails (e.g. three or more), and different elongate member configurations may be included in a single stent assembly.

As assembled, the proximal ends of the rails of a given elongate member 770, 772, 774 are connected to a single backbone member 760, 762, 764. In this manner, the elongate members 770, 772, 774 form a core-bonded stent assembly. For example, a given backbone member may include a connection slot to receive the proximal end of a given elongate member. The proximal end of the elongate member may be fixed to the backbone by a latching mechanism, an adhesive bond, a fastener or the like, or by a combination of these.

Figure 41A:
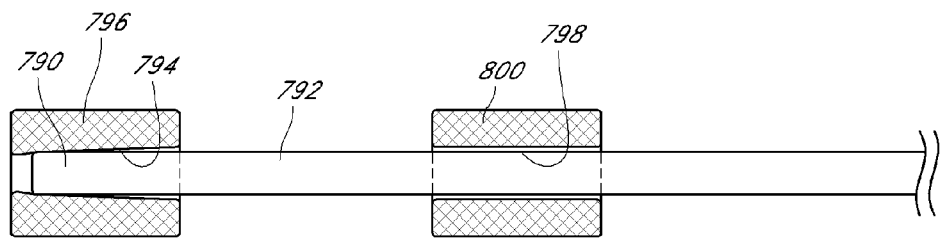

For example, as illustrated in FIG. 41A, a proximal end 790 of an elongate member 792 may be received in a connection slot 794 of a backbone 796. The connection slot 794 can provide an alignment or compression fit for securing the proximal end 790. In some embodiments, the alignment or compression fit can be temporary and can be followed by application of a suitable fluid adhesive, such as by capillary action, to permanently fix the proximal end 790 to the corresponding backbone 796. Further, FIG. 41A also illustrates that the backbone 796 can pass through a pass-through or engagement slot 798 of another backbone 800. In this regard, the backbone 800 of FIG. 41A can correspond to the backbone 762 of FIG. 38, and the elongate member 792 can correspond to the elongate member 770.

Figure 41B:
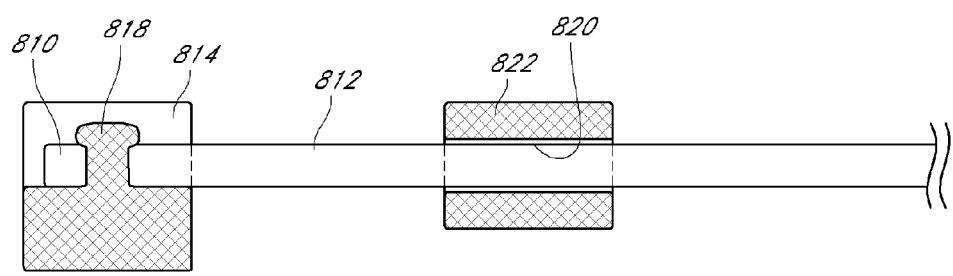

As shown in FIG. 41B, a proximal end 810 of a elongate member 812 can also be received into another connection slot 814 of a backbone 816. In this embodiment, a permanent latching mechanism or protrusion 818 may be included so as to obviate adhesive bonding. The protrusion 818 can be permanently fixed to an upper or lower surface of the connection slot 814. Note that where a slot is formed in the center region of the backbone (for example, as measured radially from the stent axis), there is little reduction in backbone beam stiffness or longitudinal bending strength, and no depth is added to the stent wall radial profile. Thus, this is a conveniently manufacturable, structurally efficient and compact arrangement. Further, FIG. 41B also illustrates that the backbone 816 can pass through a pass-through or engagement slot 820 of another backbone 822. In this regard, the backbone 822 of FIG. 41B can correspond to the backbone 762 of FIG. 38, and the elongate member 812 can correspond to the elongate member 770. Note that in the latter example, the backbone 816 may be recessed.

Figure 41C:
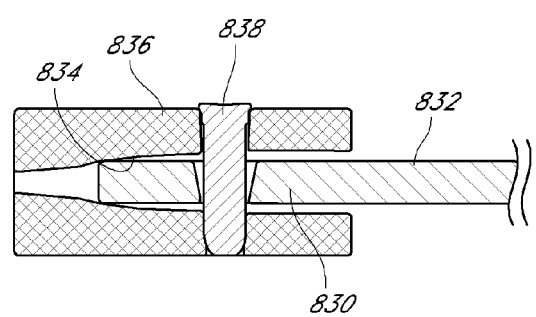

In an alternative example illustrated in FIG. 41C, a proximal end 830 of a elongate member 832 may be fixed in place relative to a connection slot 834 of a backbone 836 by placement of a locking pin 838 therethrough. In particular, the locking pin 838 can be passed through the proximal end 830 of the elongate member 832 and through the upper and/or lower surface of the backbone 836. If desired, further bonding (e.g., by spot or laser welding) can be performed by means chemical, mechanical, or an adhesive means.

FIGS. 41D-E illustrate alternative core-bonding techniques and structures that can be implemented in some embodiments. Both FIGS. 41D-E illustrate an elongate member 840 that extends through a connection slot or aperture 841 of a backbone member 842. However, in FIG. 41D, a distal end 844 of the elongate member 840 is deformed against an end 843 of the backbone 842 to create a riveted end 846. In FIG. 41E, an end cap 848 can be attached to the distal end 844 of the elongate member or radial element 840 adjacent to the end 843 of the backbone 844. Thus, in such embodiments, the distal end 844 of the elongate member or radial element 840 is fixed relative to the backbone 842.

FIGS. 42A-C illustrate a compacted configuration of various components of a stent. For example, FIG. 42A illustrates the plurality of helical backbones 760, 762, 764 in a compacted configuration. FIG. 42B illustrates a plurality of elongate members 770, 770', 770'', 770''' that are coupled to a first helical backbone 760 in the compacted configuration. Finally, FIG. 42C illustrates the completed stent 750, with the plurality of helical backbones 760, 762, 764 and elongate members (such as 770 and 770''') coupled with the backbones, in the compacted configuration.

In the compacted configuration of FIGS. 38, 40, and 42A-C, and taking backbone 760 and elongate member 770 as illustrative examples, it may be seen that the rail ends of elongate member 770 are fixed to backbone 760 at a connection slot. The adjacent elongate sliding portion or rail of each elongate member 770 passes through a companion sliding or "pass through" slot in adjacent backbone 762 (see also FIGS. 41A, 43A, and 43C), so as to interconnect the elongate members 770 with partial restraint to backbone 762. In this manner, the motion of each such rail of element 770 is thus restrained in one or more degrees of freedom with respect to backbone 762 while yet being free to move in at least a circumferential degree of freedom with respect to backbone 762.

Figure 43D:
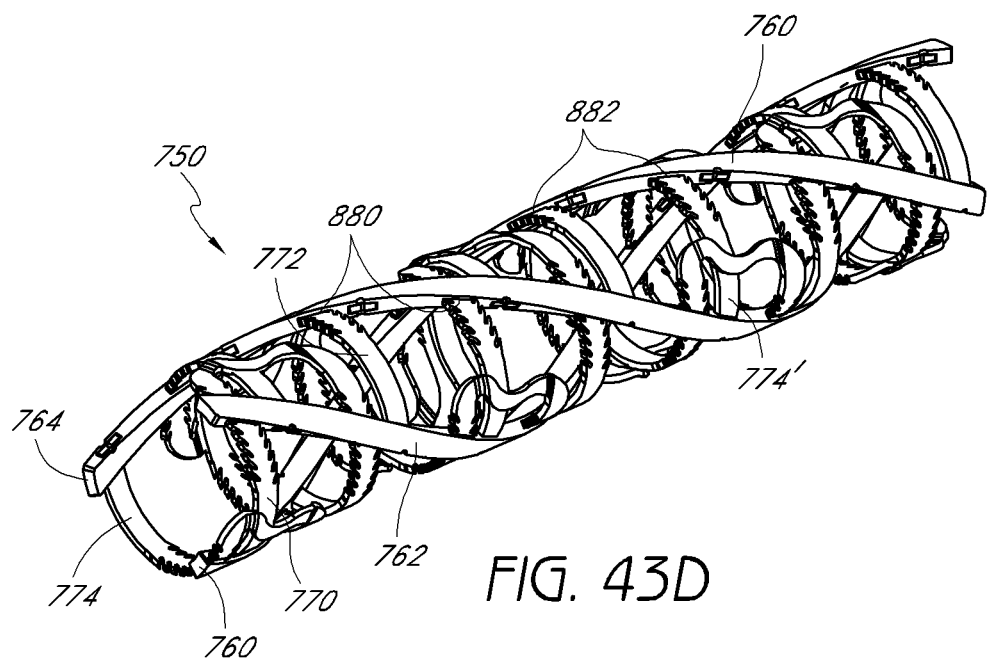
FIG. 43D is a perspective view of all of the elongate members of FIG. 43B and stent structural members of FIG. 43A, in an assembled and expanded state, according to an embodiment.

FIGS. 43A-D illustrate an expanded configuration of various components of the stent shown in FIGS. 42A-C. For example, FIG. 43A illustrates a plurality of helical backbones 760, 762, 764 in an expanded configuration. FIG. 43B illustrates a plurality of elongate members in the expanded configuration. FIG. 43C illustrates the three helical backbones 760, 762, 764 and a plurality of elongate members 770 interacting with the first and second helical backbones 760, 762 in the expanded configuration. In particular, the proximal ends of the elongate member 770 are attached to connection slots 840 of the backbone 760 while the elongate members 770 also pass through engagement slots 842 of the backbone 762. Finally, FIG. 43D illustrates the stent 750, with the plurality of helical backbones 760, 762, 764 and elongate members 770, 772, 774 coupled with the backbones 760, 762, 764, in the expanded configuration. It can be appreciated that teeth of the elongate members 770, 772, 774 can engage the engagement slots of the respective backbones 760, 762, 764 to maintain the stent 750 in an expanded configuration.

One may see that alternative partially-restraining engagement mechanisms between elongate member 770 and backbone 762 may be included in substitution for the sliding pass-through or engagement slot shown, for example, by including a mechanism having an alignment pin engaged in a longitudinal slot. However, it has been demonstrated that the partially-restraining engagement mechanism shown (a rail sliding portion passing through a simple transverse backbone slot with a selectable clearance) functions well for this purpose; is structurally simple, compact and robust; and may be produced and assembled by known manufacturing methods.

In reference to the configurations of FIGS. 38 and 39, it may be seen that a yet more distal portion or engagement portion of each elongate member 770 ("ratchet rail portion") is configured for ratcheting and/or locking engagement with backbone 762. The engagement portion can comprise one or more teeth, as illustrated. As the circumference of the stent surface is increased between the compacted and expanded configurations (e.g., by an expanding axial balloon catheter), it may be seen that the ratchet rail portion of each elongate member 770 progressively becomes engaged with pass-through or engagement slot in backbone 762, so that a ratcheting and/or locking engagement is achieved, so as to prevent or resist re-compaction or "recoil" of the expanded stent assembly. The teeth may be configured in a directionally biased barb-like configuration to permit sliding through the slot when urged in the expansion direction (increased circumference)—e.g., by deflecting slightly inward—and to engage the slot surface and lip so as to resist or lock when urged in the compaction direction (reduced circumference).

In the example shown, the teeth can be configured to extend axially within the stent circumferential surface sufficiently to fill the lateral clearance between rail and slot (an advantageously compact arrangement), but the teeth or barbs may alternatively or additional be disposed to extend in a radial direction.

One may see that alternative ratcheting and/or locking engagement mechanisms between the ratchet rail portion of element 770 and backbone 760 may be included in substitution for the sliding pass-through or engagement slot shown. For example, a ratcheting mechanism structurally independent of the pass-through or engagement slot may be included. However, it has been demonstrated that the ratcheting engagement mechanism shown (a series of laterally disposed teeth or barbs in the rail extending to engage the inner surface and openings of the pass-through or engagement slot) functions well for this purpose, and is simple and compact, permitting convenient manufacturing and assembly.

In the example shown in FIGS. 38 and 39, the three illustrated elongate members 770, 772, 774 extending from the respective adjacent backbones 760, 762, 764 overlap each other in sequence with an offset, so as to form a shingle or fish scale effect. In some embodiments, the crossbar 780, 782, 784 of each may be crimped or recessed at each point of overlap so as to permit a more compact configuration. The overlapping configuration also supports the extended elongate members via the crossbars so as to obviate any intrusion by distal rail ends into the central lumen of the stent, either during assembly or after deployment.

As shown in FIG. 40, a plurality of sets 850, 852, 854, 856 of overlapping elongate members (e.g., the set 850 includes the elongate members 770, 772, 774, and the other sets 852, 854, 856 can be similarly configured) may be mounted and configured along the longitudinal extent of the array of backbones 760, 762, 764, so as to form a generally continuous expandable tubular "woven" surface. Subsequently, the surface can be formed into a tubular member, as discussed herein. The size and density of the backbones 760, 762, 764 and elongate members 770, 772, 774 may be selected so as to create a desired ratio of solid surface to tubular area in the configuration of the expanded/deployed stent.

Additionally, embodiments of the stent, such as that shown in FIG. 40, can be configured such that helical backbone extends at a generally constant or fixed radius. In other words, the stent can define a generally constant diameter in an expanded state. However, it is also contemplated that any of the embodiments disclosed herein can provide a stent that has a variable diameter in an expanded state. Thus, one or more helical backbones of the stent can be spaced at a variable distance from a longitudinal axis of the stent.

Moreover, it is also contemplated that in some embodiments, one or more of the helical backbones can be oriented at a given helix angle $\alpha$ relative to the longitudinal axis of the stent. For example, the helix angle $\alpha$ can be between about 20° and about 80°. More specifically, the helix angle $\alpha$ can be between about 30° to about 60°. In some embodiments, the helix angle $\alpha$ is about 45°. As such, the elongate members or rails can extend from the helical backbone in a circumferential direction at a coupling angle (the acute angle formed between the backbone and the elongate member or rail) that is less than 90°. In other words, the elongate members or rails of some embodiments are not oriented perpendicularly relative to the backbone. For example, the coupling angle can be between about 30° to about 80°. However, the coupling angle can be between about 40° to about 70°. In some embodiments, the coupling angle is about 45°.

In this regard, it is contemplated that by adjusting the helix angle and the coupling angle, embodiments can be optimized to provide a desirable stiffness and other structural properties.

With reference again to FIG. 39, it is contemplated that the length of a sliding rail portion 860 of the elongate member 774 (and other elongate members 770, 772 also have similar sliding rail portions with lengths that can correspond to each other or be different from each other in some embodiments) may be selected to provide a desired degree of circumferential expansion from a compacted state to the point of first ratchet engagement. This permits a highly compacted stent configuration facilitating advancement of the stent on a deployment device through a tortuous body lumen (e.g., a rapid exchange balloon catheter or like device). Note that this selectable range of expansion is achieved without plastic deformation of the material or materials from which stent elements are comprised (e.g., a bioresorbable polymer).

Similarly, with reference again to FIG. 39, the length of the ratchet rail portion 862 of the elongate member 774 (other elongate members 770, 772 also have similar ratchet rail portions with lengths that can correspond to each other or be different from each other in some embodiments) may be selected to provide a desired range of deployed configurations. Advantageously, this range permits a physician to deploy a given stent in a range of lumen sizes, providing treatment flexibility. Also, different longitudinal portions of a stent assembly may be expanded and locked or ratcheted to different final diameters, permitting deployment of the stent in a tapered, bulged or flared configuration, or the like, so as to suit the anatomic shape of the target lumen.

Thus, in accordance with an embodiment, a stent is provided that can comprise at least first and second radial elements. The radial elements can each comprise a helical backbone member and at least one elongate member. Further, the elongate member of the first radial element can be disposed through a pass-through or engagement slot of a helical backbone member of a second radial element such that the first and second radial elements form a tubular stent. Further, the elongate member can comprise a sliding rail portion and a ratchet rail portion. The sliding rail portion is configured to allow the helical backbone member of the second radial element to slide freely relative to the elongate member. Additionally, the ratchet rail portion is configured to promote engagement between the helical backbone member of the second radial element and the elongate member for maintaining the stent in at least one expanded position or diameter. In some embodiments, the lengths of the sliding rail portion and the ratchet rail portion can be configured to allow for various ranges of flexibility and/or expansion. Further, in other embodiments, a proximal portion of the elongate member can be attached to the helical backbone at a connection slot thereof.

Note with respect to the expanded configuration of FIG. 39 that the crossbar 780 of elongate member 770 can, if desired, optionally function as a fixed mechanical stop preventing over-expansion and/or disengagement of the elongate member 770 from the backbone 762. In this regard, at a given separation distance between the backbones 760, 762, the crossbar 780 will contact the backbone 762 to pervert further expansion. Alternatively and optionally, a mechanical stop may be formed as part of one or more of the distal rails (for example, along the ratchet rail portion 862 of elongate member 774) so as to prevent entrance of the rail distal end into the backbone slot.

As discussed above, FIGS. 43A-D show an embodiment of a stent or stent assembly 750 illustrated in perspective view as deployed within a phantom body lumen, showing both selected subsets of the stent structure and an assembled stent.

FIG. 43A shows a helical array of three backbone members 760, 762, 764 as arranged in a phantom body lumen 870, the backbone members 760, 762, 764 being space apart in a generally uniform pattern around the circumference of the lumen 870. Note that the backbones 760, 762, 764 need not be identical in form, and may have differing arrangements of slots and/or other details to provide for mounting of a staggered or offset pattern of elongate members as indicated in FIGS. 39-40. The backbone members 760, 762, 764 may have different lengths, such as to provide for mounting of specialized terminal elongate members at either or both ends of the stent (see also FIG. 43C). The backbone members 760, 762, 764 may have a generally rectangular cross section as shown in FIG. 43A, or may be of non-rectangular in cross section. Note the slot openings 872, 874 formed in the members (e.g. connection slots 872 and pass-through or engagement slots 874 formed in the backbone 764).

FIG. 43C shows the helical backbones 760, 762, 764 of the stent assembly 750 with a plurality of elongate members 770 attached to backbone 760, each elongate member 770 passing though a companion sliding slot 842 in the backbone 762 (in the expanded configuration, the rail teeth or barbs are shown engaged in the corresponding slot). In some embodiments, the terminal (or left-most) elongate member 770 can be of an alternative and optional triplet configuration, such that the left-hand rail of the triplet passes longitudinally beyond the backbone 762 rather than through a slot in the backbone 762.

FIG. 43D shows the fully assembled stent 750 of FIGS. 43A-C, including a plurality of elongate members 772 attached to the backbone 762, passing through corresponding pass-through or engagement slots 880 in the backbone 764. Further FIG. 43D also illustrates an additional plurality of elongate members 774, 774' attached to the backbone 764, passing through corresponding pass-through or engagement slots 882 in backbone 760. As shown in FIGS. 38-40, the sets of elongate members 770, 772, 774 attached to each respective backbone member 760, 762, 764 overlap the respective elongate members 770, 772, 774 attached to the adjacent respective backbone. Further, the plurality of sets of elongate members 770, 772, 774 can be arranged as rows of circumferentially wrapped shingles or scales. As discussed herein, embodiments can be provided in which the crossbars 780, 782, 784 of the elongate members 770, 772, 774 may be shaped to be crimped or recessed at region of overlap with adjacent elongate members, to provide a more compact stent wall configuration. Such details of some of the embodiments disclosed herein can appear as shown in FIGS. 1-8.

As shown in FIG. 43D, it is also contemplated that a large fraction of the stent wall circumferential surface can comprise substantial openings between stent elements through which body lumen surface is exposed to the lumen center, e.g., where arterial epithelium may be exposed to blood flowing in the vessel. Likewise in branched lumens, such as arterial branching points, side lumens may communicate with the primary lumen through such openings.

Figure 44A:
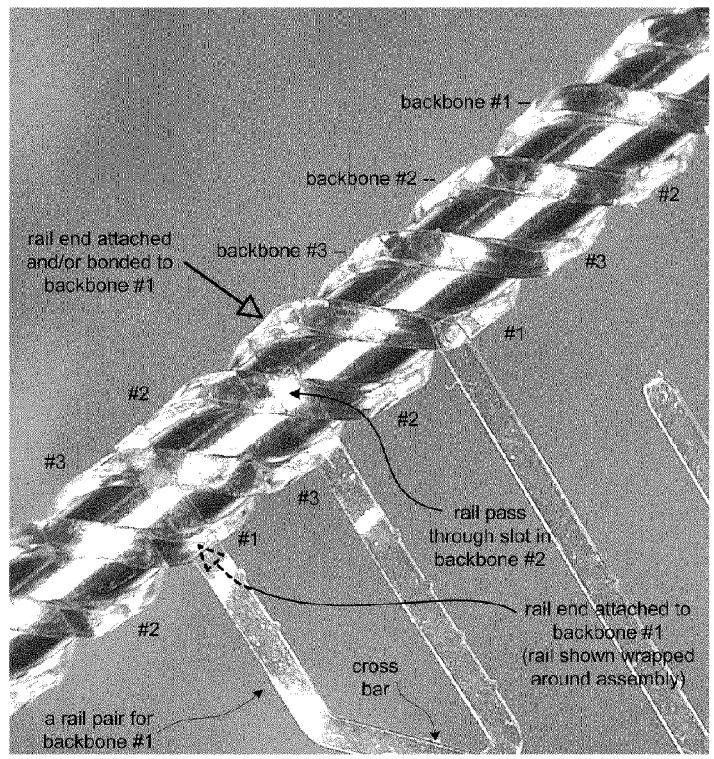
FIG. 44A is a photograph of a partially assembled stent assembly disposed on a support mandrel, according to an embodiment.
Figure 44B:
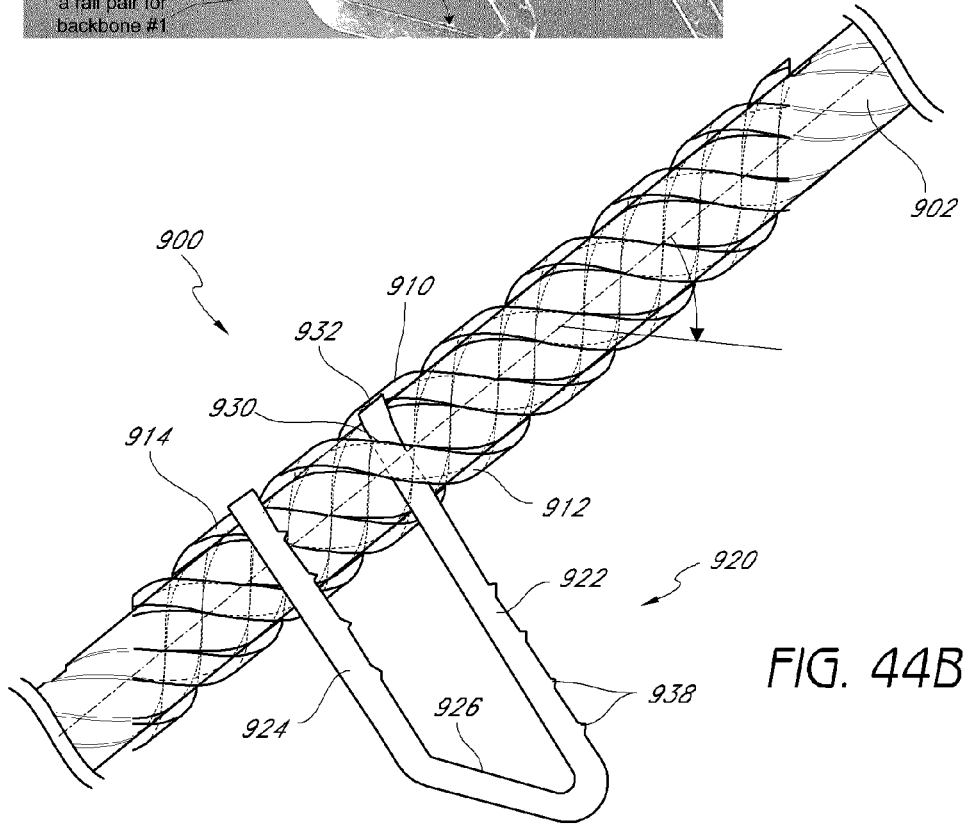
FIG. 44B is a line drawing of the stent assembly of FIG. 44A illustrating further elements of the stent assembly with the support mandrel in hidden lines, according to an embodiment.

FIG. 44A is a photograph showing an embodiment of a stent assembly 900 that is generally similar to the embodiment shown in FIGS. 38-43D. FIG. 44B is a line drawing showing subject matter of the photograph of FIG. 44A together with further illustration of the elements of the subject stent.

The embodiment of FIGS. 44A-B is shown in a partially-assembled configuration on a support mandrel 902. In this regard, the stent 900 is formed from stent elements comprising shaped strips of a flexible transparent polymeric sheet material. Shown in the figures is an assembly mandrel 902 supporting a relatively-compacted helical array of backbone members 910, 912, 914. The mandrel 902 may advantageously include helical grooves set at the helix angle α of the backbone array (or another alignment feature, such as a temporary adhesive) to temporarily align the backbone members 910, 912, 914. Conventional stereoscopic microscopes and manipulating tools may be used to facilitate manual assembly. Alternatively one or more assembly steps may be performed my automated equipment. Typically assembly may be done in a clean room environment.

A elongate member 920, in this example, comprising a parallel spaced-apart pair of rails 922, 924, is shown as it is inserted to engage the backbone array. Each proximal end of the rails 922, 924 of the elongate member 920 has been passed through a corresponding pass-through or engagement slot 930 in backbone member 912 and extends through to an adjacent receiving (fixation or connection) slot 932 in backbone member 910. The rails 922, 924 of the elongate member 920 are offset in length from one another so that both proximal rail ends contact the helical form of backbone 910 while the distal portion of the elongate member 920 extends generally perpendicularly to the helix axis. A second elongate member pair is shown in the right-hand portion of the photograph showing this offset.

In FIGS. 44A-B, the end of the right-hand rail 924 of the elongate member 920 is received in a connection slot 932 of the backbone 910 at the upper edge of the mandrel 902, while the end of the left-hand rail 922 is hidden from view as it wraps around the mandrel 902 to be received in another connection slot of the backbone 910 located near the bottom edge of the mandrel 902. In the illustrated embodiment, the means of fixation of the ends of the elongate member 920 to the backbone element 910 includes inserting the ends of the rails 922, 924 into a frictional or latching fit in a receiving slot to temporarily affix the ends of the rails 922, 924, followed by application of an adhesive fluid, such as a solvent or glue drawn into the slot by capillary action.

Note that as assembled on the mandrel 902, the rail "teeth" or other ratcheting elements 938 of each rail are outside the pass-through or engagement slot 930 of the backbone 912. Subsequently, additional elongate members may be mounted in other longitudinal locations along the stent 900 to pass through pass-through or engagement slots in the backbone 912 and affix to connection slots of the backbone 910, in the manner of a row of shingles. A plurality of elongate members may be similarly mounted so as to pass through pass-through or engagement slots in backbone 910 and affix to connection slots of the backbone 914. A plurality of elongate members may be similarly mounted so as to pass through pass-through or engagement slots in backbone 914 and affix to connection slots of the backbone 912, so as to complete a circumferential network of elongate members integrating the backbone array.

Figure 45A:
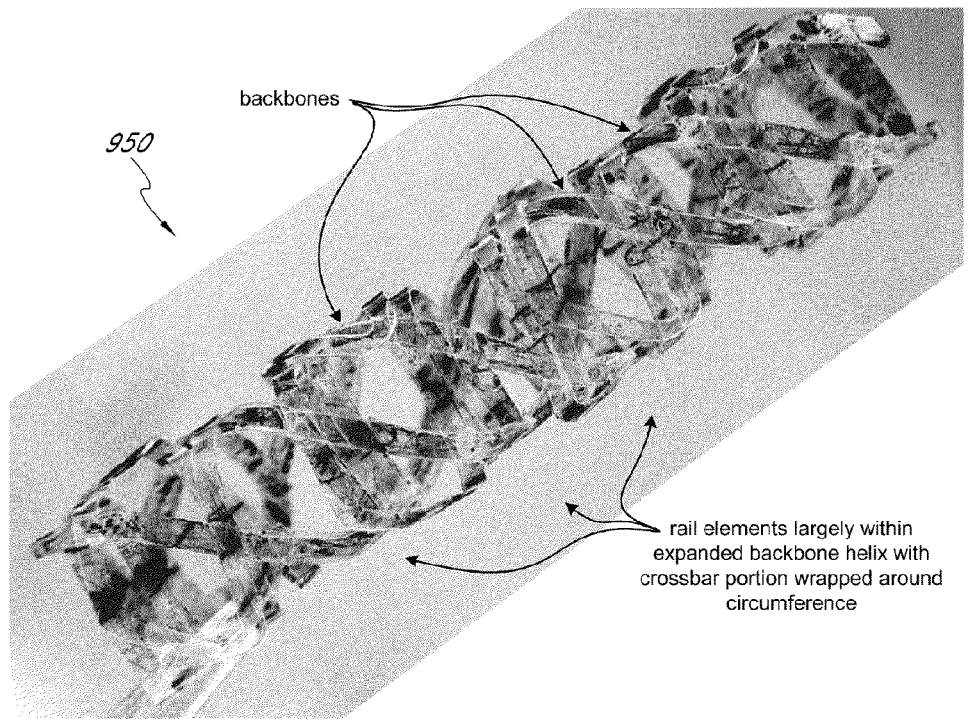
FIG. 45A is a photograph showing a completed stent assembly generally similar to that of FIG. 44A, wherein the stent assembly is in a partially compacted configuration, according to an embodiment.
Figure 45B:
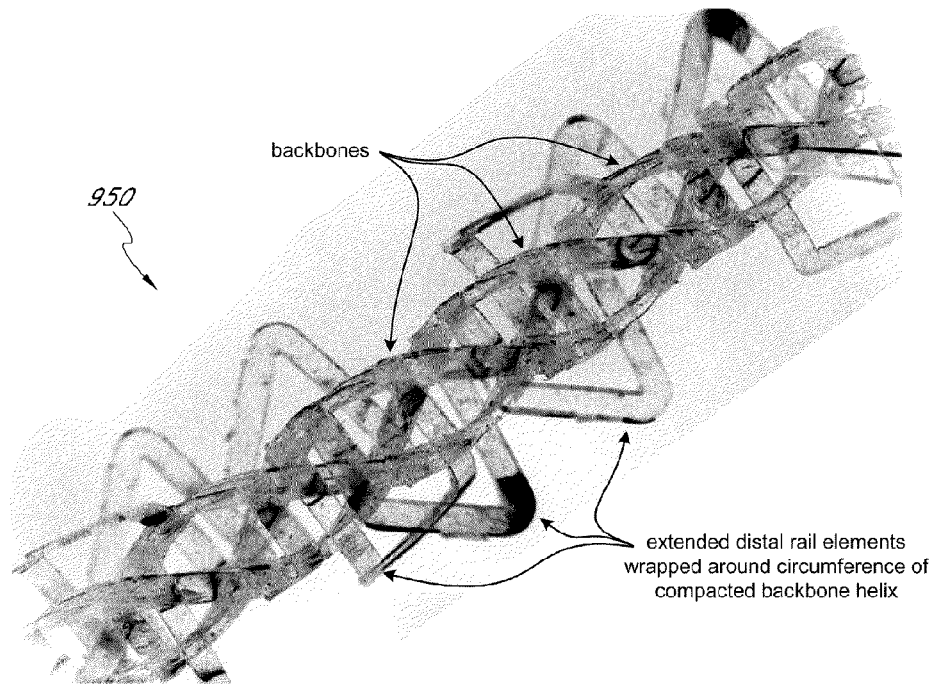
FIG. 45B is a photograph of the stent assembly of FIG. 45A wherein the stent assembly is in an expanded configuration, according to an embodiment.

FIGS. 45A and 45B, are photographs (processed as negatives for clarity) showing an assembled stent 950 generally similar to that shown partially assembled in FIG. 44A. In FIG. 45A, the stent 950 is shown with the backbone array in a relatively compacted configuration with the extending distal ends and crossbars of the elongate members partially wrapped around the stent outer circumference. In FIG. 45B, the stent 950 is shown with the backbone array in a partially expanded configuration with a larger portion of the distal ends of the elongate members "inside" or proximal to the pass-through or engagement slots, and the remainder of the distal rails and crossbars wrapped around the stent outer circumference.

Figures 47A, 47B:
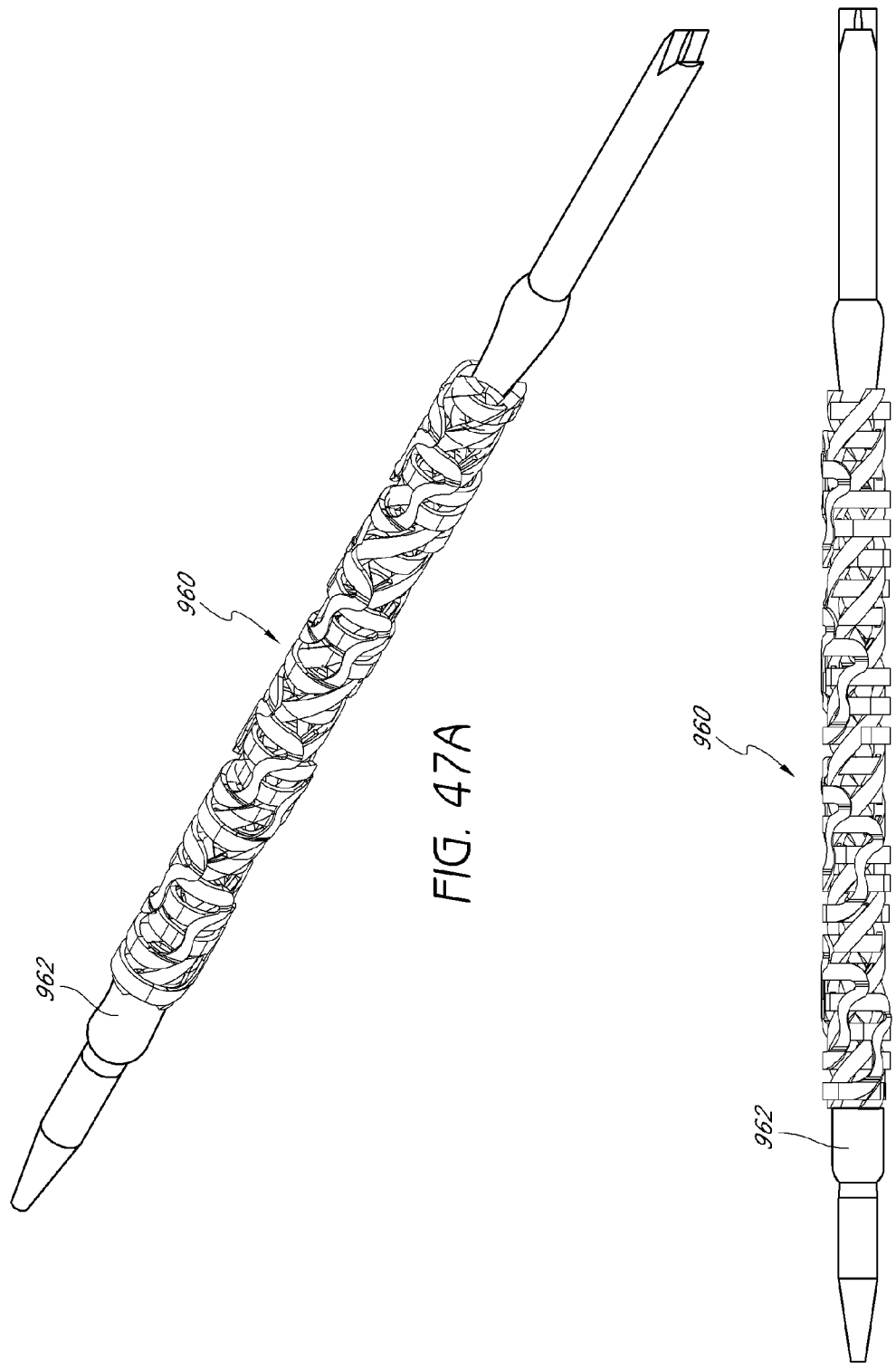
FIGS. 47A and 47B are perspective and side views, respectively, of a stent assembly generally similar to that shown in FIG. 43D, compacted on a balloon catheter for passage through a body lumen for deployment at a treatment target within the body lumen, according to an embodiment.

FIGS. 46 and 47A-B are perspective and side view drawings showing the manner of mounting the assembled stent 960 on a delivery device 962, such as a rapid-exchange balloon catheter assembly. FIG. 46 shows a stent 960 with the backbone array in a highly compacted configuration, with almost the full length of the rails of the elongate members extending distally from the backbone array. The elongate members may be wrapped around the circumference of the backbone array.

FIGS. 47A-B show an embodiment of a fully assembled stent 960 as compacted on a rapid-exchange balloon catheter assembly 962. Mild to moderate heating of the assembly 960 may be used to temporarily increase the flexibility of stent elements during compaction around the deflated balloon. An "iris-like" tool may also be used to assist in the compaction of the stent structure.

In some embodiments, the compacted stent 960 and balloon can be covered by a retractable flexible polymer sheath to secure the stent and assist passage and advancement of the catheter-stent assembly though a body lumen to an intended treatment target within the lumen.

Figure 48A:
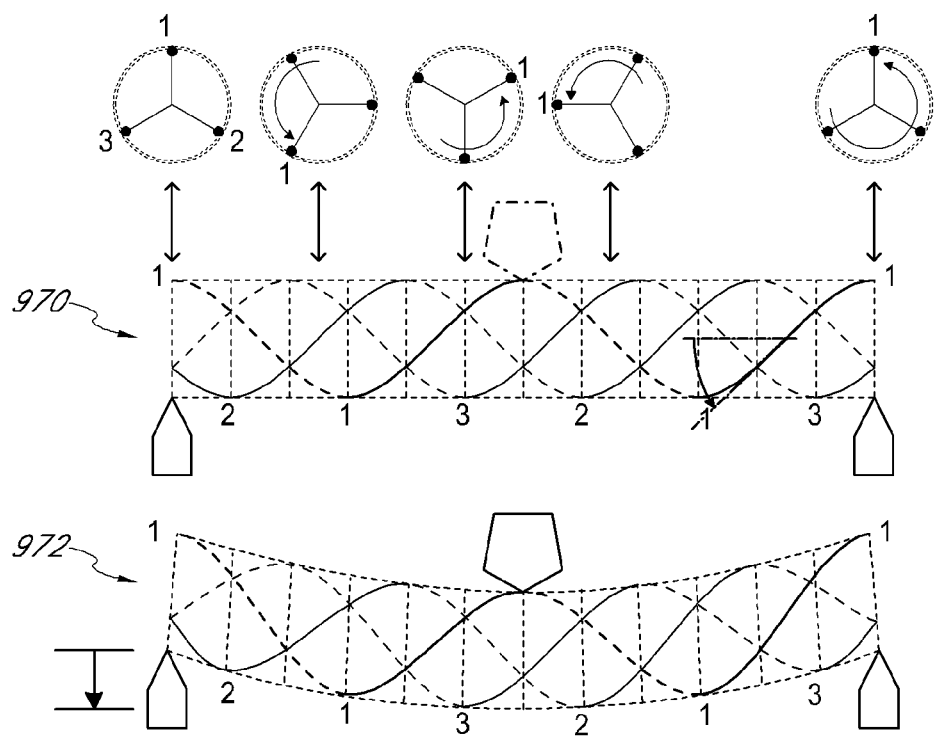
FIGS. 48A and 48B are simplified structural diagrams illustrating the role of a helical configuration of a stent assembly and the effect of reduction in longitudinal bending stiffness without sacrificing crush strength or overall structural integrity, according to some embodiments.
Figure 48B:
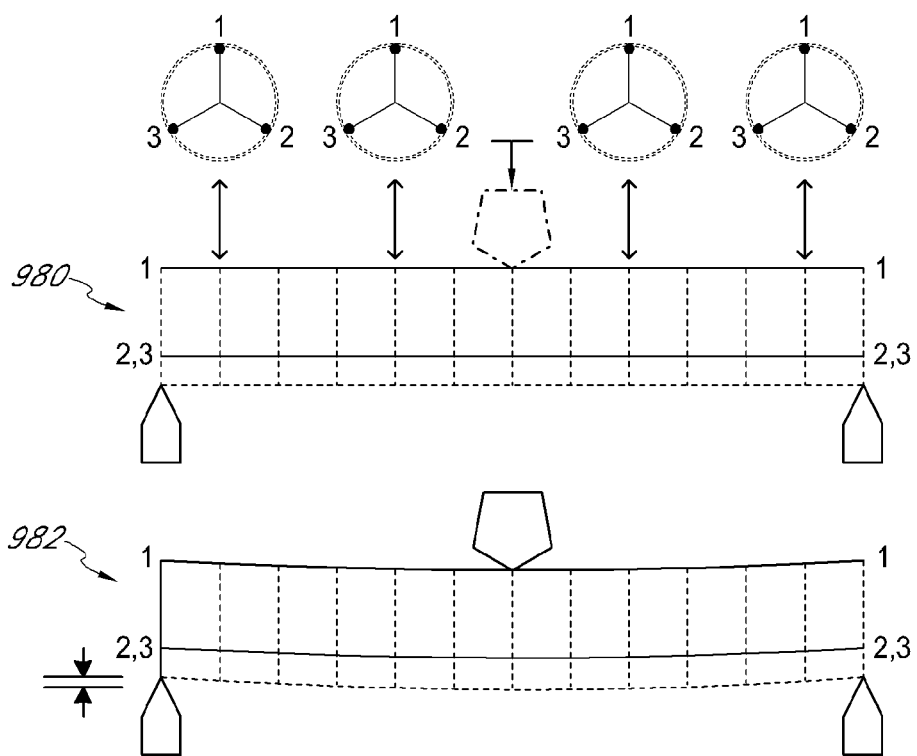

FIGS. 48A and 48B are two contrasting series of simplified structural diagrams illustrating the role of the helical configuration of stent assembly embodiments, and the effect of reduction in longitudinal bending stiffness without sacrificing crush strength or overall structural integrity. The central diagram of each series represents a lateral view of a stent assembly, generally structurally equivalent to that shown in FIGS. 43D and 45B, but having a broadly different range of backbone array helix angle.

In these diagrams, FIG. 48A illustrates a bending diagram of embodiments of the stents disclosed herein that utilize a helical backbone support. Further, FIG. 48B illustrates a bending diagram of a typical prior art stent having a non-helical backbone support. As explained herein, these diagrams illustrate the significant advantage that embodiments disclosed herein have over the prior art stents.

Beginning with FIG. 48A, the central view shows in side elevation the undeflected stent "beam" structure 970 arranged between end supports. The helical backbone member array is shown, and for each helical backbone member 1, 2, 3, the portion in front of the view is shown as a heavy solid line, the portion in the rear of the view is shown as a heavy dashed line. In this figure, the helix angle is large (about 45° as illustrated, although it can be substantially more or less than this). For clarity of presentation, backbone member #1 is shown in darker line color than companion backbones #2 and #3.

According to some embodiments, the elongate members and their rails and crossbars are represented collectively by a rectangular series of light dashed lines interconnecting the backbone members 1, 2, 3. In the top portion of FIG. 48A, there are arranged a longitudinal series of cross-sectional views of the stent assembly, each cross-section associated with a longitudinal point on the central view by a double arrow. In the cross-sections, the backbone members 1, 2, 3 are shown as simplified circular sections, and the elongate members represented collectively as circular dashed lines.

Note in the series of cross-sections of the top view, the position of backbone member #1, moving with the view from left to right, describes a counter-clockwise circular motion representing the helical change of circumferential position of the member.

The bottom portion or view of FIG. 48A shows in side elevation the deflected stent "beam" structure 972, as deflected by the application of a nominal lateral force midway between end supports. It may be readily understood that in such deflection, the strains induced in bending cause the upper portion of the stent assembly (as seen in the view) to be compressed, and the lower portion to be extended in tension. Since the longitudinal continuity is provided by the spring-like helical backbone members, there is relatively little resistance to such bending strain, and the deflection is relatively large (longitudinally flexible stent assembly).

It should be noted that notwithstanding the longitudinal flexibility of the overall stent assembly and the overall spring-like configuration of the backbone members, each backbone member is locally rigid and structurally continuous. Thus, the helical backbone members serve well to longitudinally integrate the circumferential radial strength of the hoop-like elongate members, so as to provide a smooth longitudinal bending behavior with minimal stress concentration. This provides a high resistance to kinking, hinging, and buckling. This forms a structure which is resistant to radial crush forces and denting, while still having a high degree of overall longitudinal flexibility. It can be understood that the helical backbone array likewise provides rotational (torsional) flexibility. These advantageous structural properties of the inventive stent assembly embodiments facilitate luminal insertion of the stent in the compacted state, flexible expansion and deployment of the stent in complexly curved lumen contours, and provide an expanded stent that is resistant to vasodynamic and dilative stresses and structural fatigue.

Furthermore, another advantage of some embodiments disclosed herein is that in contrast to prior art stents that may incorporate a helical design element, embodiments disclosed in the present application do not exhibit foreshortening when expanding from the collapsed diameter to the expanded diameter. In other words, the inventors of the present application have discovered that the various unique helical backbone structures disclosed herein can be used in combination with the slide-and-lock expansion mechanism disclosed herein in order to create a stent that has excellent flexibility, stiffness, and that also does not foreshorten, or decrease in axial or longitudinal length when expanded from the collapsed diameter to the expanded diameter. Foreshortening is a significant problem in other prior art stents, such as coil stents. Furthermore, the unique incorporation of the slide-and-lock expansion mechanism allows the helix angle of the helical backbone members to be maintained regardless of the diameter of the stent. Moreover, the inventors have also found that the unique alignment and orientation of the helical backbones, slots, and rail members in some embodiments provides a surprisingly efficient and effective expansion device exhibiting structural properties that are superior to prior art polymer stents and that rival structural properties of metal stents. As such, embodiments disclosed herein provide solutions to significant medical challenges and allow a patient to receive a stent that not only has structural properties that are optimized for the application, but that also is able to be resorbed into the body lumen upon completion of the goal.

Turning now to FIG. 48B, the series of upper central and lower views are substantially the same as in FIG. 48A, showing the same assembly elements, with the exception that that the helix angle of the backbone member array is small, e.g., approaching zero. In side view, the backbone members are represented as straight solid lines. The series of cross-sections of the top view show that the circumferential position of each backbone member remains constant with longitudinal position, indicating the lack of helical configuration.

The central portion or view of FIG. 48B shown a side elevational view of an undeflected stent "beam" structure 980. The bottom portion or view of FIG. 48B shows in side elevation the deflected stent "beam" structure 982, as deflected by the application of a nominal lateral force midway between end supports. The backbone member #1 indicated as the upper member and backbone members #2, #3 are indicated as lower members. It may be readily understood that in such deflection, each backbone member 1, 2, 3 resists strain with a directly axial application of compression or tension, resulting in a relatively stiff "beam" structure, causing the stent assembly to have relatively low overall longitudinal flexibility. It may also be seen that, since each backbone member 1, 2, 3 directly supports only a single circumferential position (does not "move" around the circumference), there are bending directions from which the structure is relatively more vulnerable to buckling, and the surface is relatively more vulnerable to denting than the embodiment of FIG. 48A. In this regard, various prior art stent suffer from such weaknesses and do not perform well in all bending directions.

In contrast, as discussed above, embodiments of the present application provide a uniquely-configured stent having a slide-and-lock helical backbone structure that provides essentially identical structural strength in any given bending direction. Once again, this unique feature of embodiments disclosed herein provides significant advantages over the prior art. Further, as shown in FIG. 49 and as discussed herein, embodiments of the stents disclosed herein avoid kinking, buckling, denting, and hinging due to the unique features and aspects of such embodiments.

Figure 49:
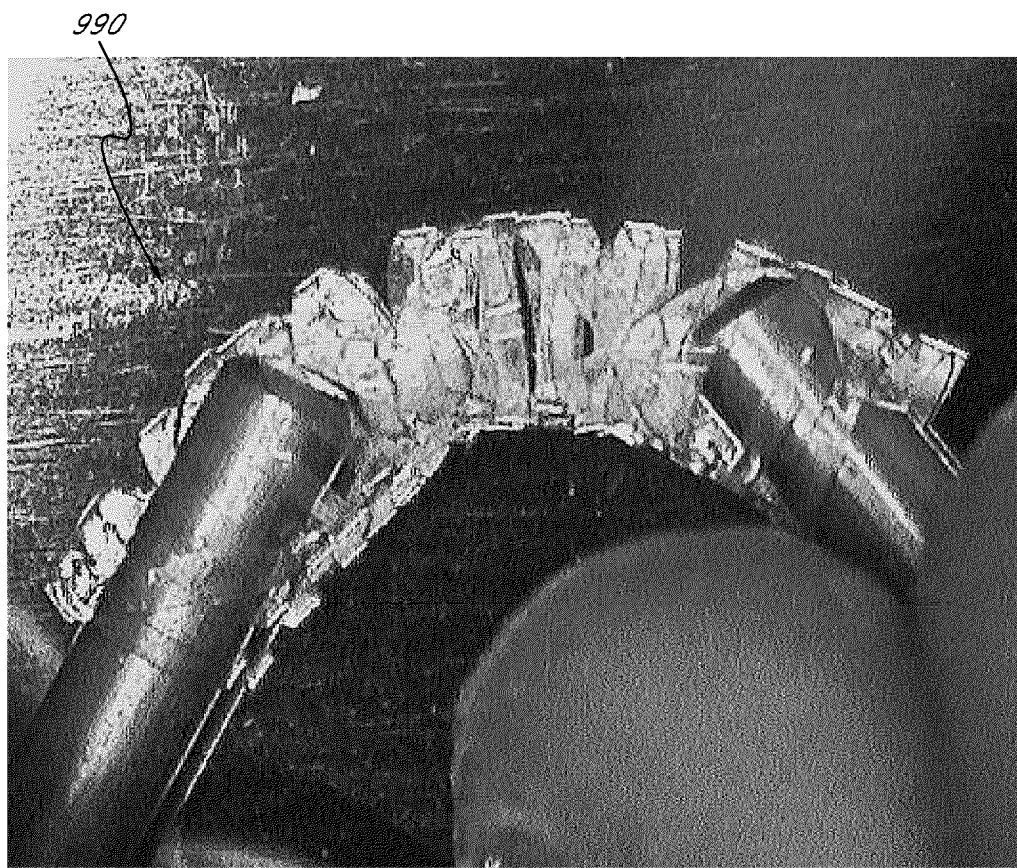
FIG. 49 is a photograph of a stent assembly illustrating the uniform longitudinal flexibility of the helical backbone assembly, according to an embodiment.

FIG. 49 is a photograph showing a stent assembly 990 generally similar to that shown in FIG. 45B, being bent manually through a smoothly-curved 90 degree bend without kinking or buckling. This demonstrates the structural principles described in detail above with respect to FIGS. 48A-B.

FIGS. 50-54 show planar representations of generally tubular circumferential surfaces of embodiments of stent assemblies. In each figure, a series of "backbone" members are arrayed in a generally parallel manner so as to extend longitudinally within the circumferential surface.

Figures 50, 51:
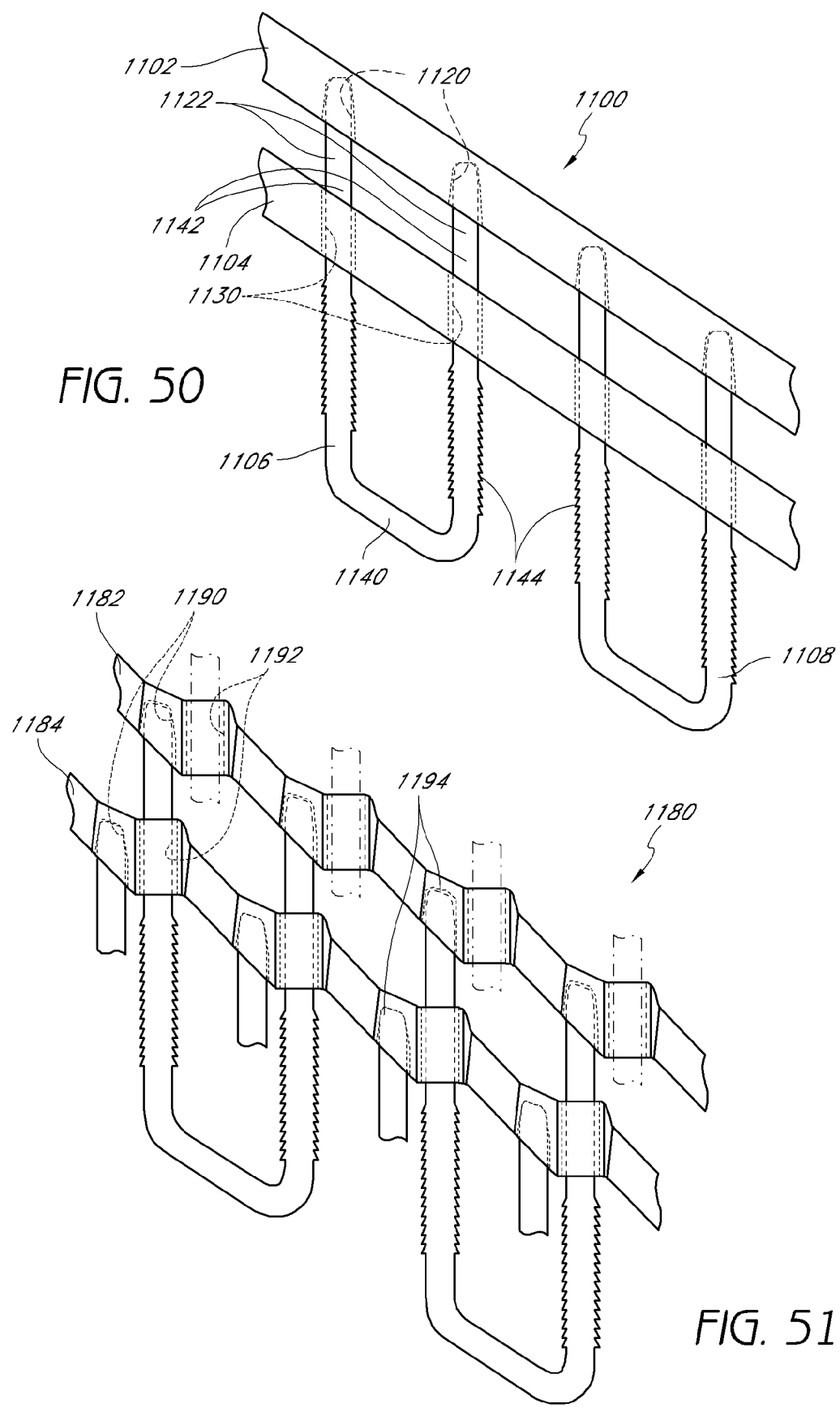
FIG. 50 is a top view of another exemplary stent assembly having constant backbone curvature, width, and angle, according to an embodiment.
FIG. 51 is a top view of another exemplary stent assembly having variable backbone curvature, width, and angle, according to another embodiment.

FIG. 50 generally illustrates a core-bonded stent assembly 1100 comprising first and second helical backbones 1102, 1104 and a plurality or pairs of elongate members 1106, 1108. The first helical backbone 1102 comprises at least one connection slot 1120 whereat proximal portions 1122 of the elongate members 1106 can be attached to the first helical backbone 1102. Further, the second helical backbone 1104 comprises a plurality of pass-through or engagement slots 1130 through which the elongate members 1106, 1108 can be passed. As shown, the pass-through or engagement slots 1130 extend at a non-perpendicular angle relative to the second helical backbone 1104.

Further, as discussed above with respect to other embodiments, the illustrated embodiment of FIG. 50 also shows that a pair of elongate members 1106 can be coupled together at the proximal portions thereof. For example, the proximal portions can be coupled by a crossbar 1140. Further, in some embodiments, the elongate members 1106 can comprise a narrowed or non-engaging portion 1142 adjacent to the proximal portions 1122 thereof. The narrow or non-engaging portions 1142 can be configured to be easily insertable into the pass-through or engagement slot 1130 of the second helical backbone 1104.

One of the many advantages of such an embodiment of a core-bonded stent is realized in the assembly of the stent. In particular, it is noted that during assembly, the distal ends 1122 of the elongate members 1106 are attached to the connection slots 1120 of the first helical backbone 1102 with the narrowed or non-engaging portions 1142 of the elongate members 1106, 1108 passing through the pass-through or engagement slots 1130 of the second helical backbone 1104. In this initial state of expansion, the stent assembly 1100 is in a compacted configuration. Accordingly, when the stent assembly 1100 expands for the first time, teeth 1144 of the elongate members 1106, 1108 will interact for the first time with the pass-through or engagement slots 1130 of the second helical backbone 1104. Because this is the first interaction between the teeth 1144 and the engagement slot 1130, the mechanical integrity will have been preserved and the slide-and-lock functionality of the stent 1100 will be maximized. Further, as discussed above, some embodiments can be configured to vary the length of the sliding rail portion and the ratcheting rail portion (see FIG. 39), such that inadvertent expansion of the stent can be avoided while manipulating the stent 1100.

These beneficial results of the disclosed embodiments of the core-bonded stents can be contrasted to situations in which the teeth of an elongate member are forced through an engagement slot during assembly in order to obtain an initial, collapsed configuration or where the engagement mechanism must otherwise be defeated to allow the elongate members and the helical backbone to assume an initial collapsed orientation.

Referring now to FIGS. 51-53B, other embodiments of core-bonded stent assemblies are shown. For example, the embodiment shown in FIG. 51 is generally similar to that of FIG. 50. However, FIG. 51 shows a stent assembly 1180 having a pair of helically-extending backbone members 1182, 1184 that each comprise respective connection slots 1190 and pass-through or engagement slots 1192. Further, the backbone members 1182, 1184 are configured to have a generally stair-stepped helical orientation and narrowed sections 1194 that can accommodate corresponding elongate members thereagainst for reducing the cross-sectional profile of the stent 1180.

FIGS. 52A-53B illustrate a modified version of the stent assembly of FIG. 51. In particular, FIGS. 52A-53B illustrate a stent assembly 1200 having offset portions and portions of variable thicknesses in order to reduce the cross-sectional profile and/or provide additional mating or engagement features between components of the stent assembly 1200. These features and advantages can be incorporated into various embodiments of the stents disclosed herein.

Figure 52A:
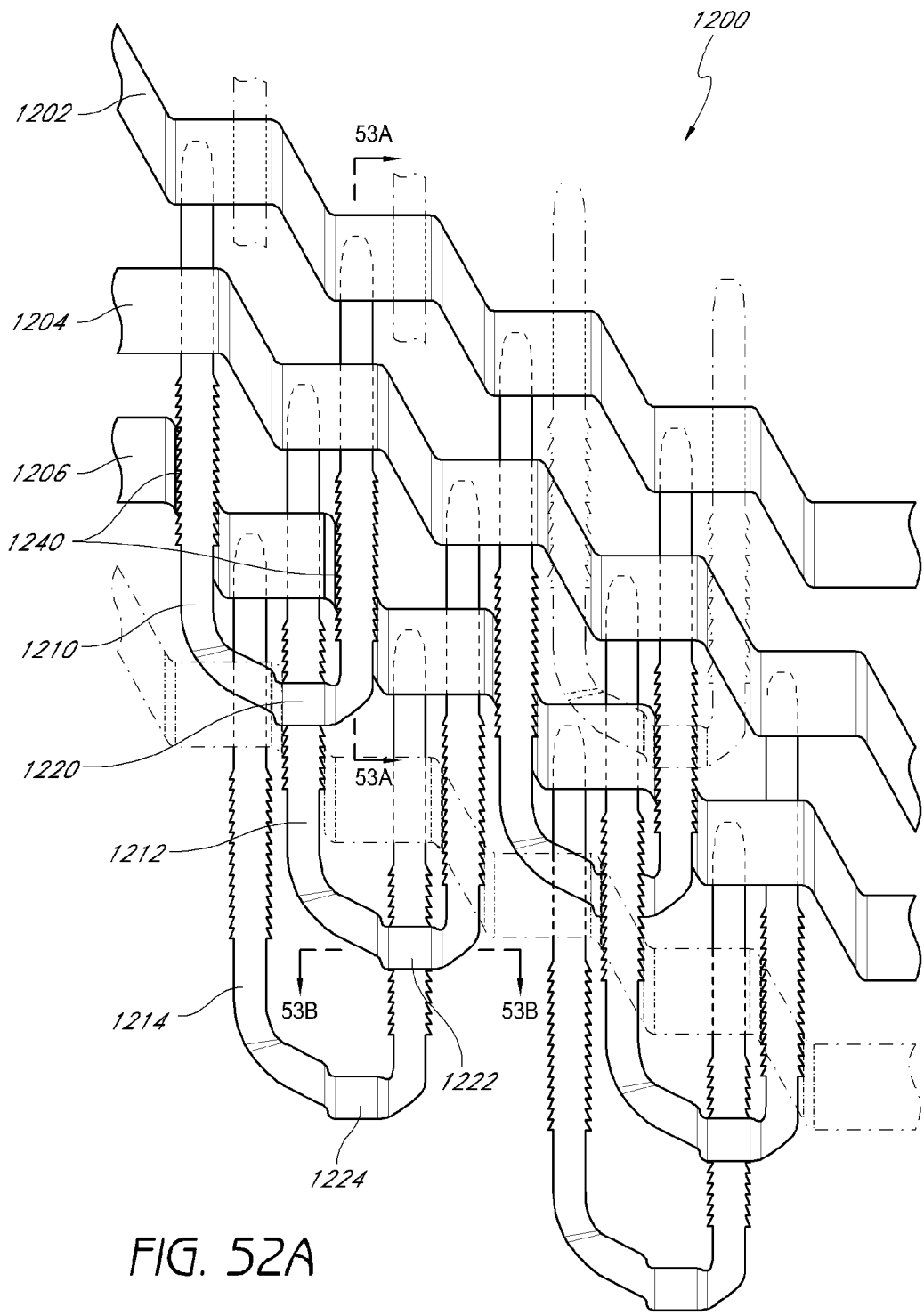
FIGS. 52A-B are top views of another exemplary stent assembly having variable backbone curvature, width, and angle and a crossbar portion, in collapsed and expanded states, according to an embodiment.

FIG. 52A illustrates a collapsed state or position of the stent assembly 1200. As illustrated, the assembly 1200 can comprise a plurality of helical backbone members 1202, 1204, 1206 and a plurality of elongate members 1210, 1212, 1214. In this embodiment, the elongate members 1210, 1212, 1214 can each comprise a pair of rails that are interconnected at their distal portions or ends by a crossbar 1220, 1222, 1224. As illustrated, the crossbar 1220, 1222, 1224 can have a raised section or recess that is configured to at least partially receive a portion of a elongate members 1210, 1212, 1214 disposed radially above or below the respective crossbar 1220, 1222, 1224.

Figure 52B:
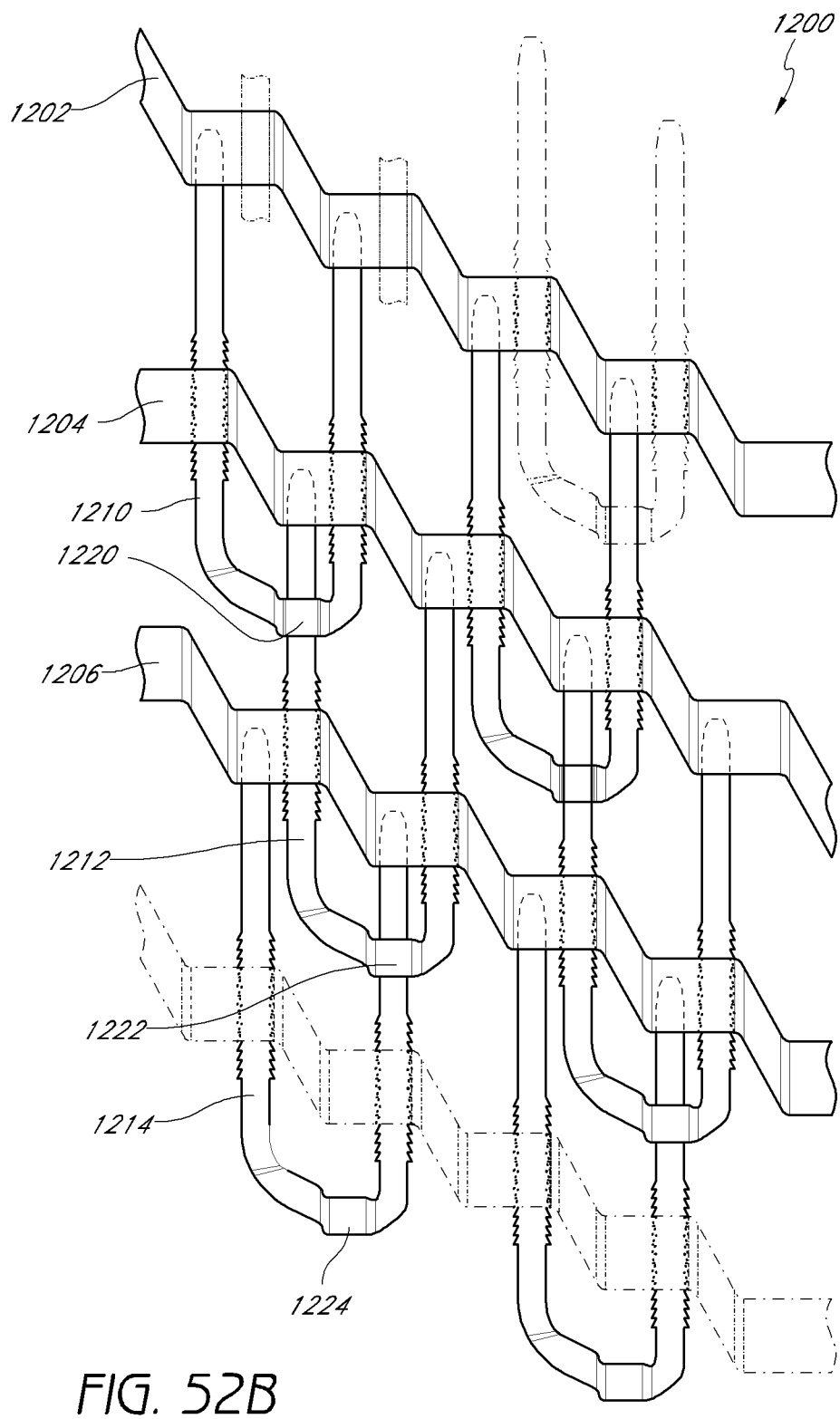

For example, the expanded view of the stent assembly 1200 shown in FIG. 52B illustrates that the crossbar 1220, 1222 have tracked the respective ones of the elongate members 1212, 1214 during expansion of the stent assembly 1200. Accordingly, one advantage of the raised section or recess of the crossbar 1220, 1222, 1224 is that the alignment of the elongate members 1210, 1212, 1214 relative to the backbone members 1202, 1204, 1206 can be generally unaffected. Further, the cross-sectional passing profile of the stent assembly 1200 can be at least partially reduced. Furthermore, the interaction between the crossbar 1220, 1222, 1224 with respective elongate members 1210, 1212, 1214 can also tend to cause the individual components or sets of interacting components of the stent assembly 1200 to function collectively or collaboratively in providing enhanced stiffness, crush strength, and resistance to kinking, buckling, denting, and hinging, etc.

Finally, the stent assembly 1200 also illustrates that the backbone members 1202, 1204, 1206 can be configured to include portions of reduced thickness or offsets in areas of overlap with the elongate members 1210, 1212, 1214. For example, as shown in FIG. 52A, the backbone 1206 can comprise one or more recessed portions 1240. The recessed portions 1240 can be configured to at least partially receive the elongate member 1210. Similarly, the other backbones 1202, 1204 and other embodiments disclosed herein can incorporate such recessed portions in order to advantageously configure the stent.

Figure 53A:
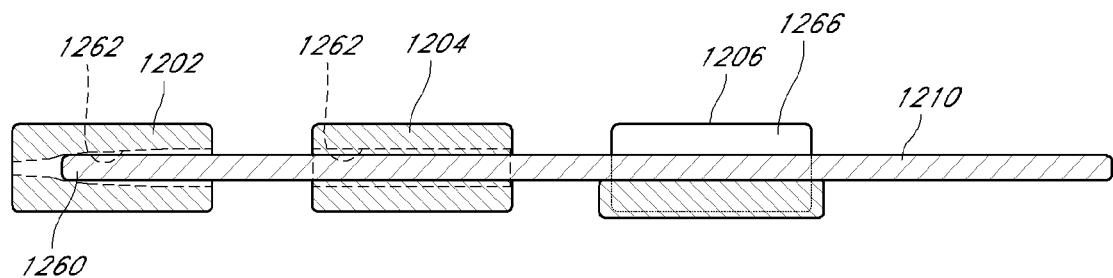
FIGS. 53A-B are cross-sectional side views of the stent embodiment shown in FIG. 52A, taken along the lines 53A-53A and 53B-53B, respectively of FIG. 52A, illustrating the arrangement of the backbones relative to an elongate member.
Figure 53B:
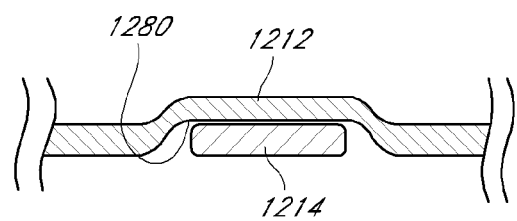

FIGS. 53A-B are side cross-sectional views illustrating the nesting of stent components in accordance with the embodiment shown in FIGS. 52A-B. As illustrated, a proximal portion or end 1260 of the elongate member or radial element 1210 can be interconnected with the backbone 1202 at a connection slot 1262 formed therein. The elongate member or radial element 1210 can pass through a pass-through or engagement slot 1264 of the backbone 1204. Further, the elongate member or radial element 1210 can also be positioned within a recessed portion 1266 of the backbone 1206.

The cross-sectional view of FIG. 53B is taken along the lines 53B-53B of FIG. 52A. As illustrated, FIG. 53B shows an embodiment of the crossbar 1222 of the elongate member 1212. In particular, this figure illustrates the nesting relationship of a recess 1280 of the crossbar 1222 of the elongate member 1212 with the rail of the elongate member 1214. Although FIG. 53B shows the recess 1280 of the crossbar 1222 as being sized to completely receive the elongate member 1214 therein, the recess 1280 can be configured to shallower or deeper. In addition, it is also contemplated that the recess 1280 can comprise one or more engagement structures that can engage with one or more corresponding engagement structures of the elongate member 1214. Accordingly, the interaction between the recess 1280 and the elongate member 1214 can facilitate spacing, expansion, or alignment of one or more components of the stent 1200.

Figure 54:
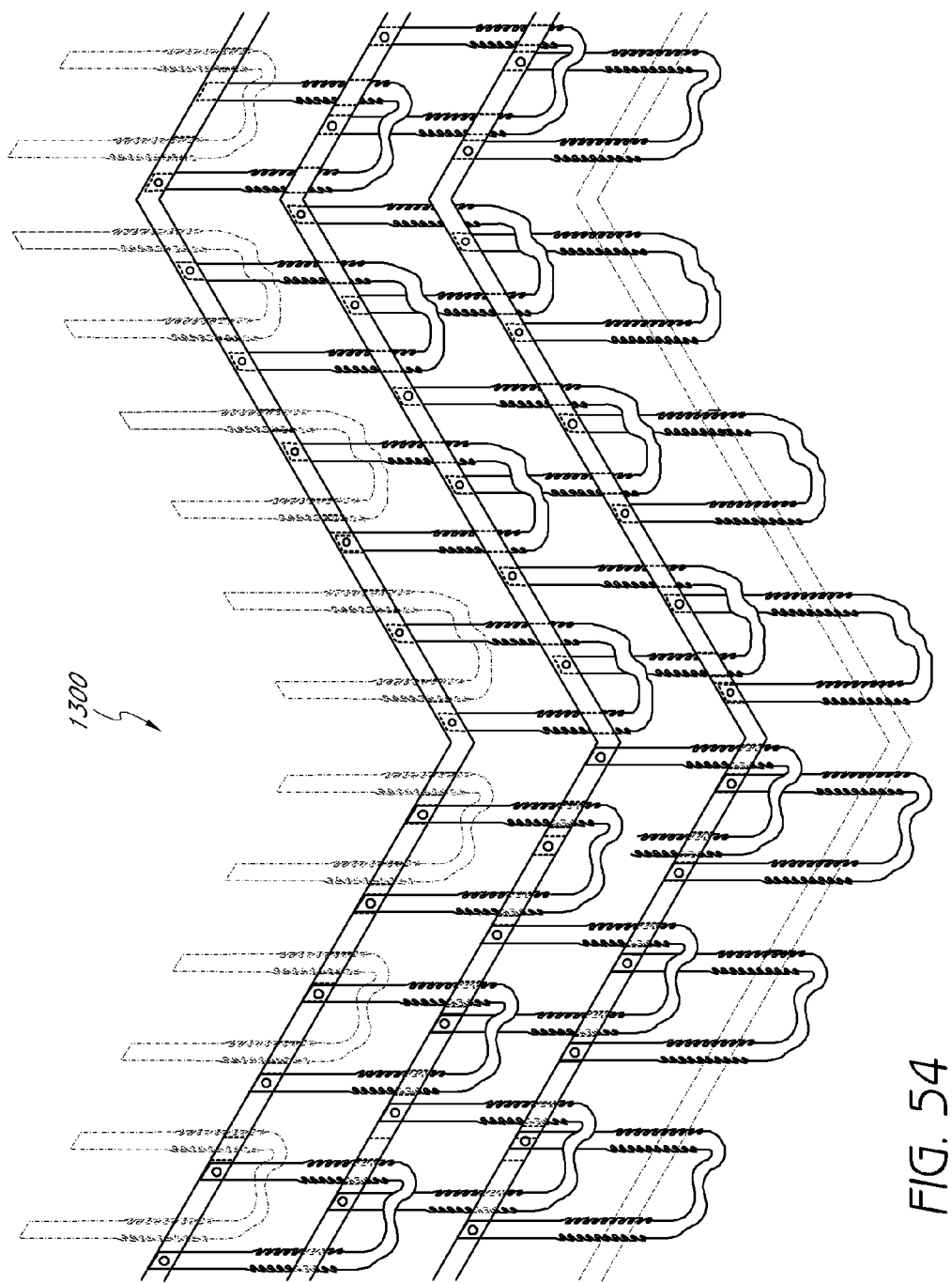
FIG. 54 is a top view of another exemplary stent assembly, according to yet another embodiment.

FIG. 54 illustrates yet another embodiment of a stent 1300 having a helical backbone structure that is in the shape of a chevron design. As will be appreciated with reference to the disclosure herein, FIG. 54 illustrates a core-bonded stent having many of the features and advantages discussed in reference to other embodiments herein.

Figure 55A:
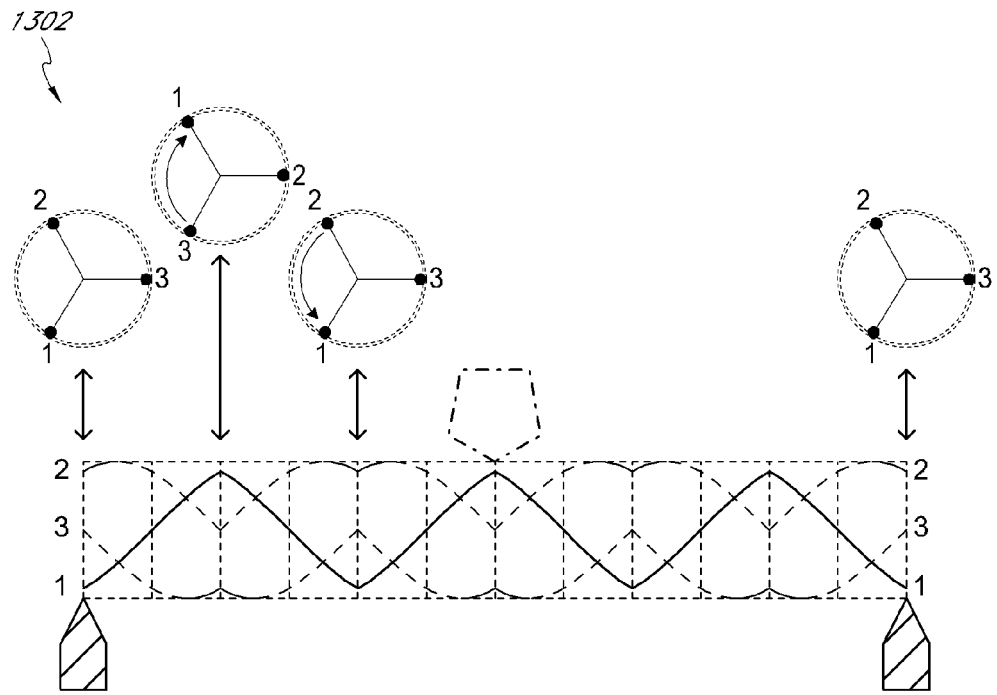
FIGS. 55A and 55B are simplified structural diagrams illustrating the role of a helical configuration of a stent assembly and the effect of reduction in longitudinal bending stiffness without sacrificing crush strength or overall structural integrity, according to some embodiments.
Figure 55B:
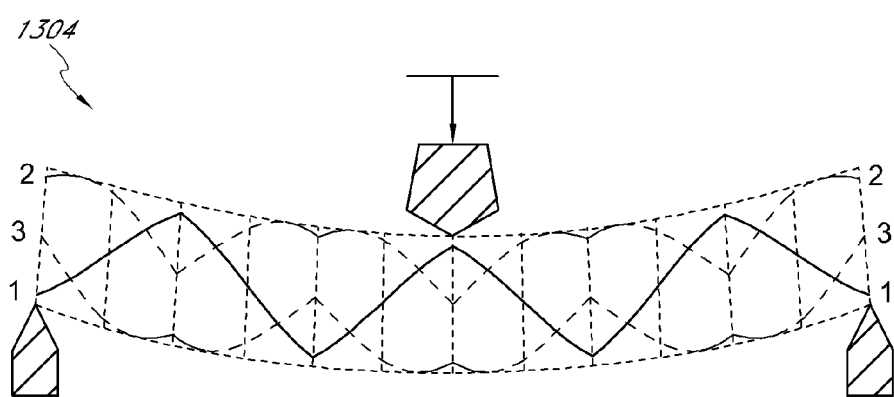

Further, FIGS. 55A-B are two contrasting series of simplified structural diagrams illustrating the role of the helical configuration of stent assembly embodiments having aspects of some embodiments, and the effect of reduction in longitudinal bending stiffness without sacrificing crush strength or overall structural integrity. FIG. 55A illustrates an undeflected stent "beam" structure 1302, and FIG. 55B illustrates a deflected stent "beam" structure 1304. The central diagram of each series represents a lateral view of a stent assembly, generally structurally equivalent to that shown in FIG. 54, but having a broadly different range of backbone array helix angle. As similarly noted above with respect to FIGS. 48A-B, the diagrams shown in FIGS. 55A-B indicate the flexibility of the stent 1300 along various points thereof.

Figure 58:
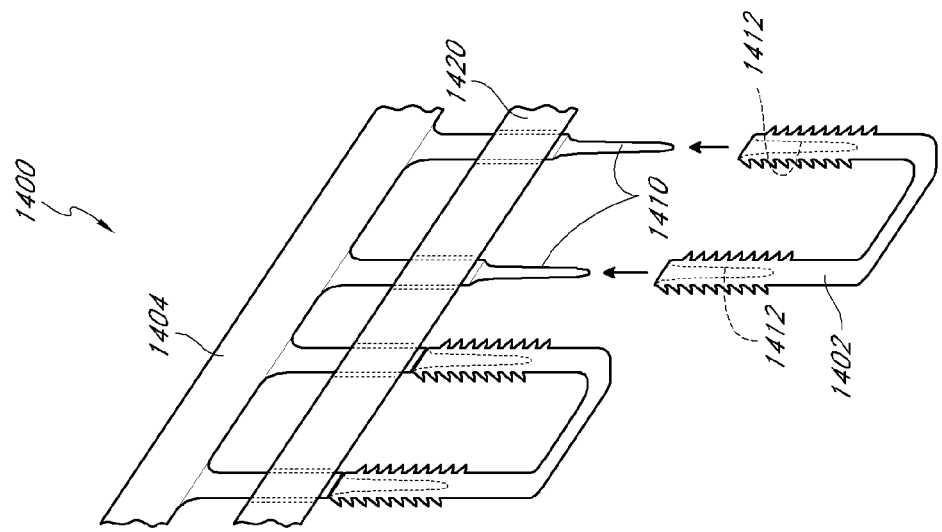
FIG. 58 is a top view of another mid-rail bonded embodiment of a stent.
Figure 57:
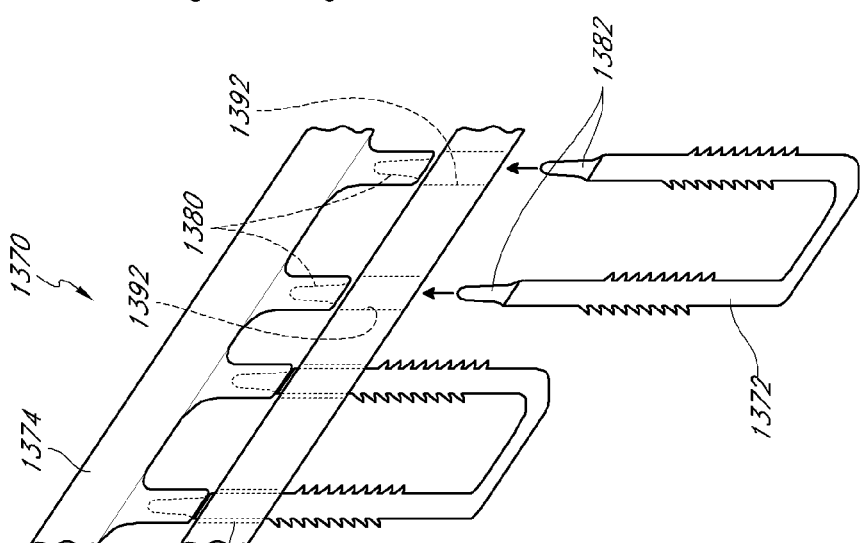
FIG. 57 is a top view of a mid-rail bonded embodiment of a stent.
Figure 56:
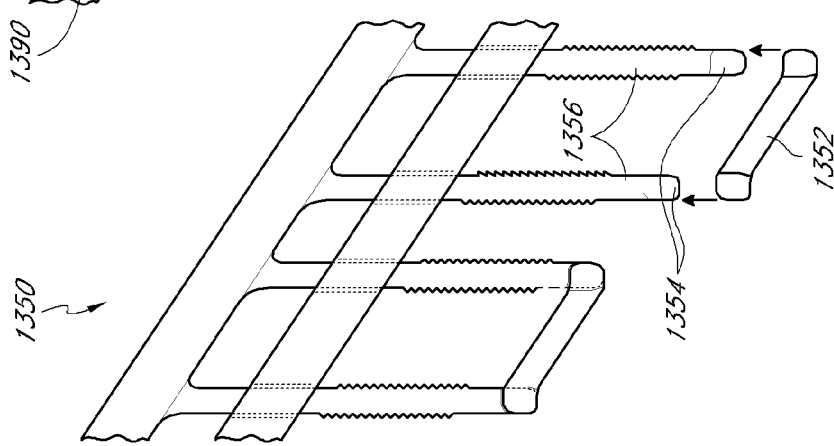
FIG. 56 is a top view of a tail-bonded embodiment of a stent.

Referring now to FIGS. 56-58, alternative methods and structures for tail and core bonding of a stent are shown. FIG. 56 represents a typical tail-bonded version of a stent 1350 in which a crossbar 1352 is attached to distal ends 1354 of a pair of elongate members 1356.

FIG. 57 illustrates an embodiment of a mid-rail bonded stent 1370 in which an elongate member 1372 is attached to a backbone element 1374 via one or more rail mounts 1380. The rail mounts can comprise one or more recesses or protrusions that can be interlocked with the elongate member, either by mechanical or adhesive bonding. In particular, the rail mounts can comprise one of a male and a female component that can mate with a corresponding male or female component on the elongate member. For example, in the illustrated embodiment, the rail mounts 1380 comprise a pair of female mounts having an interior receptacle in which a corresponding male component 1382 of the elongate member 1372 can be received. As noted above with respect to other connections of the elongate member with the backbone member, a variety of adhesives or other attachment structure and means can be used to secure the male component 1382 within the receptacle of the rail mount 1380.

In addition, it is noted that one of the advantages of mid-rail bonded stents can be realized in the assembly of the stent 1370. In particular, it is noted that a backbone member 1390 of an additional radial element is positioned such that pass-through or engagement slots 1392 of the backbone member 1390 receive the elongate member 1372 therethrough. As noted above, once the elongate member 1372 is attached and received within the slots 1380 in the collapsed state, the expansion of the stent to the expanded state will be the first time that the engagement mechanism is activated. As such, it is contemplated that the engagement between the teeth of the elongate member 1372 and the slots 1380 will be optimal.

FIG. 58 represents an embodiment that is similar to that shown in FIG. 57, except that the rail mounts are reversed. In this regard, FIG. 58 illustrates a stent assembly 1400 having an elongate member 1402 and a backbone member 1404. The elongate member 1402 can be attached to rail mounts 1410 of the backbone member 1404. In this embodiment, the rail mounts 1410 are configured generally as male components that are received within corresponding female receptacles 1412 formed at the proximal ends of the elongate member 1402. Other features of the embodiments disclosed herein, including the embodiment shown in FIG. 57, can be incorporated into the stent 1400 provided in FIG. 58 can provide many of the same advantages. However, among other things, it may be easier to interconnect a second backbone 1420 with the first backbone 1404 in the embodiment shown in FIG. 58.

Figure 59:
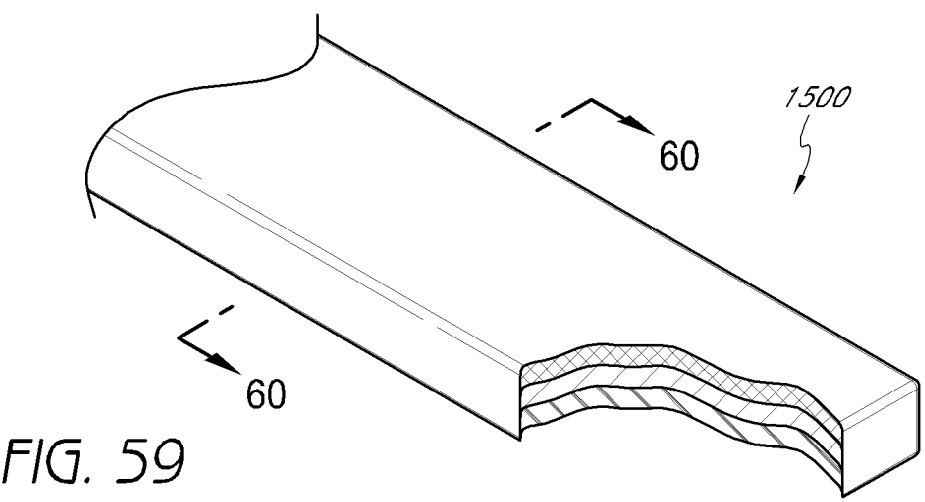
FIGS. 59-62 illustrate cross-sectional perspective and side views of composite materials that can be utilized in any of the embodiments disclosed herein.
Figure 60:
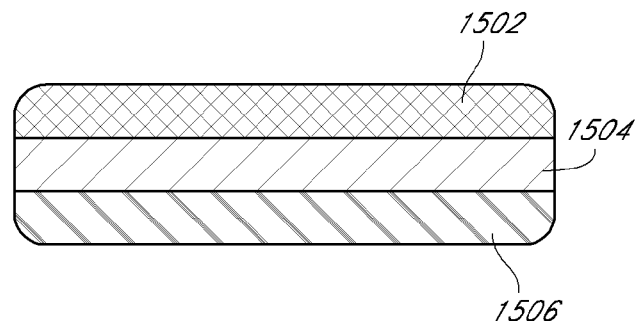
Figure 61:
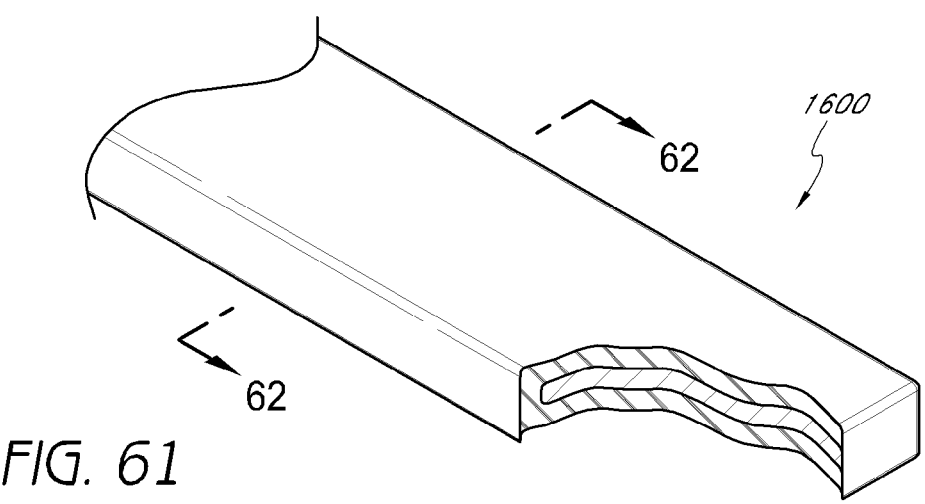
Figure 62:
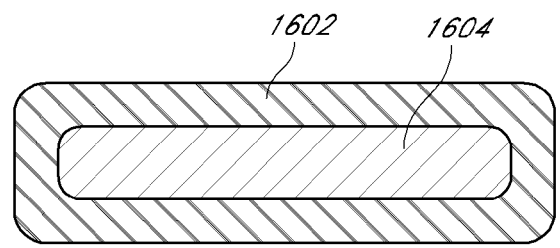

FIGS. 59-62 illustrate a variety of cross-sectional perspective and side views of a composite component that can be utilized in any of the embodiments disclosed herein. For example, FIGS. 59-60 illustrate a component 1500 that can have one or more layers 1502, 1504, 1506. The layers 1502, 1504, 1506 can comprise different materials that are selected to optimize a structural or chemical attribute of the component. Further, FIGS. 61-62 illustrate another component 1600 that comprises an encapsulating material 1602 and a core material 1604. The encapsulating material and the core material 1602, 1604 can comprise different materials that are selected to optimize a structural or chemical attribute of the component 1600. A plethora of other designs and modifications will be apparent to one of skill. The modification of one or more structural or chemical attributes of a component of the stent is possible by varying the composition of the materials, as noted herein.

For example, the structural properties of a given polymer, metal, or composite can be targeted in a given combination. The chemical (including medicinal) properties of a given polymer, metal, or composite can be targeted in another combination. Further, the degradation rate of a metal, polymer, or composite can be targeted in yet another combination. Accordingly, in some embodiments, it is contemplated that polymer, metal, and/or composite materials can be used in combinations that provide stents having one or more types of a polymer, metal, and/or composite. In particular, it is contemplated that composite polymer stents can be provided that have structural properties that mimic structural properties of metal stents.

Testing Data of Stent Embodiments Compared to Prior Art Stents

As discussed herein, embodiments of the helical slide-and-lock stents can provide superior flexibility and stiffness compared to prior polymer stents. In this regard, various tests have shown that the stiffness of embodiments disclosed herein is greater than that of prior art polymer stents. Indeed, the structural properties, such as the stiffness, of embodiments disclosed herein more closely mimics the structural properties of metal stents.

Accordingly, embodiments of the stents disclosed herein represent a significant advance in stent technology which allows a polymer and/or composite material to be used in a configuration that provides structural properties that can approach and/or replicate the structural properties of a metal stent. Metal stents have the disadvantage of not being as bioresorbable as polymer stents; however, metal stents have long provided superior structural properties that may be needed for severe lesions, such as rigidity, stiffness, and crush strength. In contrast, prior polymer stents could provide resorbability and other benefits not available with metal stents; however, prior polymer stent were not as stiff, rigid, or strong as the metal counterparts. One of the solutions and advances made by embodiments of the stent of the present application is the provision of a manner of achieving bioresorbability and the other benefits of polymers while exhibiting superior structural properties similar to metal stents. Indeed, the unique features and configurations of the helical slide-and-lock polymer stents disclosed herein enable one of skill to obtain the benefits of polymer and metal stents. Further, the present disclosure also provides for a variety of stents having a composite material structure which can incorporate advantages of various materials.

Lamination Manufacturing Process Embodiments

Stents in accordance with embodiments can be fabricated or created using a wide variety of manufacturing methods, techniques and procedures. These include, but are not limited to, laser processing, milling, stamping, forming, casting, molding, bonding, welding, adhesively fixing, and the like, among others.

In some embodiments, stent features and mechanisms can be created in a generally two dimensional geometry and further processed, for example by utilizing, but not limited to, bonding, lamination and the like, into three dimensional designs and features. In other embodiments, stent features and mechanisms can be directly created into three dimensional shapes, for example by utilizing, but not limited to, processes such as injection molding and the like.

In certain embodiments, stents can be fabricated by using an injection molding process, technique or method. For example, an injection molding process or the like, among others, can be used to form stent rows as integral units. The axially extending rows can then be connected and rolled into a tubular form in the collapsed state.

In some embodiments, a lamination stack can used to fabricate the stent rows by a lamination process in accordance with one embodiment. The axially extending rows can then be connected and rolled into a tubular form in the collapsed state.

The lamination stack, in some embodiments, generally can comprise three sheets or pallets which can have the desired features formed thereon, for example, by laser cutting, etching and the like. The pallets can be aligned and joined, for example, by bonding, welding and the like to form a unit. The excess material (e.g., side and end rails) can be removed to form the stent rows. The pallets can include various circumferentially nesting features such as male and female articulating and/or ratcheting designs to control and limit the diameter in collapsed and fully deployed states.

Metal Stents and Methods of Manufacturing

Possible materials for making the stents in accordance with some embodiments include cobalt chrome, 316 stainless steel, tantalum, titanium, tungsten, gold, platinum, iridium, rhodium and alloys thereof or pyrolytic carbon. In still other alternative embodiments, the stents can be formed of a corrodible material, for instance, a magnesium alloy. Although various stent embodiments have been described as being conventional balloon expandable stents, those skilled in the art will appreciate that stent constructions according to embodiments can also be formed from a variety of other materials to make a stent crush-recoverable. For example, in alternative embodiments, such as self expandable stents, shape memory alloys that allow for such, such as Nitinol and Elastinite®, can be used in accordance with embodiments.

Various methods of forming the individual elements from metal sheets can comprise laser cutting, laser ablation, die-cutting, chemical etching, plasma etching and stamping and water jet cutting of either tube or flat sheet material or other methods known in the art which are capable of producing high-resolution components. The method of manufacture, in some embodiments, depends on the material used to form the stent. Chemical etching provides high-resolution components at relatively low price, particularly in comparison to high cost of competitive product laser cutting. Some methods allow for different front and back etch artwork, which could result in chamfered edges, which can be desirable to help improve engagements of lockouts. Further one can use plasma etching or other methods known in the art which are capable of producing high-resolution and polished components. The embodiments disclosed herein are not limited to the means by which stent or stent elements can be fabricated.

Once the base geometry is achieved, the elements can be assembled numerous ways. Tack-welding, adhesives, mechanical attachment (snap-together and/or weave together), and other art-recognized methods of attachment, can be used to fasten the individual elements. Some methods allow for different front and back etch artwork, which could result in chamfered edges, which can be desirable to help improve engagements of lockouts. In an advantageous method of manufacture, the components of the stent can be heat set at various desired curvatures. For example, the stent can be set to have a diameter equal to that of the deflated balloon, as deployed, at a maximum diameter, or greater than the maximum diameter. In yet another example, elements can be electropolished and then assembled, or electropolished, coated, and then assembled, or assembled and then electropolished.

Polymeric Stents

While metal stents possess certain desirable characteristics, the useful lifespan of a stent is estimated to be in the range of about 6 to 9 months, the time at which in-stent restenosis stabilizes and healing plateaus. In contrast to a metal stent, a bioresorbable stent cannot outlive its usefulness within the vessel. Moreover, a bioresorbable stent could potentially be used to deliver a greater dose of a therapeutic agent, deliver multiple therapeutic agents at the same time or at various times of its life cycle, to treat specific aspects or events of vascular disease. Additionally, a bioresorbable stent can also allow for repeat treatment of the same approximate region of the blood vessel. Accordingly, there remains an important unmet need to develop temporary (i.e., bioresorbable and/or radiopaque) stents, wherein the polymeric materials used to fabricate these stents can have the desirable qualities of metal (e.g., sufficient radial strength and radiopacity, etc.), while circumventing or alleviating the many disadvantages or limitations associated with the use of permanent metal stents.

In some embodiments, the stent can be formed from biocompatible polymers that are bio-resorbable (e.g., bio-erodible or bio-degradable). Bio-resorbable materials can be preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof. For additional information, see U.S. Pat. Nos. 4,980,449, 5,140,094, and 5,264,537, the disclosures of each of which are incorporated by reference herein.

In one mode, the degradable materials can be selected from the group consisting of poly(glycolide-trimethylene carbonate), poly(alkylene oxalates), polyaspartimic acid, polyglutarunic acid polymer, poly-p-dioxanone, poly-.beta.-dioxanone, asymmetrically 3,6-substituted poly-1,4-dioxane-2,5-diones, polyalkyl-2-cyanoacrylates, polydepsipeptides (glycine-DL-lactide copolymer), polydihydropyranes, polyalkyl-2-cyanoacrylates, poly-.beta.-maleic acid (PMLA), polyalkanotes and poly-.beta.-alkanoic acids. There are many other degradable materials known in the art. (See e.g., Biomaterials Science: An Introduction to Materials in Medicine (29 Jul., 2004) Ratner, Hoffman, Schoen, and Lemons; and Atala, A., Mooney, D. Synthetic Biodegradable Polymer Scaffolds. 1997 Birkhauser, Boston; each of which are incorporated herein by reference).

Further still, in another embodiment, the stents can be formed of a polycarbonate material, such as, for example, tyrosine-derived polycarbonates, tyrosine-derived polyarylates, tyrosine-derived diphenol monomers, iodinated and/or brominated tyrosine-derived polycarbonates, iodinated and/or brominated tyrosine-derived polyarylates. For additional information, see U.S. Pat. Nos. 5,099,060, 5,198,507, 5,587,507, which was resiussed in U.S. Pat. Nos. RE37,160, 5,670,602, which was resiussed in U.S. Pat. Nos. RE37,795, 5,658,995, 6,048,521, 6,120,491, 6,319,492, 6,475,477, 5,317,077, and 5,216,115, and U.S. application Ser. No. 09/350,423, the disclosures of each of which are incorporated by reference herein. In yet another embodiment, the polymer can be any of the biocompatible, bioabsorbable, radiopaque polymers disclosed in: U.S. Patent Application Nos. 60/852,513, 60/852,471, 60/601,526, 60/586,796, 60/866,281, 60/885,600, Ser. Nos. 10/952,202, 11/176,638, 11/335,771, 11/200,656, 11/024,355, 10/691,749, 11/418,943, and 11/873,362; U.S. Patent Publication No. US26115449A1; U.S. Pat. Nos. 6,852,308 and 7,056,493; and PCT Application Nos. PCT/US2005/024289, PCT/US2005/028228, PCT/US07/01011, and PCT/US07/81571, the disclosures of each of which are incorporated herein by reference thereto.

Natural polymers (biopolymers) include any protein or peptide. Biopolymers can be selected from the group consisting of alginate, cellulose and ester, chitosan, collagen, dextran, elastin, fibrin, gelatin, hyaluronic acid, hydroxyapatite, spider silk, cotton, other polypeptides and proteins, and any combinations thereof.

In yet another alternative embodiment, shape-shifting polymers can be used to fabricate stents constructed according to embodiments. Suitable shape-shifting polymers can be selected from the group consisting of polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. For addition disclosure on bio-degradable shape-shifting polymers, see U.S. Pat. Nos. 6,160,084 and 6,284,862, the disclosures of each of which are incorporated by reference herein. For additional disclosure on shape memory polymers, see U.S. Pat. Nos. 6,388,043 and 6,720,402, the disclosures of each of which are incorporated by reference herein. Further the transition temperature can be set such that the stent can be in a collapsed condition at a normal body temperature. However, with the application of heat during stent placement and delivery, such as via a hot balloon catheter or a hot liquid (e.g., saline) perfusion system, the stent can expand to assume its final diameter in the body lumen. When a thermal memory material is used, it can provide a crush-recoverable structure.

Further still, stents can be formed from biocompatible polymers that are biostable (e.g., non-degrading and non-erodible). Examples of suitable non-degrading materials include, but are not limited to, polyurethane, Delrin, high density polyethylene, polypropylene, and poly(dimethyl siloxane).

In some embodiments, the layers can comprise or contain any example of thermoplastics, such as the following, among others: fluorinated ethylene-propylene, poly(2-hydroxyethyl methacrylate) (aka pHEMA), poly(ethylene terephthalate) fiber (aka Dacron®) or film (Mylar®), poly(methyl methacrylate) (aka PMMA), Poly(tetrafluoroethylene) (aka PTFE and ePTFE and Gore-Tex®), poly(vinyl chloride), polyacrylates and polyacrylonitrile (PAN), polyamides (aka Nylon), polycarbonates and polycarbonate urethanes, polyethylene and poly(ethylene-co-vinyl acetate), polypropylene, polystyrene, polysulphone, polyurethane and polyetherurethane elastomers such as Pellethane® and Estane®, Silicone rubbers, Siloxane, polydimethylsiloxane (aka PDMS), Silastic®, Siliconized Polyurethane.

Finally, the polymer(s) utilized in embodiments of the stent can be fabricated according to any variety of processes, such as those discussed in U.S. Patent Application Nos. 60/852,471 and 60/852,513, and U.S. Pat. Nos. 5,194,570, 5,242,997, 6,359,102, 6,620,356, and 6,916,868, the disclosures of each of which are incorporated by reference herein.

Methods of Manufacturing and Assembling Polymeric Stents

Where plastic and/or degradable materials are used, the elements can be made using laser ablation with a screen, stencil or mask; solvent casting; forming by stamping, embossing, compression molding, centripetal spin casting and molding; extrusion and cutting, three-dimensional rapid prototyping using solid free-form fabrication technology, stereolithography, selective laser sintering, or the like; etching techniques comprising plasma etching; textile manufacturing methods comprising felting, knitting, or weaving; molding techniques comprising fused deposition modeling, injection molding, room temperature vulcanized molding, or silicone rubber molding; casting techniques comprising casting with solvents, direct shell production casting, investment casting, pressure die casting, resin injection, resin processing electroforming, or injection molding or reaction injection molding. Certain embodiments with the disclosed polymers can be shaped into stents via combinations of two or more thereof, and the like.

Such processes can further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. For additional information, see U.S. patent application Ser. No. 10/655,338, the disclosure of which is incorporated by reference herein.

Stents of some of the embodiments can be manufactured with elements prepared in full stent lengths or in partial lengths of which two or more are then connected or attached. If using partial lengths, two or more can be connected or attached to comprise a full length stent. In this arrangement the parts can be assembled to give rise to a central opening. The assembled full or partial length parts and/or modules can be assembled by inter-weaving them in various states, from a collapsed state, to a partially expanded state, to an expanded state.

Further, elements can be connected or attached by solvent or thermal bonding, or by mechanical attachment. If bonding, advantageous methods of bonding comprise the use of ultrasonic radiofrequency or other thermal methods, and by solvents or adhesives or ultraviolet curing processes or photoreactive processes. The elements can be rolled by thermal forming, cold forming, solvent weakening forming and evaporation, or by preforming parts before linking.

Rolling of the flat series of module(s) to form a tubular member can be accomplished by any means known in the art, including rolling between two plates, which can be each padded on the side in contact with the stent elements. One plate can be held immobile and the other can move laterally with respect to the other. Thus, the stent elements sandwiched between the plates can be rolled about a mandrel by the movement of the plates relative to one another. Alternatively, 3-way spindle methods known in the art can also be used to roll the tubular member. Other rolling methods that can be used in accordance with certain embodiments include those used for "jelly-roll" designs, as disclosed for example, in U.S. Pat. Nos. 5,421,955, 5,441,515, 5,618,299, 5,443,500, 5,649,977, 5,643,314 and 5,735,872, the disclosures of each of which are incorporated herein in their entireties by reference thereto.

The construction of the slide-and-lock stents in these fashions can provide a great deal of benefit over the prior art. The construction of the locking mechanism can be largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In some embodiments, the frequency of catches, stops or teeth present on selected circumferential elements can prevent unnecessary recoil of the stent subsequent to expansion.

Radiopacity

Traditional methods for adding radiopacity to a medical product include the use of metal bands, inserts and/or markers, electrochemical deposition (i.e., electroplating), or coatings. The addition of radiopacifiers (i.e., radiopaque materials) to facilitate tracking and positioning of the stent could be accommodated by adding such an element in any fabrication method, by absorbing into or spraying onto the surface of part or all of the device. The degree of radiopacity contrast can be altered by element content.

For plastics and coatings, radiopacity can be imparted by use of monomers or polymers comprising iodine or other radiopaque elements, i.e., inherently radiopaque materials. Common radiopaque materials include barium sulfate, bismuth subcarbonate, and zirconium dioxide. Other radiopaque elements include: cadmium, tungsten, gold, tantalum, bismuth, platinum, iridium, and rhodium. In some embodiments, a halogen such as iodine and/or bromine can be employed for its radiopacity and antimicrobial properties.

Multi-Material Vascular Prosthesis

In still other alternative embodiments, various materials (e.g., metals, polymers, ceramics, and therapeutic agents) can be used to fabricate stent embodiments. The embodiments can comprise: 1) differentially layered materials (through stacking in the vertical or radial axis) to create a stack of materials (materials can be stacked in any configuration, e.g., parallel, staggered, etc.); 2) spatially localized materials which can vary along the long axis and/or thickness of the stent body; 3) materials that are mixed or fused to create a composite stent body (e.g., whereby a therapeutic agent(s) is within the stent body with a polymer); 4) embodiments whereby a material can be laminated (or coated) on the surface of the stent body (see Stent Surface Coatings with Functional Properties as well as see Therapeutic Agents Delivered by Stents); and, 5) stents comprised of 2 or more parts where at least one part can be materially distinct from a second part, or any combination thereof.

The fashioning of a slide-and-lock multi-material stent can have between two or more materials. Thickness of each material can vary relative to other materials. This approach as needed or desired allows an overall structural member to be built with each material having one or more functions contributing towards enabling prosthesis function which can include, but is not limited to: 1) enabling mechanical properties for stent performance as defined by ultimate tensile strength, yield strength, Young's modulus, elongation at yield, elongation at break, and Poisson's ratio; 2) enabling the thickness of the substrate, geometrical shape (e.g., bifurcated, variable surface coverage); 3) enabling chemical properties of the material that bear relevance to the materials performance and physical state such as rate of degradation and resorption (which can impact therapeutic delivery), glass transition temperature, melting temperature, molecular weight; 4) enabling radiopacity or other forms of visibility and detection; 5) enabling radiation emission; 6) enabling delivery of a therapeutic agent (see Therapeutic Agents Delivered by Stents); and 7) enabling stent retention and/or other functional properties (see Stent Surface Coatings with Functional Properties).

In some embodiments, the materials can comprise load-bearing properties, elastomeric properties, mechanical strength that can be specific to a direction or orientation e.g., parallel to another material and/or to the long axis of the stent, or perpendicular or uniform strength to another material and/or stent. The materials can comprise stiffeners, such as the following, boron or carbon fibers, pyrolytic carbon. Further, stents can be comprised of at least one re-enforcement such a fibers, nanoparticles or the like.

In another implementation of some embodiments, the stent can be made, at least in part, from a polymeric material, which can be degradable. The motivation for using a degradable stent can be that the mechanical support of a stent can only be necessary for several weeks. In some embodiments, bioresorbable materials with varying rates of resorption can be employed. For additional information, see U.S. patent application Ser. Nos. 10/952,202 and 60/601,526, the disclosures of each of which are incorporated by reference herein. Degradable polymeric stent materials can be particularly useful if it also controls restenosis and thrombosis by delivering pharmacologic agents. Degradable materials can be well suited for therapeutic delivery (see Therapeutic Agents Delivered by Stents).

In some embodiments, the materials can comprise or contain any class of degradable polymer as previously defined. Along with variation in the time of degradation and/or resorption the degradable polymer can have other qualities that are desirable. For example, in some embodiments the materials can comprise or contain any example of natural polymers (biopolymers) and/or those that degrade by hydrolytic and/or enzymatic action. In some embodiments, the material can comprise or contain any example of hydrogels that can or cannot be thermally reversible hydrogels, or any example of a light or energy curable material, or magnetically stimulateable (responding) material. Each of these responses can provide for a specific functionality.

In some embodiments, the materials can comprise or be made from or with constituents which can have some radiopaque material alternatively, a clinically visible material which can be visible by x-ray, fluoroscopy, ultrasound, MRI, or Imatron Electron Beam Tomography (EBT).

In some embodiments, one or more of the materials can emit predetermined or prescribed levels of therapeutic radiation. In an embodiment, the material can be charged with beta radiation. In another embodiment, the material can be charged with Gamma radiation. In yet another embodiment, the material can be charged with a combination of both Beta and Gamma radiation. Stent radioisotopes that can be used include, but are not limited to, 103Pd and 32P (phosphorus-32) and two neutron-activated examples, 65Cu and 87Rb2O, (90)Sr, tungsten-188 (188).

In some embodiments, one or more of the materials can comprise or contain a therapeutic agent. The therapeutic agents can have unique, delivery kinetics, mode of action, dose, half-life, purpose, et cetera. In some embodiments, one or more of the materials comprise an agent which provides a mode and site of action for therapy for example by a mode of action in the extracellular space, cell membrane, cytoplasm, nucleus and/or other intracellular organelle. Additionally an agent that serves as a chemoattractant for specific cell types to influence tissue formation and cellular responses for example host-biomaterial interactions, including anti-cancer effects. In some embodiments, one or more of the materials deliver cells in any form or state of development or origin. These could for example be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells can serve as a limited release system. For additional concepts of therapeutic delivery, see the section entitled: Therapeutic Agents Delivered by Stents.

Therapeutic Agents Delivered by Stents

In another implementation, the stent further can comprise an amount of a therapeutic agent (as previously defined for a pharmaceutical agent and/or a biologic agent) sufficient to exert a selected therapeutic effect. The material of at least a portion of the stent itself can comprise at least one therapeutic agent, or at least one therapeutic agent can be added to the stent in a subsequent forming process or step. In some embodiments of the stent (e.g., polymer stents and multi-material stents), the therapeutic agent can be contained within the stent as the agent is blended with the polymer or admixed by other means known to those skilled in the art.

For example, one or more therapeutic agents can be delivered through a multi-material vascular prosthesis. In some embodiments, the entire stent can be formed from materials comprising one or more therapeutic agents. In other embodiments, portions of the stent, such as individual components thereof, can comprise materials comprising one or more therapeutic agents. In such embodiments, it is contemplated that the therapeutic agent(s) can be released as the stent material degrades.

For example, the therapeutic agent can be embedded or impregnated into the film by means of a combination of solvent casting and thermal pressing. In such a method, the film can be formed from a mixture of the polymer and the therapeutic agent (20% solids polymer, for example poly (90% DTE-co-10% DT carbonate), which can be made with 1% rapamycin in dichloromethane). Once this mixture is prepared, the film can be cast using a doctor blade. Alternatively, the film can be formed by using a mechanical reverse roll coater or other solvent-based film caster. Once the film is cast, the solvent can be evaporated off using a vacuum oven, e.g., for a period of time and at a temperature suitable for the polymer and drug, such as at 40° C. for at least 20 hours. Once the film is dried, it can be thermally pressed, e.g., at a temperature of 100° C. between two heated platens of a hydraulic press. This allows the potency of the drug to be retained.

In addition, the therapeutic agent can be embedded or impregnated into the film using only a solvent or by spin casting. Once a therapeutic agent is selected, one needs to determine if the solvent is compatible with the agent and the polymer chosen. The objective is to prepare a suitable sprayable suspension. Additionally, the stability of the drug can be measured such that the therapeutic agent can remain active while in the coating as well under physiological conditions once released from the film. This can be determined by those skilled in the art who conduct standard in vitro elution studies (see Dhanikula et al., *Development and Characterization of Biodegradable Chitosan Films for Local Delivery of Paclitaxel*, The AAPS Journal, 6 (3) Article 27 (2004), http://www.aapsj.org/view.asp?art=aapsj060327; and Kothwala et al., *Paclitaxel Drug Delivery from Cardiovascular Stent*, Trends in Biomaterials Artificial Organs, Vol. 19(2), 88-92 (2006), http://medind.nic.in/taa/t06/i1/taat06i1p88.pdf) of agent embedded films and through the use of analytical methods such as HPLC methods (see Dhanikula et al., *Development and Characterization of Biodegradable Chitosan Films for Local Delivery of Paclitaxel*; and Kothwala et al., *Paclitaxel Drug Delivery from Cardiovascular Stent*) to detect the purity of the drug.

In other embodiments, at least one therapeutic agent can be added to the stent and/or its components after the formation of the stent and/or its components. For example, at least one therapeutic agent can be added to individual stent components, through a coating process or otherwise. The addition of at least one therapeutic agent can occur before or after cutting or lasing of the stent components. In another example, at least one therapeutic agent can also be added to at least a portion of the stent after partial or full assembly thereof, through a coating process or otherwise. In some embodiments of the stent, the therapeutic agent can be delivered from a polymer coating on the stent surface. In other embodiments of the stent, a therapeutic agent can be localized in or around a specific structural aspect of the device.

For example, the therapeutic agent can be delivered from a polymer coating on the stent surface. Thus, the stent can be made by applying the therapeutic agent to a stent component before the stent is assembled or formed. In this regard, the stent component can be created from a polymer sheet, such as a flat polymer film. Thus, at least one stent component can be separated from a remainder or excess portion of the film either before or after the therapeutic agent has been applied to the stent component and/or film. After the therapeutic agent is applied and the stent component is separated from the film, the stent component can be assembled (and in some embodiments, with other stent components) to form a stent therefrom.

In an exemplary embodiment, the stent can be prepared with the following preparation method. The stent can be initially prepared by creating a pattern of a stent component on a flat polymer film. The creation of the pattern on the film can occur before or after application of a therapeutic agent thereto, as discussed below. The pattern of the stent component can be created on the film such that the stent component can be detached from the film when desired. In some embodiments, the pattern can be created using a laser to lase the pattern onto the film. Additionally, the lased pattern can be of any given stent component design, such as that used in a slide and lock stent design. After the pattern is created on the film, the entire film can be cleaned. For example, if the therapeutic agent has not yet been applied to the film, the entire lased film can be immersed into a cleaning solution that is compatible with the specific type of polymer from which the film is made. The cleaned film can then be dried, for example, by being blown and oven dried.

A coating formulation can be prepared by dissolving or dispersing the polymer and the therapeutic agent(s) of choice and solvent(s) or other compatible excipient(s) using a calculated amount of each component to achieve the desired concentration. The coating formulation can then be applied to the lased polymer film using one or more coating methods. For example, the film may be coated by means of spraying, dipping, or other coating methods. Additionally, cross-linking reagents may also be used to prepare a coating.

In a spraying coating method, the lased polymer films can be coated with the coating formulation by first mounting the cleaned dried films into a spray apparatus. The coating formulation can then be sprayed onto the film, and the film can be rotated 180 degrees such that the other side can be coated if desired. This method can allow for coating of one or both sides of the stent component(s). This method can also allow one to apply different therapeutic agents per side of the lased film and/or stent component and to selectively coat regions thereof. The method can further allow one to coat multiple drugs per film and/or stent component. Alternative coating methods can allow for other similar benefits.

For example, a therapeutic agent can be coated onto a film or stent component as in the following illustration. First, the therapeutic agent in this example is a Polymer-Paclitaxel Formulation, such as a 0.5% [25% Paclitaxel/75% Poly (86.75% I2DTE-co-10% I2DT-co-3.25% PEG2000 carbonate)] in tetrahydrofuran (THF), which can be prepared using an analytical balance. In order to do so, one must first weigh 0.0150 g of Paclitaxel into a tared vial. Then weigh 0.0450 g of polymer into another vial. Next, weigh 11.940 g of THF into each vial. Shake the vials on a laboratory shaker, such as a Roto-genie, for at least one hour. In this example, coating can be achieved using a spray gun apparatus, such as an air brush (see Westedt, U., *Biodegradable Paclitaxel-loaded Nanoparticles and Stent Coatings as Local Delivery Systems for the Prevention of Restenosis—Dissertation*, Marburg/Lahn (2004), http://deposit.ddb.de/cgi-bin/dokserv?idn=972868100&dokvar=d1&dokext=pdf&filename=972868100.pdf; and Berger, H. L. *Using Ultrasonic Spray Nozzles to Coat Drug-Eluting Stents*, Medical Device Technology (2006), http://www.devicelink.com/mdt/archive/06/11/004.html). Typically, the spray gun apparatus should first be cleaned with THF. In order to do so, a syringe can be filled with at least 10 ml of THF. The syringe can then be attached to a spray line attached to the spray gun. Gradually, the 10 ml of THF can be pushed from the syringe into the spray gun without N2 pressure. This can be repeated as necessary to ensure that the line is washed clean. The syringe pump can then be set up with the syringe containing the Polymer-Paclitaxel Formulation.

Next, a film, which can be either lased or unlased, can be placed into a hooded environment and mounted or clipped into a holder. If necessary, the surfaces of the film can be cleaned of lint and dust using a pure air or gas source or equivalent. For consistent coating quality, the film can be programmed to move at a set rate (distance and speed) relative to a spray stream by integrating the film holder apparatus with a motion control system. Manual coating without the motion control can also be used to achieve a coating. The spray gun can also be set to direct the spray to only a given location to control coating distribution.

In some embodiments, to coat both sides of the film uniformly, the spray cycle can start with the spray hitting at the bottom corner of the film, and the motion control should move the film incrementally as it traverses back and forth in front of the spray nozzle. The system can then move the film back to the start position so the spray is directed at the bottom. The film holder can be turned 180 degrees and the cycle can be repeated to coat the second side. After coating, the film holder can be removed with the film and the film can be dried in a vacuum oven at a temperature suitable for the drug and polymer, e.g., 25°±5° C. for at least 20 hours.

Other methods and teachings related to impregnation or coating processes are found in the following references, the entirety of each of which is hereby incorporated by reference herein: Westedt, U., *Biodegradable Paclitaxel-loaded Nanoparticles and Stent Coatings as Local Delivery Systems for the Prevention of Restenosis—Dissertation*, Marburg/Lahn (2004), http://deposit.ddb.de/cgi-bin/dokserv?idn=972868100&dokvar=d1&dokext=pdf&filename=972868100.pdf; Berger, H. L. *Using Ultrasonic Spray Nozzles to Coat Drug-Eluting Stents*, Medical Device Technology (2006), http://www.devicelink.com/mdt/archive/06/11/004.html; Dhanikula et al., *Development and Characterization of Biodegradable Chitosan Films for Local Delivery of Paclitaxel*, The AAPS Journal, 6 (3) Article 27 (2004), http://www.aapsj.org/view.asp?art=aapsj060327; and Kothwala et al., *Paclitaxel Drug Delivery from Cardiovascular Stent*, Trends in Biomaterials & Artificial Organs, Vol. 19(2), 88-92 (2006), http://medind.nic.in/taa/t06/i1/taat06i1p88.pdf.

After the film is coated using a given coating method, the film can be given time to dry. Once dried, the lased, coated stent component(s) can be separated from the remainder of the film. Care should be taken to not disturb the surfaces of the coated stent component(s) when being detached from the film and assembled or knitted together to form a three-dimensional cylindrical stent.

In another variation the therapeutic agent can be delivered by means of a non-polymer coating. In other embodiments of the stent, the therapeutic agent can be delivered from at least one region or one surface of the stent. The therapeutic agent can be chemically bonded to the polymer or carrier used for delivery of the therapeutic from at least one portion of the stent and/or the therapeutic can be chemically bonded to the polymer that can comprise at least one portion of the stent body. In some embodiments, a polymer can be used as a component of the coating formulation. Accordingly, the coating can essentially bond directly to a clean lased film and/or stent component, which can also be comprised of a polymer. Such an embodiment of the method can provide for a seamless interface between the coating and the lased film and/or stent component. Further, in another embodiment, more than one therapeutic agent can be delivered.

The amount of the therapeutic agent can be preferably sufficient to inhibit restenosis or thrombosis or to affect some other state of the stented tissue, for instance, heal a vulnerable plaque, and/or prevent rupture or stimulate endothelialization or limit other cell types from proliferating and from producing and depositing extracellular matrix molecules. The agent(s) can be selected from the group consisting of antiproliferative agents, anti-inflammatory, anti-matrix metalloproteinase, and lipid lowering, cholesterol modifying, anti-thrombotic and antiplatelet agents, in accordance with some embodiments. For vascular stent applications, some anti-proliferative agents that improve vascular patency include without limitation paclitaxel, Rapamycin, ABT-578, Biolimus A9, everolimus, dexamethasone, nitric oxide modulating molecules for endothelial function, tacrolimus, estradiol, mycophenolic acid, C6-ceramide, actinomycin-D and epothilones, and derivatives and analogs of each.

Some agents act as an antiplatelet agent, antithrombin agent, compounds to address other pathologic events and/or vascular diseases. Various therapeutic agents can be classified in terms of their sites of action in the host: agents that exert their actions extracellularly or at specific membrane receptor sites, those that act on the plasma membrane, within the cytoplasm, and/or the nucleus.

In addition to the aforementioned, therapeutic agents can include other pharmaceutical and/or biologic agents intended for purposes of treating body lumens other than arteries and/or veins). Therapeutic agents can be specific for treating nonvascular body lumens such as digestive lumens (e.g., gastrointestinal, duodenum and esophagus, biliary ducts), respiratory lumens (e.g., tracheal and bronchial), and urinary lumens (e.g., urethra). Additionally such embodiments can be useful in lumens of other body systems such as the reproductive, endocrine, hematopoietic and/or the integumentary, musculoskeletal/orthopedic and nervous systems (including auditory and ophthalmic applications); and finally, stent embodiments with therapeutic agents can be useful for expanding an obstructed lumen and for inducing an obstruction (e.g., as in the case of aneurysms).

Therapeutic release can occur by controlled release mechanisms, diffusion, interaction with another agent(s) delivered by intravenous injection, aerosolization, or orally. Release can also occur by application of a magnetic field, an electrical field, or use of ultrasound.

Stent Surface Coatings with Functional Properties

In addition to stents that can deliver a therapeutic agent, for instance delivery of a biological polymer on the stent such as a repellant phosphorylcholine, the stent can be coated with other bioresorbable polymers predetermined to promote biological responses in the body lumen desired for certain clinical effectiveness. Further the coating can be used to mask (temporarily or permanently) the surface properties of the polymer used to comprise the stent embodiment. The coating can be selected from the broad class of any biocompatible bioresorbable polymer which can include any one or combination of halogenated and/or non-halogenated which can or cannot comprise any poly(alkylene glycol). These polymers can include compositional variations including homopolymers and heteropolymers, stereoisomers and/or a blend of such polymers. These polymers can include for example, but are not limited to, polycarbonates, polyarylates, poly(ester amides), poly(amide carbonates), trimethylene carbonate, polycaprolactone, polydioxane, polyhydroxybutyrate, polyhydroxyvalerate, polyglycolide, polylactides and stereoisomers and copolymers thereof, such as glycolide/lactide copolymers. In an embodiment, the stent can be coated with a polymer that exhibits a negative charge that repels the negatively charged red blood cells' outer membranes thereby reducing the risk of clot formation. In another embodiment, the stent can be coated with a polymer that exhibits an affinity for cells, (e.g., endothelial cells) to promote healing. In yet another embodiment, the stent can be coated with a polymer that repels the attachment and/or proliferation of specific cells, for instance arterial fibroblasts and/or smooth muscle cells in order to lessen restenosis and/or inflammatory cells such as macrophages.

Described above are embodiments that can be modified with a coating to achieve functional properties that support biological responses. Such coatings or compositions of material with a therapeutic agent can be formed on stents or applied in the process of making a stent body via techniques such as dipping, spray coating, cross-linking combinations thereof, and the like, as mentioned and described above. Such coatings or compositions of material can also serve purpose other than delivering a therapeutic, such as to enhance stent retention on a balloon when the coating is placed intraluminally on the stent body and/or placed over the entire device after the stent is mounted on the balloon system to keep the stent in a collapsed formation. Other purposes can be envisioned by those skilled in the art when using any polymer material.

In accordance with an aspect of certain embodiments, a stent would have a coating applied that can alter the physical characteristics of the stent, such as to provide specific mechanical properties to the stent. The properties can include inter alia thickness, tensile strength, glass transition temperature, and surface finish. The coating can be preferably applied prior to final crimping or application of the stent to the catheter. The stent can then be applied to the catheter and the system can have either heat or pressure or both applied in a compressive manner. In the process, the coating can form frangible bonds with both the catheter and the other stent surfaces. The bonds would enable a reliable method of creating stent retention and of holding the stent crossing profile over time. The bonds would break upon the balloon deployment pressures. The coating would be a lower Tg than the substrate to ensure no changes in the substrate.

Stent Deployment

FIG. 63A-D are side cross-sectional views of a sheath-catheter arrangement 1800 illustrating deployment of a stent assembly 1802 mounted on a balloon of the catheter, according to an embodiment. For example, in FIG. 63A, the sheath-catheter assembly has been inserted into a body lumen 1804 to a desired location in preparation for deployment of the stent. As illustrated, the catheter can be a balloon-expandable catheter having a guidewire conduit, a catheter inflation lumen, a flexible tip, and a tip body 1808 at a distal end of the catheter. A sheath 1810 can comprise a proximal tube and a distal sheath portion attached to a distal end of the proximal tube. The sheath 1810 can also comprise a longitudinal slit through which a guidewire inserted into the guidewire and lumen of the catheter can pass.

The distal sheath portion can be attached to the tip body of the catheter. A pressure or frictional fit may provide sufficient stability to the sheath distal portion during passage of the catheter/stent assembly to a deployment site through the lumen. For example, the distal end of the sheath 1810 is firmly heat shrunk to the tip body. In certain embodiments, the distal sheath tip may be fit to a tapered portion of the tip body so as to urge the sheath material to elastically expand as the sheath is initially retracted. Similarly, an elastic band may be included overlapping the distal end of the sheath. Further, the distal sheath portion can comprise a perforation line at a distal end thereof in order to allow the distal sheath portion to be separated from the tip body during deployment. Alternatively, the distal sheath portion can be attached to the tip body with a breakable bond. In this regard, as shown in FIG. 63B, force can be applied to separate the distal sheath portion from the tip body of the catheter in order to proximally retract the sheath relative to the catheter.

Figure 63:
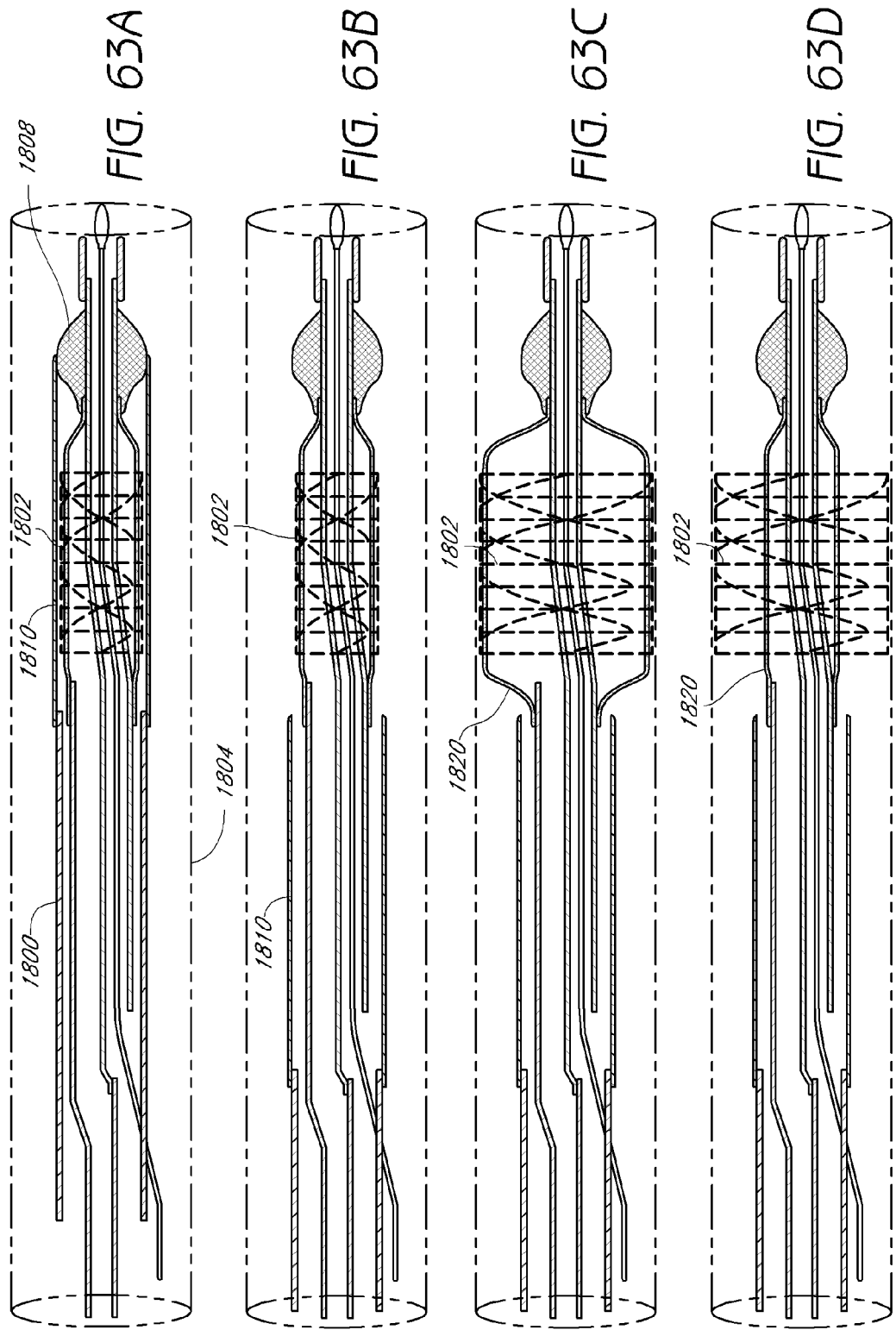
FIGS. 63A-D are cross-sectional side views of a sheath-catheter arrangement illustrating deployment of a stent assembly mounted on a balloon of the catheter, according to an embodiment.

FIG. 63C illustrates a balloon 1820 of the catheter being inflated in order to expand the stent to an expanded configuration. Thereafter, the balloon 1820 can be deflated as shown in FIG. 63D and the catheter and sheath can be withdrawn, leaving the stent deployed in the body lumen.

Figure 64:
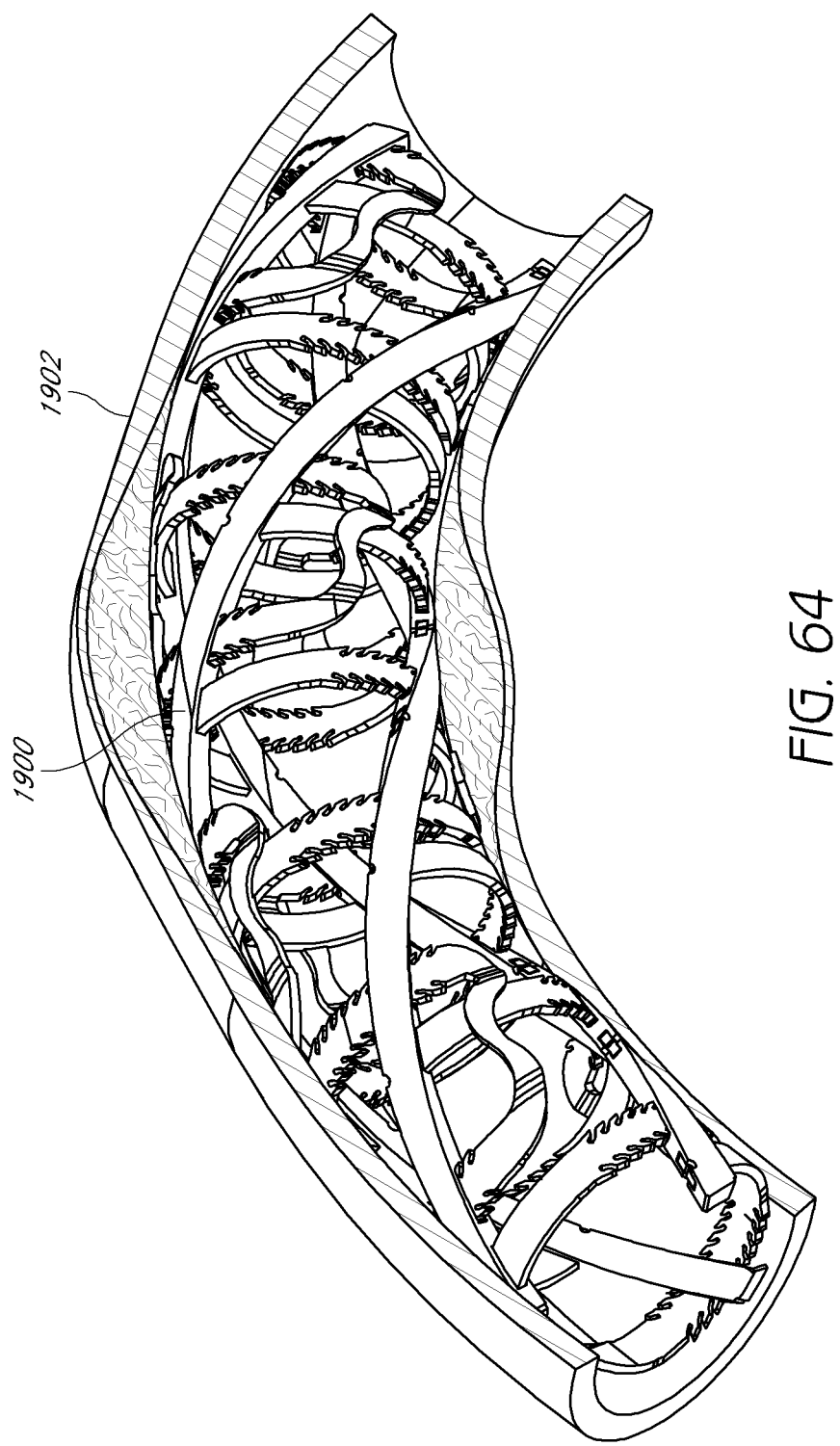
FIG. 64 illustrates a stent that is deployed in a lumen of the body, according to an embodiment.

Finally, FIG. 64 shows an embodiment of a stent 1900 placed in a lumen 1902 of the body. As discussed above, the stent 1900 will tend to exhibit superior structural and biocompatibility characteristics. For example, in contrast to prior art stents that may incorporate a helical design element, the stent 1900 does not exhibit foreshortening when expanding from the collapsed diameter to the expanded diameter. In other words, the unique helical backbone structure of the stent 1900, used in combination with the slide-and-lock expansion mechanism thereof, creates a stent that has excellent flexibility and stiffness, while preventing foreshortening, hinging, denting, kinking, and buckling. The unique incorporation of the slide-and-lock expansion mechanism allows the helix angle of the helical backbone members of the stent 1900 to be maintained regardless of the diameter of the stent 1900. Moreover, the unique alignment and orientation of the helical backbones, slots, and rail members of the stent 1900 provide a surprisingly efficient and effective expansion device exhibiting structural properties that are superior to prior art polymer stents and that rival structural properties of metal stents. As such, embodiments disclosed herein provide solutions to significant medical challenges and allow a patient to receive a stent that not only has structural properties that are optimized for the application, but that also is able to be resorbed into the body lumen upon completion of the goal.

As discussed above, embodiments disclosed herein can utilize a catheter having an expandable member, preferably an inflatable balloon, such as an angioplasty balloon, disposed along a distal end portion. An example of a balloon catheter for use with a stent is described in U.S. Pat. No. 4,733,665 to Palmaz, the disclosure of which is incorporated by reference herein. A stent on a catheter can be commonly collectively referred to as a stent system. Catheters include but are not limited to over-the-wire catheters, coaxial rapid-exchange designs and the Medtronic Zipper Technology that is a new delivery platform. Such catheters can include for instance those described in Bonzel U.S. Pat. Nos. 4,762,129 and 5,232,445 and by Yock U.S. Pat. Nos. 4,748,982, 5,496, 346, 5,626,600, 5,040,548, 5,061,273, 5,350,395, 5,451,233 and 5,749,888. Additionally, catheters can include for instance those as described in U.S. Pat. Nos. 4,762,129, 5,092,877, 5,108,416, 5,197,978, 5,232,445, 5,300,085, 5,445,646, 5,496,275, 5,545,135, 5,545,138, 5,549,556, 5,755,708, 5,769,868, 5,800,393, 5,836,965, 5,989,280, 6,019,785, 6,036,715, 5,242,399, 5,158,548, and 6,007,545. The disclosures of each of the above-cited patents are incorporated herein in their entirety by reference thereto.

Catheters can be specialized with highly compliant polymers and for various purposes such as to produce an ultrasound effect, electric field, magnetic field, light and/or temperature effect. Heating catheters can include for example those described in U.S. Pat. Nos. 5,151,100, 5,230,349, 6,447,508, and 6,562,021 as well as WO9014046A1. Infrared light emitting catheters can include for example those described in U.S. Pat. Nos. 5,910,816 and 5,423,321. The disclosures of each of the above-cited patents and patent publications are incorporated herein in their entirety by reference thereto.

An expandable member, such as an inflatable balloon, can be preferably used to deploy the stent at the treatment site. As the balloon is expanded, the radial force of the balloon overcomes the initial resistance of the constraining mechanism, thereby allowing the stent to expand.

The stent of embodiments described herein can be adapted for deployment using conventional methods known in the art and employing percutaneous transluminal catheter devices. This can include deployment in a body lumen by means of a balloon expandable design whereby expansion can be driven by the balloon expanding. Alternatively, the stent can be mounted onto a catheter that holds the stent as it is delivered through the body lumen and then releases the stent and allows it to self-expand into contact with the body lumen. The restraining means can comprise a removable/retractable sheath, a sheath that remains with the stent, and/or a mechanical aspect of the stent design.

The use of a sheath can be beneficial for several reasons. The sheath can be used to control delivery and deployment of the stent. For example, the sheath can be used to reduce and/or eliminate "negative aspects" of certain configurations of the stent, such as certain "slide-and-lock" designs; however, the sheath can also be used to make other designs possible.

The stent is composed of a polymeric sheath, most likely made out of a biodegradable material, which has sufficient elasticity to stretch during deployment of the stent and not break. The polymer also may include radiopaque, biodegradable polymers. The sheath is tubular in nature, and may include cutouts patterns to provide lower deployment pressures, increase flexibility and allow access to side branches of the artery. Ideally the sheath is very thin, such as less than 0.002", and ideality 0.0005" thick. The material need not have a high yield strength, but should have an elongation at break of greater than 150%, and possibly as much as 300%.

The sheath can be made from a variety of materials, such as polymers, natural materials, etc., which can include biodegradable materials. Further, the polymer can be radiopaque, biocompatible, and/or biodegradable, as discussed herein. In some embodiments, the sheath can be made from a resorbable material, and the sheath and stent can degrade together, thus leaving a healed, unencumbered vessel. The sheath material can be selected such that during stent expansion, the sheath can deform and expand plastically with the stent. In some embodiments, the sheath can have sufficient elasticity to stretch during deployment of the stent without breaking. Although high yield strength may not be required, the material preferably provides the sheath with an elongation at break of greater than 150%, and possibly as much as 300%.

Further, the sheath can be very thin, such as less than about 0.002 inches thick, but can preferably be about 0.0005 inches thick; other thicknesses can also be used in accordance with the teachings herein. Thus, the sheath can be beneficially used to eliminate or reduce negative aspects of certain stent designs, such as may be encountered during stent deployment, as well as to make other stent designs possible.

From the foregoing description, it will be appreciated that a novel approach for expanding a lumen has been disclosed. While several components, techniques and aspects have been described with a certain degree of particularity, it is manifest that many changes can be made in the specific designs, constructions and methodology herein above described without departing from the spirit and scope of this disclosure.

The methods which are described and illustrated herein are not limited to the sequence of acts described, nor are they necessarily limited to the practice of all of the acts set forth. Other sequences of acts, or less than all of the acts, or simultaneous occurrence of the acts, can be utilized in practicing embodiments.

While a number of embodiments and variations thereof have been described in detail, other modifications and methods of using and medical applications for the same will be apparent to those of skill in the art. Accordingly, it should be understood that various applications, modifications, materials, and substitutions can be made of equivalents without departing from the spirit of the inventions or the scope of the claims.

Various modifications and applications of the embodiments can occur to those who are skilled in the art, without departing from the true spirit or scope of the embodiments and inventions disclosed herein. It should be understood that the present inventions are not limited to the embodiments set forth herein for purposes of exemplification, but is to be defined only by a fair reading of the claims, including the full range of equivalency to which each element thereof is entitled.

For example, a uniform expandable stent can be provided that comprises a tubular member having a circumference which is expandable between at least a first collapsed diameter and at least a second expanded diameter, said tubular member comprising; at least two slidably engaged radial elements collectively defining the circumference of said tubular member, said at least two slidably engaged radial elements individually comprising; a flexible backbone, a first elongate member and a second elongate member, wherein said first elongate member and said second elongate member are substantially commonly oriented with respect to said flexible backbone, wherein said second elongate member is at least partially axially or circumferentially-offset with respect to said first elongate member.

In some embodiments, at least one of said first elongate member and said second elongate member can be a paired elongate member. In other embodiments, at least one of said first elongate member or said second elongate member can be an annular elongate member. In yet other embodiments, said annular elongate member can further comprise a substantially captive slot. Further, said flexible backbone can be configured to substantially coil about said tubular member.

Moreover, said flexible backbone can be configured to stair-step in a helical orientation about said tubular member. In this regard, said flexible backbone can further comprise at least one substantially captive slot. Additionally, said substantially captive slot can further comprise a locking member. Furthermore, said locking member can further comprise at least one of a tooth, a deflectable tooth, or a stop. In yet other embodiments, at least one of said elongate members can comprise at least one conjugate locking member, wherein said locking member and said conjugate locking member define an engagement means, said engagement means being adapted to allow substantially unidirectional slidable movement. Additionally, at least one of said elongate members can further comprise a first axial side and a second axial side, wherein at least one of said first axial side and said second axial side comprises at least one conjugate locking member. Finally, said at least one conjugate locking member is one of a tooth, a deflectable tooth, or a stop.

REFERENCES

Some of the references cited herein are listed below, the entirety of each one of which is hereby incorporated by reference herein:

Charles R, Sandirasegarane L, Yun J, Bourbon N, Wilson R, Rothstein R P, et al., *Ceramide-Coated Balloon Catheters Limit Neointimal Hyperplasia after Stretch Injury in Carotid Arteries*, Circulation Research 2000; 87(4): 282-288.

Coroneos E, Martinez M, McKenna S, Kester M., *Differential regulation of sphingomyelinase and ceramidase activities by growth factors and cytokines. Implications for cellular proliferation and differentiation*, J Biol. Chem. 1995; 270 (40): 23305-9.

Coroneos E, Wang Y, Panuska J R, Templeton D J, Kester M., *Sphingolipid metabolites differentially regulate extracellular signal-regulated kinase and stress-activated protein kinase cascades*, Biochem J. 1996; 316 (Pt 1): 13-7.

Jacobs L S, Kester M., *Sphingolipids as mediators of effects of platelet-derived growth factor in vascular smooth muscle cells*, Am. J. Physiology 1993; 265 (3 Pt 1): C740-7.

Tanguay J F, Zidar J P, Phillips H R, 3rd, Stack R S, *Current status of biodegradable stents*, Cardiol. Clin. 1994; 12(4): 699-713.

Nikol S, Huehns T Y, Hofling B., *Molecular biology and post-angioplasty restenosis*, Atherosclerosis 1996; 123 (1-2): 17-31.

BUDDY D. RATNER, ALLAN S. HOFFMAN, FREDERICK J. SCHOEN, AND JACK E. LEMONS, Biomaterials Science: An Introduction to Materials in Medicine (Elsevier Academic Press 2004).

What is claimed is:

1. An expandable slide and lock stent comprising:
a generally tubular body configured to radially expand from a contracted state to an expanded state, the body having a central lumen and defining a longitudinal axis, the body comprising:
a first backbone and a second backbone, the second backbone comprising a plurality of slots, the first and second backbones being circumferentially offset from each other;
a plurality of elongate members extending from the first backbone in a circumferential direction, each of the plurality of elongate members having a proximal end and a distal end, the proximal end being coupled to the first backbone; and
a locking mechanism on the second backbone;
wherein each particular one of the plurality of elongate members has one or more longitudinally adjacent elongate members of the plurality of elongate members, the distal end of each particular one of the plurality of elongate members being circumferentially offset from the distal end of the longitudinally adjacent elongate members of that particular one of the plurality of elongate members, and the plurality of elongate members being longitudinally offset from each other;
wherein each of the plurality of elongate members extending from the first backbone is configured to slidably engage and extend through a corresponding one of the plurality of slots in the second backbone, the locking mechanism being configured to facilitate substantially one-way movement of the elongate members through the corresponding slots, thereby inhibiting radial contraction of at least a portion of the tubular body.

2. The expandable slide and lock stent of claim 1, wherein each of the elongate members comprises a plurality of teeth configured to interact with the locking mechanism.

3. The expandable slide and lock stent of claim 2, wherein the plurality of teeth are disposed on opposite sides of each of the elongate members.

4. The expandable slide and lock stent of claim 2, wherein the plurality of teeth are disposed on one side of each of the elongate members.

5. The expandable slide and lock stent of claim 1, wherein each of the elongate members has at least a first and second portion, the thickness of the first and second portion being different.

6. The expandable slide and lock stent of claim 5, wherein each of the elongate members comprises a thinner portion located closer to the proximal end than a thicker portion.

7. The expandable slide and lock stent of claim 1, wherein the first and second backbones each comprise a plurality of adjacent backbone portions extending at approximately the same angle relative to the longitudinal axis.

8. The expandable slide and lock stent of claim 1, wherein the first and second backbones each comprise a plurality of adjacent backbone portions forming a generally stair-step pattern for at least a portion of the first and second backbones.

9. The expandable slide and lock stent of claim 1, wherein the plurality of slots are configured to capture a lateral, upper, and lower side of the elongate members, allowing only one degree of motion.

10. An expandable slide and lock stent comprising:
a generally tubular body configured to radially expand from a contracted state to an expanded state, the body having a central lumen and defining a longitudinal axis, the body comprising:
a first backbone and a second backbone, the second backbone comprising a plurality of slots, the first and second backbones being circumferentially offset from each other;
a plurality of pairs of elongate members extending from the first backbone in a circumferential direction, each of the plurality of elongate members having a proximal end and a distal end, the proximal end being coupled to the first backbone, wherein the distal end of each elongate member in a pair of elongate members circumferentially extends to approximately the same circumferential location; and
a locking mechanism on the second backbone;
wherein each particular pair of the plurality of pairs of elongate members has one or more longitudinally adjacent pairs of elongate members of the plurality of pairs of elongate members, the distal end of each of the elongate members of the particular pair of the plurality of pairs of elongate members being circumferentially offset from the distal end of the elongate members of the longitudinally adjacent pairs of that particular pair of the plurality of pairs of elongate members, and the plurality of pairs of elongate members being longitudinally offset from each other;
wherein each of the elongate members extending from the first backbone is configured to slidably engage and extend through a corresponding one of the plurality of slots in the second backbone, the locking mechanism being configured to facilitate substantially one-way movement of the elongate members through the corresponding slots, thereby inhibiting radial contraction of at least a portion of the tubular body.

11. The expandable slide and lock stent of claim 10, wherein each of the elongate members comprises a plurality of teeth configured to interact with the locking mechanism.

12. The expandable slide and lock stent of claim 11, wherein the plurality of teeth are disposed on opposite sides of each of the elongate members.

13. The expandable slide and lock stent of claim 11, wherein the plurality of teeth are disposed on one side of each of the elongate members.

14. The expandable slide and lock stent of claim 10, wherein each of the elongate members has at least a first and second portion, the thickness of the first and second portion being different.

15. The expandable slide and lock stent of claim 14, wherein each of the elongate members comprises a thinner portion located closer to the proximal end than a thicker portion.

16. The expandable slide and lock stent of claim 10, wherein the first and second backbones each comprise a plurality of adjacent backbone portions extending at approximately the same angle relative to the longitudinal axis.

17. The expandable slide and lock stent of claim 10, wherein the first and second backbones each comprise a plurality of adjacent backbone portions forming a generally stair-step pattern for at least a portion of the first and second backbones.

18. The expandable slide and lock stent of claim 10, wherein the plurality of slots are configured to capture a lateral, upper, and lower side of the elongate members, allowing only one degree of motion.

* * * * *